(12) United States Patent
Denis et al.

(10) Patent No.: US 9,321,722 B2
(45) Date of Patent: Apr. 26, 2016

(54) BIS-INDOLIC DERIVATIVES, THEIR USES IN PARTICULAR AS ANTIBACTERIALS

(75) Inventors: Jean-Noël Denis, Jarrie (FR); Claude Marcelle Jolivalt, Sceaux (FR); Louis Maurin Max Maurin, Meylan (FR); Olga Nikolaevna Burchak, Meylan (FR)

(73) Assignee: UNIVERSITE JOSEPH FOURIER, Grenoble (FR)

( * ) Notice: Subject to any disclaimer, the term of this patent is extended or adjusted under 35 U.S.C. 154(b) by 20 days.

(21) Appl. No.: 14/234,255

(22) PCT Filed: Jul. 20, 2012

(86) PCT No.: PCT/EP2012/064339
§ 371 (c)(1),
(2), (4) Date: Apr. 17, 2014

(87) PCT Pub. No.: WO2013/014104
PCT Pub. Date: Jan. 31, 2013

(65) Prior Publication Data
US 2014/0228359 A1    Aug. 14, 2014

(30) Foreign Application Priority Data

Jul. 22, 2011    (EP) .................................. 11305964

(51) Int. Cl.
| | | |
|---|---|---|
| *C07D 403/12* | (2006.01) |
| *C07D 209/18* | (2006.01) |
| *C07D 401/14* | (2006.01) |
| *C07D 413/14* | (2006.01) |
| *C07D 403/14* | (2006.01) |
| *C07D 209/14* | (2006.01) |
| *C07D 209/16* | (2006.01) |
| *A61K 31/404* | (2006.01) |
| *A61K 31/454* | (2006.01) |
| *A61K 31/496* | (2006.01) |
| *A61K 31/5377* | (2006.01) |
| *A61K 45/06* | (2006.01) |
| *C07D 209/20* | (2006.01) |

(52) U.S. Cl.
CPC ............ *C07D 209/18* (2013.01); *A61K 31/404* (2013.01); *A61K 31/454* (2013.01); *A61K 31/496* (2013.01); *A61K 31/5377* (2013.01); *A61K 45/06* (2013.01); *C07D 209/14* (2013.01); *C07D 209/16* (2013.01); *C07D 209/20* (2013.01); *C07D 401/14* (2013.01); *C07D 403/14* (2013.01); *C07D 413/14* (2013.01)

(58) Field of Classification Search
CPC ...................................... C07D 403/12
USPC ......................................... 548/455
See application file for complete search history.

(56) References Cited

U.S. PATENT DOCUMENTS

2010/0144726 A1    6/2010    Denis et al.

OTHER PUBLICATIONS

Guinchard. Document No. 161:697258, retrieved from CAPLUS; 2006.*
Guinchard, et al. Document No. 147:448961, retrieved from CAPLUS; Aug. 21, 2007.*
Afsah, et al. Document No. 102:6101, retrieved from CAPLUS; Jan. 12, 1985.*
Kawasaki, et al. Document No. 140:94177, retrieved from CAPLUS; Nov. 6, 2003.*
International Search Report, Dated Sep. 11, 2012, in PCT/EP2012/064339.

* cited by examiner

*Primary Examiner* — Shawquia Jackson
(74) *Attorney, Agent, or Firm* — Young & Thompson

(57) ABSTRACT

The present invention relates to novel bis-indolic derivatives, processes for their preparation, and their potential use as new antibacterial drugs.

20 Claims, No Drawings

BIS-INDOLIC DERIVATIVES, THEIR USES IN PARTICULAR AS ANTIBACTERIALS

The present invention relates to novel bis-indolic derivatives, processes for their preparation, and their potential use as new antibacterial drugs.

Penicillin G was the first natural antibiotic identified, first by Ernst Duchesne in the 19$^{th}$ century, then rediscovered in 1928 by Alexander Fleming.

Sulfonamides, synthetic antibiotics, have emerged at the same time as penicillin G. Prontosil was the first compound of this class to be synthesized in 1932 by Gerhard Domagk. However, the sulfamidotherapy only began after J. and TH. Trefouël, F. Nitti and D. Bovet discovered in 1935 that prontosil was metabolized in the active compound sulfanilamide.

Most of the major classes of natural antibiotics have been isolated and characterized between 1940 and 1960. The quinolones, synthetic antibiotics, were introduced in 1962. Then, it was only 40 years later, in 2000, that a novel class of synthetic antibiotics was discovered: the oxazolidinone class.

Despite the discovery of numerous active compounds, their medical interest has been more or less quickly reduced because of development of bacterial resistances. Resistance mechanisms include the inactivation of the drug by specific enzymes, alteration of the antibiotic target, bacterial wall impermeability to antibiotic entry, and efflux of the antibiotic from the bacterial cytosol. These mechanisms usually develop within a few years after a new drug is introduced into clinical practice.

To overcome the problem of antibiotic resistance, three ways can be considered:

1) structural modifications of existing drugs to obtain new compounds with maintained activity in the presence of known resistance mechanisms 2) restoration of the activity of existing antibiotics by combining a compound that inhibits bacterial resistance mechanisms and 3) development of novel antibiotic classes with original chemical structures and modes of action, as to avoid the deleterious effect of previously selected antibiotic resistance mechanisms, these new antibiotics will thus be effective against major antibiotic-resistant human pathogens.

As an example, *Staphylococcus aureus* (a major human pathogen) may resist to antibiotics by the production of enzymes (e.g., penicillinase leading to resistance to penicillin G, transferases leading to resistance to aminoglycosides), by the modification of natural targets (e.g., acquisition of mecA gene in methicillin-resistant strains), or by efflux systems (e.g., NorA and fluoroquinolone resistance).

Because the dramatic increase in antibiotic resistances became a public health problem, the pharmaceutical industry relaunched at the beginning of the 1990's the research on antibacterial compounds. This led to the linezolide success (Y. Van Laethem, J. Sternon *Rev. Med. Brux.* 2004, 25, 47-50), oxazolidinones development by Pfizer, and daptomycin development by Novartis (F. P. Tally, M. F. DeBruin, <<Development of daptomycin for Gram-positive infections>>, *Journal of Antimicrobial Chemotherapy*, 2000, 46, 523-526; L. Robbel, M. A. Marahiel <<Daptomycin, a bacterial lipopeptide synthesized by a nonribosomal machinery>> *J. Biol. Chem.* 2010, 285, 27501-27508).

Since 2000, oxazolidinones and cyclic lipopeptides have been the two only new antibiotic classes with a complete original structure approved in the treatment of Gram-positive bacterial infections. Linezolide and daptomycin are the only commercialized compounds of the oxazolidinone and lipopeptide classes, respectively. Their antibacterial spectrum comprises most of Gram-positive bacteria responsible for human infections, including multi-drug resistant strains such as the vancomycin-resistant *Enterococcus* sp. (VRE) and methicillin-resistant *Staphylococcus aureus* (MRSA).

Other new antibiotics with a known structural moiety have been recently commercialized or are currently under development (V. Cattoir, C. Daurel, <<Médecine et Maladies infectieuses>>, 2010, 40, 135-154) such as tigecycline, first glycylcycline that is a new class of hemi synthetic antibiotics derived from the tetracycline family (L. R. Peterson, <<A review of tigecycline — the first glycylcyline>>, *Int. J. Antimicrob. Agents*, 2008, 32, S215-222). Tigecycline has a broad antibacterial spectrum comprising aerobic or anaerobic, Gram-positive or Gram-negative bacteria.

Among β-lactams, new carbapenems have been developed. They have a broad antibacterial spectrum because of greater stability to the action of most β-lactamases. Three carbapénèms are currently commercialized: imipenem, meropenem and ertapenem. A fourth one, doripenem, is close to the commercialization (M. Wolff, M.-L. Joly-Guillou, O. Pajot, <<Les carbapénèmes>>, *Réanimation*, 2009, 18, 5199-5208). Their antibacterial spectrum encompasses most of aerobic and anaerobic bacteria. However, they are not effective against multi-drug resistant bacteria such as MRSA, methicillin-resistant coagulase-negative staphylococci, penicillin-resistant *E. faecium*, carbapenemase-producing Enterobacteraceae or *Pseudomonas aeruginosa*, and *Stenotrophomonas maltophilia*.

Two new cephalosporins (ceftobiprole and ceftaroline) with a broad antibacterial spectrum and an activity against MRSA are currently in phase III clinical trial.

Pharmacokinetic parameters of vancomycin (lead of glycopeptides) and its relative toxicity have always been a hindrance to its intensive clinical use. Many endeavors have been accomplished to optimize its structure and this work has recently led to the development of the lipopeptides. Structurally close to the glycopeptide family, these compounds have a lipophilic chain added to the glycopeptide moiety (M. T. Guskey, B. T. Tsuji, <<A comparative review of the lipoglycopeptides: oritavancin, dalbavancin, and telavancin>>, *Pharmacotherapy* 2010, 30, 80-94). Among these three compounds, telavancin is the only compound to be commercialized, the two others being still in phase II clinical trials.

All these new compounds, except oxazolidinones and lipopeptides, present a structure derived from a molecule with a biosynthetized active moiety. This may facilitate rapid development by bacteria of resistance mechanisms to these new compounds. In addition, most of these new molecules have very complex structures, leading the big pharmaceutical company to hesitate to invest in this medicinal domain because the earning potential is unpredictable and could be even null in case of a fast apparition of resistance.

There is thus an urgent need to develop new compounds that may help solving the problem of bacterial resistance to currently available antibiotics. This may be obtained by developing new classes of antibacterial agents with original structures and modes of action, and thus able to maintain their activity against microorganisms harboring known resistance mechanisms. Ideally, the newer compounds may prevent or delay the emergence of new resistance mechanisms leading to their inactivation. Another solution will consist in developing molecules liable to block existing bacterial resistance mechanisms, in order to restore the activity of currently available antibiotics.

Recently, a new class of molecules showing antimicrobial activity named indole derivatives has been disclosed in the international application WO 2008110690. However, the minimum inhibitory concentrations (MIC) obtained for various bacterial species, especially multi-drug resistant bacteria, are relatively high.

One objective of the present invention is to provide new compounds, with new structures, and an improved antibacterial activity as compared to monoindole derivatives, including against bacteria resistant to multiple antibiotics.

Another aim of the invention is to provide new compounds with an original structure liable to inhibit the NorA efflux pump of *Staphylococcus aureus*, responsible for fluoroquinolone resistance in this species.

Another aim of the invention is to provide new compounds having both an antibiotic activity when used alone or in association with fluoroquinolones, and a NorA efflux pump inhibition activity.

Still another aim is to provide pharmaceutical compositions comprising said new compounds.

The present invention relates to compounds of the following formula I:

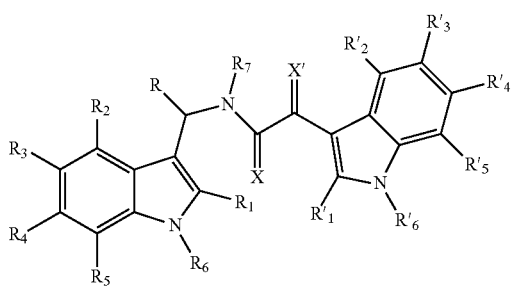

I wherein:

X and X' represent independently from each other O or S, and a) $R_1$, $R_2$, $R_3$, $R_4$, $R_5$, $R'_1$, $R'_2$, $R'_3$, $R'_4$ and $R'_5$ represent independently from each other:

H, a linear or branched $(C_1$-$C_7)$alkyl, if appropriate substituted by:

a halogen, a hydroxyl group, a $OR_a$ or $NR_aR_b$, wherein $R_a$ and $R_b$ represent:

H, a linear or branched $(C_1$-$C_7)$-alkyl, a $(C_3$-$C_7)$-cycloalkyl, an aryl substituted or not, $CH_2$-aryl, CO—$(C_1$-$C_7)$-alkyl, CO-aryl, $CO_2$—$(C_1$-$C_7)$-alkyl, $CO_2$-aryl, wherein aryl is a substituted or not aromatic group or a substituted or not heteroaromatic group a $(C_3$-$C_7)$-cycloalkyl, an aryl substituted or not, $CH_2$-aryl, CO—$(C_1$-$C_7)$-alkyl, CO-aryl, $CO_2$—$(C_1$-$C_7)$-alkyl, $CO_2$-aryl, wherein aryl is a substituted or not aromatic group or a substituted or not heteroaromatic group, F, Cl, Br, I, $CF_3$, OH, $OR_a$, $OCF_3$, $COCF_3$, $NH_2$, $NHR_a$, $NR_aR_b$, wherein $R_a$ and $R_b$ represent:

H, a linear or branched $(C_1$-$C_7)$-alkyl, a $(C_3$-$C_7)$-cycloalkyl, an aryl substituted or not, $CH_2$-aryl, CO—$(C_1$-$C_7)$-alkyl, CO-aryl, $CO_2$—$(C_1$-$C_7)$-alkyl, $CO_2$-aryl, wherein aryl is a substituted or not aromatic group or a substituted or not heteroaromatic group, CN and $NO_2$ provided that $R_1$, $R_2$, $R_3$, $R_4$, $R_5$, $R'_1$ are different from CN and $NO_2$.

$(CH_2)_n$—Z, —$(CH_2)_n$—OH, —$(CH_2)_n$—$CO_2$—$(C_1$-$C_7)$-alkyl, —$(CH_2)_n$—$CO_2H$ wherein n=2 to 12, Z is a halogen and alkyl being as defined above, R represents H, a $(C_1$-$C_7)$-alkyl, $CH_2NHCO_2$—$(C_1$-$C_7)$-alkyl, $CH_2NHCO_2$—$(C_3$-$C_7)$-cycloalkyl, $CO_2H$, $CO_2$—$(C_1$-$C_7)$-alkyl, $CO_2$—$(C_3$-$C_7)$-cycloalkyl, $(CH_2)_nOH$, $CH_2NH(CH_2)_n$—OH, $CH_2NH(CH_2)_n$—$NR_aR_b$, CONH—$(C_1$-$C_7)$-alkyl, CONH—$(C_3$-$C_7)$-cycloalkyl, CONH-aryl, CONH—$(CH_2)_nOH$, CONH—$(CH_2)_nNR_aR_b$, wherein n=2 to 12 and $R_a$, $R_b$, aryl and alkyl being as defined above, $R_6$ and $R'_6$ represent independently from each other H, $(C_1$-$C_7)$-alkyl, $SO_2$aryl, wherein aryl being as defined above, OH, O—$(C_1$-$C_7)$-alkyl, CO—$(C_1$-$C_7)$-alkyl, CO-aryl, $CH_2NH_2$, $CH_2NHRa$, $CH_2N_aR_b$, $Si(R_c)_3$, the Rc groups being identical or different and representing independently of each other a linear or branched $(C_1$-$C_7)$-alkyl, a $(C_3$-$C_7)$-cycloalkyl, or an aryl, aryl and alkyl being as defined above, $R_7$ represents H, OH, $OR_a$, $R_a$ being as defined above, or b) R and $R_7$ are joined together to form a cycle of formula I-a:

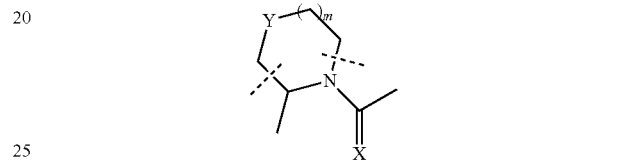

I-a wherein Y represents:

N—$R_8$ wherein $R_8$ represents H, $(C_1$-$C_7)$-alkyl, $(C_3$-$C_7)$-cycloalkyl, CO—$(C_1$-$C_7)$-alkyl, CO—$(C_3$-$C_7)$-cycloalkyl, $CO_2$—$(C_1$-$C_7)$-alkyl, $CO_2$—$(C_3$-$C_7)$-cycloalkyl,

O,

S, $CH_2$, $CHR_8$ wherein $R_8$ represents $(C_1$-$C_7)$-alkyl, $(C_3$-$C_7)$-cycloalkyl, CO—$(C_1$-$C_7)$-alkyl, CO—$(C_3$-$C_7)$-cycloalkyl, $CO_2$—$(C_1$-$C_7)$-alkyl, $CO_2$—$(C_3$-$C_7)$-cycloalkyl, m=0, 1 said cycle being optionally substituted by OH, a linear or branched $O(C_1$-$C_7)$-alkyl, a $O(C_3$-$C_7)$-cycloalkyl, $NH_2$ or $NR_aR_b$, $R_a$ and $R_b$ being as defined above, $R_1$, $R_2$, $R_3$, $R_4$, $R_5$, $R'_1$, $R'_2$, $R'_3$, $R'_4$, $R'_5$, $R_6$ and $R'_6$ being as defined above, or c) R and $R_7$ are joined together to form a cycle of formula I-b:

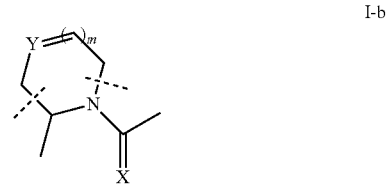

I-b wherein Y represents:

CH, $CR_8$ wherein $R_8$ represents $(C_1$-$C_7)$-alkyl, $(C_3$-$C_7)$-cycloalkyl, CO—$(C_1$-$C_7)$-alkyl, CO—$(C_3$-$C_7)$-cycloalkyl, $CO_2$—$(C_1$-$C_7)$-alkyl, $CO_2$—$(C_3$-$C_7)$-cycloalkyl, m=1

$R_1$, $R_2$, $R_3$, $R_4$, $R_5$, $R'_1$, $R'_2$, $R'_3$, $R'_4$, $R'_5$, $R_6$ and $R'_6$ being as defined above, and their pharmaceutically acceptable salts, for use as a medicament, suitable especially for an antibacterial activity and/or NorA efflux pump inhibitor.

By linear alkyl group from $C_1$ to $C_7$ is meant a group such as methyl, ethyl, propyl, butyl, pentyl, hexyl or heptyl.

By branched alkyl group is meant an alkyl group as defined above bearing substituents selected from the list of linear alkyl groups defined above, said linear alkyl group being also liable to be branched.

Both linear and branched alkyl definitions apply to the entire specification.

By cycloalkyl group from $C_3$ to $C_7$ is meant a group such as cyclopropyl, cyclobutyl, cyclopentyl, cyclohexyl or cycloheptyl. Such groups can also be substituted by a linear or branched alkyl group as defined above.

The definition of cycloalkyl group applies also to the entire specification.

The term "aryl" refers to any functional group or substituent derived from a simple aromatic ring.

The aryl can be substituted by one or more groups chosen independently among an halogen, a linear or branched ($C_1$-$C_7$)-alkyl, a ($C_3$-$C_7$)-cycloalkyl, CN, $CF_3$, OH, $OR_x$, $NH_2$, $NHR_x$, $NR_xR_y$, $R_x$ and $R_y$ being a linear or branched ($C_1$-$C_7$)-alkyl, a ($C_3$-$C_7$)-cycloalkyl, an aryl substituted or not, $CH_2$-aryl, CO—($C_1$-$C_7$)-alkyl or cycloalkyl, CO-aryl, $CO_2H$, $CO_2$—($C_1$-$C_7$)-alkyl or cycloalkyl, The term "heteroaromatic" refers to a compound having the characteristics of an aromatic compound whilst having at least one non-carbon atom in the ring.

The heteroaromatic can be substituted by one or more groups chosen independently among those defined for aryl.

In formula I-a, if m=0, then the cycle is constituted of five atoms, if m=1, the cycle is constituted of six atoms.

In formula I-b, if m=1, then the cycle is constituted of six atoms.

A basic group such as the nitrogen of the indole moiety or an amino group present on the molecule can be under a salt form, the salt being any pharmaceutically acceptable salt obtained by reaction of an inorganic acid, an organic acid or a halogenoalkyl, on an amino group to give a quaternary ammonium.

Examples of inorganic acid allowing obtaining pharmaceutically acceptable salts include, without being limited to them, hydrochloric acid, hydrobromic acid, hydroiodic acid, nitric acid, carbonic acid, formic acid, monohydrogenocarbonic acid, phosphoric acid, monohydrogenophosphoric acid, dihydrogenophosphoric acid, perchloric acid, sulfuric acid, monohydrogenosulfuric acid.

Examples of organic acid allowing obtaining pharmaceutically acceptable salts include, without being limited to them, acetic acid, lactic acid, propionic acid, butyric acid, isobutyric acid, palmitic acid, malic acid, glutamic acid, hydroxymalic acid, malonic acid, benzoic acid, succinic acid, glycolic acid, suberic acid, fumaric acid, mandelic acid, phthalic acid, salicylic acid, benzenesulfonic acid, p-tolylsulfonic acid, citric acid, tartaric acid, methanesulfonic acid, hydroxynaphthoic acid.

As the molecule can also bear an acid group, and as at least one substituent of the indole moiety or of the aryl or heteroaromatic groups can be a phenol, they can also be under a pharmaceutically acceptable salt form.

The salt can be obtained with organic or mineral bases, to give for instance alkali metal salts such as, lithium, sodium, potassium salts.

As an example, see Berge et al., "Pharmaceutical Salts", *Journal of Pharmaceutical Science,* 1977, 66, 1-19.

When R is different from H, the molecule presents an asymmetric carbon and thus compounds of the invention can be the R or the S enantiomer, a racemic mixture of both enantiomers or a mixture comprising 0.01%-99.99% of the R enantiomer and 99.99%-0.01% of the S enantiomer.

The inventors have found that some compounds bearing two indole moieties, present an antibiotic activity on bacteria, and said compounds presenting an original structure with regards to all existing antibiotics; they are promising candidate not to develop a resistance or to develop only late resistance.

The finding of the inventors is that compounds lacking the indole moiety borne by the carbonyl group of the keto-amide function lose completely the antibiotic activity (see comparative examples).

The inventors have also found that some compounds are NorA efflux pump inhibitor and thus could be used in association with known antibiotics allowing reversing the antibiotic resistance toward said antibiotics.

Further, compounds of the invention present also both intrinsic antibacterial activity and NorA efflux pump inhibitor activity.

In an advantageous embodiment, the present invention relates to compounds defined above, wherein:

X and X' are as defined above, $R_1$, $R_2$, $R_3$, $R_4$, $R_5$, $R_6$, $R'_1$, $R'_2$, $R'_3$, $R'_4$, $R'_5$ and $R'_6$ are as defined above, R represents H, a ($C_1$-$C_7$)-alkyl, $CH_2NHCO_2$—($C_1$-$C_7$)-alkyl, $CH_2NHCO_2$—($C_3$-$C_7$)-cycloalkyl, $CO_2H$, $CO_2$—($C_1$-$C_7$)-alkyl, $CO_2$—($C_3$-$C_7$)-cycloalkyl, $(CH_2)_nOH$, $CH_2NH(CH_2)_n$—OH, $CH_2NH(CH_2)_n$—$NR_aR_b$, CONH—($C_1$-$C_7$)-alkyl, CONH—($C_3$-$C_7$)-cycloalkyl, CONH-aryl, CONH—$(CH_2)_nOH$, CONH—$(CH_2)_nNR_aR_b$, wherein n=2 to 12 and $R_a$, $R_b$, aryl and alkyl being as defined above.

$R_7$ represents H, OH, $OR_a$, $R_a$ being as defined above.

In this embodiment, compounds of the invention are compounds wherein R and $R_7$ are not joined and presenting an antibacterial activity and/or NorA efflux pump inhibitor.

In an advantageous embodiment, the present invention relates to compounds defined above, wherein:

X and X' are as defined above, $R_1$, $R_2$, $R_3$, $R_4$, $R_5$, $R_6$ $R'_1$, $R'_2$, $R'_3$, $R'_4$, $R'_5$ and $R'_6$ are as defined above, and R and $R_7$ are joined together to form a cycle of formulas I-a and I-b as defined above.

In this embodiment, compounds of the invention are cyclic compounds presenting an antibacterial activity and/or NorA efflux pump inhibitor.

In an advantageous embodiment, the present invention relates to compounds defined above, wherein the antibacterial activity is against Gram-positive and Gram-negative bacteria.

Another advantage of the invention is to provide antibiotics active both against Gram-positive and Gram-negative bacteria.

The term "Gram-positive bacteria" refers to the two bacterial phyla defined in the Bergey's manual of systematic bacteriology ($2^{nd}$ edition, G. M. Garrity (ed.), Springer, 2005), Actinobacteria, and Firmicutes, and include the well known genera *Staphylococcus, Streptococcus; Enterococcus, Listeria* and *Bacillus,*

The term "Gram-negative bacteria" refers to 22 bacterial phyla defined in the Bergey's manual of systematic bacteriology ($2^{nd}$ edition, G. M. Garrity, Springer, 2005), Aquificae, Thermotogae, Thermodesulfobacteria, Deinococcus-Thermus, Chrysiogenetes, Chloroflexi, Thermomicrobia, Nitrospira, Deferribacteres, Cyanobacteria, Chlorobia, Proteobacteria, Planctomycetes, Chlamydiae, Spirochaetes, Fibrobacteres, Acidobacteres, Bacteroidetes, Fusobacteria, Verrucomicrobia, Dictyoglomi, and Gemmatimonadetes.

Proteobacteria, in particular, include a large number of human pathogens such as the Enterobacteriaceae, Pseudomonadaceae, Vibrionaceae, Moraxellaceae, Neisseriaceae and Pasteurellaceae families.

In an advantageous embodiment, the present invention relates to compounds of formula I defined above, wherein said compounds are narrow spectrum antibiotics having the advantage not to alter the intestinal microbiota.

By the expression "narrow-spectrum" it must be understood that compounds of the invention are able to act as an antibiotic effective against only specific families of bacteria (in the invention Gram-positive *Staphylococcus aureus* and coagulase-negative *Staphylococcus* species, and to a lesser extent Gram-positive *Streptococcus* and *Bacillus* species and Gram-negative *Haemophilus* species).

This is in contrast to a broad-spectrum antibiotic which is effective against a wide range of disease-causing bacteria.

In an advantageous embodiment, the present invention relates to compounds defined above, wherein said bacteria are resistant to conventional antibiotics.

Compounds of the invention are not only active against sensitive bacteria but also present the advantage to be active against bacteria resistant to currently available antibiotics.

In an advantageous embodiment, the present invention relates to compounds defined above, wherein the antibacterial activity is against *Staphylococcus* species, in particular *Staphylococcus aureus*, especially *Staphylococcus aureus* resistant to β-lactams (including methicillin-resistant strains, also referred as MRSA), *Staphylococcus aureus* resistant to glycopeptides (vancomycin-resistant or glycopeptides-resistant strains, also referred as VISA or GISA) and *Staphylococcus aureus* resistant to fluoroquinolones.

Compounds of the invention are also active against coagulase-negative *Staphylococcus* species such as *Staphylococcus epidermidis*, including strains resistant to β-lactam or fluoroquinolone antibiotics.

Compounds of the invention also present the advantage to be active against bacteria that are multi-resistant, i.e., resistant to several classes of antibiotics including those cited above.

In an advantageous embodiment, the present invention relates to compounds defined above, having further an antifungal and/or antiviral activity.

A further advantage of the compounds of the invention is that they present not only an antibacterial activity but also an antifungal activity or an antiviral activity. Some of the compounds also present the triple activity.

In an advantageous embodiment, the present invention relates to compounds defined above, of the following formula II:

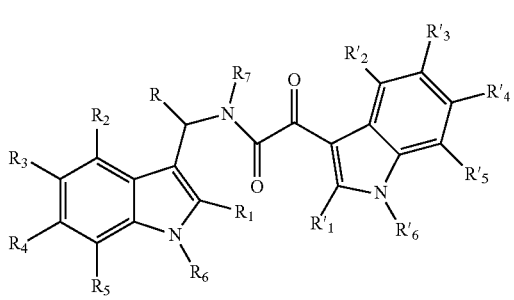

wherein $R_1$, $R_2$, $R_3$, $R_4$, $R_5$, $R_6$, $R_7$, $R'_1$, $R'_2$, $R'_3$, $R'_4$, $R'_5$, $R'_6$ and R are as defined above.

In this embodiment, R and $R_7$ are not joined together and do not form a cycle of formula I-a or I-b.

In an advantageous embodiment, the present invention relates to compounds defined above, of the following formula II-1:

II-1 wherein $R_1$, $R_2$, $R_3$, $R_4$, $R_5$, $R_6$, $R_7$, $R'_1$, $R'_2$, $R'_3$, $R'_4$, $R'_5$, $R'_6$ and R are as defined above.

In this embodiment, R and $R_7$ are not joined together and do not form a cycle of formula I-a or I-b.

In an advantageous embodiment, the present invention relates to compounds defined above, of the following formula II-3:

II-3 wherein $R_1$, $R_2$, $R_3$, $R_4$, $R_5$, $R_6$, $R_7$, $R'_1$, $R'_2$, $R'_3$, $R'_4$, $R'_5$, $R'_6$ and R are as defined above.

In this embodiment, R and $R_7$ are not joined together and do not form a cycle of formula I-a or I-b.

In an advantageous embodiment, the present invention relates to compounds defined above, having the formula I or II wherein $R_6$ and $R'_6$ represent H.

In this embodiment, R and $R_7$ are not joined together and do not form a cycle of formula I-a or I-b.

In an advantageous embodiment, the present invention relates to compounds defined above, having the formula I or II wherein $R_2$, $R_5$, $R'_2$ and $R'_5$ represent H.

In this embodiment, R and $R_7$ are not joined together and do not form a cycle of formula I-a or I-b.

In an advantageous embodiment, the present invention relates to compounds defined above, having the formula I or II wherein $R_7$ represent H.

In this embodiment, R and $R_7$ are not joined together and do not form a cycle of formula I-a or I-b.

In an advantageous embodiment, the present invention relates to compounds defined above, having the formula I or II, wherein $R_6$ and $R'_6$ are different.

In this embodiment, R and $R_7$ are not joined together and do not form a cycle of formula I-a or I-b.

In an advantageous embodiment, the present invention relates to compounds defined above, having the formula I or II, wherein $R_1$ is different from $R'_1$ and/or $R_2$ is different from R'$_2$, and/or R$_3$ is different from R'$_3$ and/or R$_4$ is different from R'$_4$ and/or R$_5$ is different from R'$_5$.

In this embodiment, R and R$_7$ are not joined together to form a cycle of formula I-a or I-b.

In an advantageous embodiment, the present invention relates to compounds defined above, having the formula I or II, wherein R$_1$ is similar to R'$_1$, and/or R$_2$ is similar to R'$_2$, and/or R$_3$ is similar to R'$_3$, and/or R$_4$ is similar to R'$_4$, and/or R$_5$ is similar to R'$_5$ and/or R$_6$ is similar to R'$_6$.

In this embodiment, R and R$_7$ are not joined together and do not form a cycle of formula I-a or I-b.

In an advantageous embodiment, the present invention relates to compounds defined above, of the following formula III:

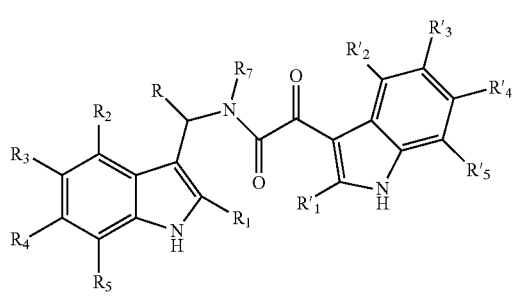

III wherein R$_1$, R$_2$, R$_3$, R$_4$, R$_5$, R$_7$, R'$_1$, R'$_2$, R'$_3$, R'$_4$, R'$_5$ and R are as defined above.

In this embodiment, R and R$_7$ are not joined together and do not form a cycle of formula I-a or I-b.

In an advantageous embodiment, the present invention relates to compounds defined above, of the following formula IV:

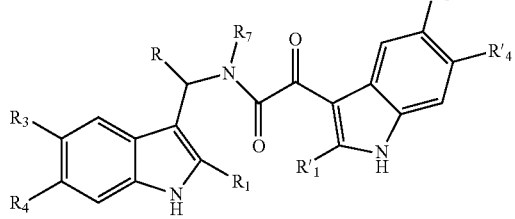

IV wherein R$_1$, R$_3$, R$_4$, R$_7$, R'$_1$, R'$_3$, R'$_4$ and R are as defined above.

In this embodiment, R and R$_7$ are not joined together and do not form a cycle of formula I-a or I-b.

In an advantageous embodiment, the present invention relates to compounds defined above, of the following formula V

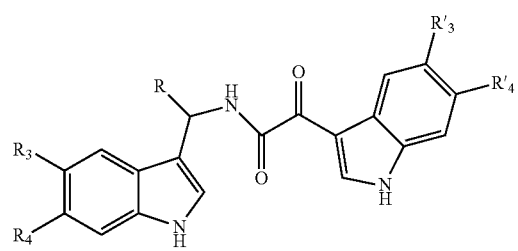

V wherein:
R$_3$, R$_4$, R'$_3$ and R'$_4$ represent independently from each other H, F, Cl, Br, I, R represents a (C$_1$-C$_7$)-alkyl, CH$_2$NHCO$_2$—(C$_1$-C$_7$)-alkyl, CO$_2$H, CO$_2$—(C$_1$-C$_7$)-alkyl, CONH—(CH$_2$)$_n$OH, (CH$_2$)$_n$OH, CH$_2$NH(CH$_2$)$_n$—OH, CH$_2$NH(CH$_2$)$_n$—NR$_a$R$_b$, CONH—(CH$_2$)$_n$NR$_a$R$_b$.

In an advantageous embodiment, the present invention relates to compounds of formula V defined above, wherein:
R$_3$, R$_4$, R'$_3$ and R'$_4$ represent independently from each other H, F, Cl, Br, I, at least one of
R$_3$, R$_4$, R'$_3$ and R'$_4$ represents F, Cl, Br, I, R represents a (C$_1$-C$_7$)-alkyl, CH$_2$NHCO$_2$—(C$_1$-C$_7$)-alkyl, CO$_2$H, CO$_2$—(C$_1$-C$_7$)-alkyl, CONH—(CH$_2$)$_n$OH, (CH$_2$)$_n$OH, CH$_2$NH(CH$_2$)$_n$—OH, CH$_2$NH(CH$_2$)$_n$—NR$_a$R$_b$, CONH—(CH$_2$)$_n$NR$_a$R$_b$.

Preferably at least one halogen atom must be present in R$_3$, R$_4$, R'$_3$ or R'$_4$ position, more preferably two halogens atoms (one halogen atom on each indole cycle) must be present and more preferably said halogen is Br.

It has been found by the inventors that compounds of formula V bearing at least one halogen atom on at least one of the two indole moieties present an antibacterial activity.

For compounds presenting an antibacterial activity as compounds of formula V for instance, the determination of the NorA efflux pump inhibition activity is possible only with specific techniques.

Therefore, such compounds are either only antibiotics or present both activities.

In an advantageous embodiment, the present invention relates to compounds defined above, of the following general formula VI:

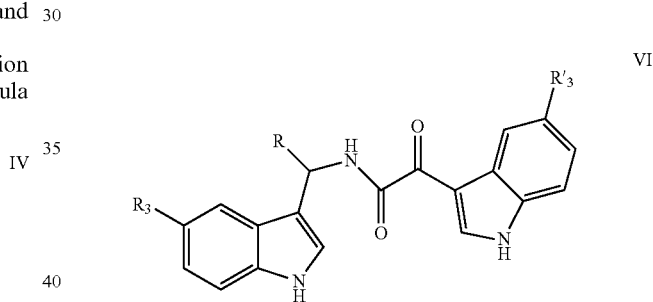

VI wherein:
R$_3$ and R'$_3$ represent independently from each other H, F, Cl, Br, I, at least one of R$_3$ and R'$_3$, represents F, Cl, Br, I, R represents a (C$_1$-C$_7$)-alkyl, CH$_2$NHCO$_2$—(C$_1$-C$_7$)-alkyl, CO$_2$H, CO$_2$—(C$_1$-C$_7$)-alkyl, CONH—(CH$_2$)$_n$OH, (CH$_2$)$_n$OH, CH$_2$NH(CH$_2$)$_n$—OH, CH$_2$NH(CH$_2$)$_n$—NR$_a$R$_b$, CONH—(CH$_2$)$_n$NR$_a$R$_b$.

In an advantageous embodiment, the present invention relates to compounds of formula VI defined above, wherein the compound of formula VI is selected from the group consisting of:

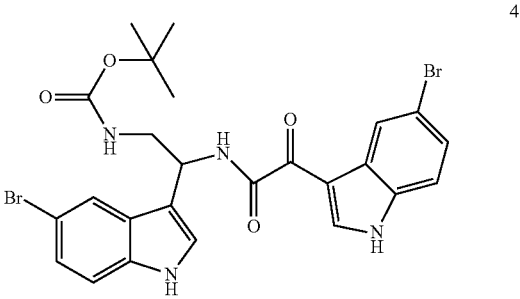

4

-continued

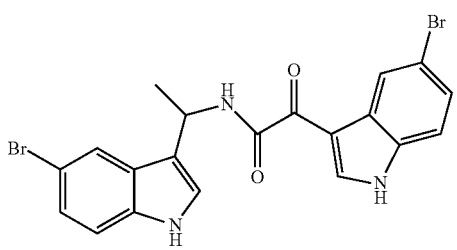

In an advantageous embodiment, the present invention relates to compounds defined above, of the following general formula VII:

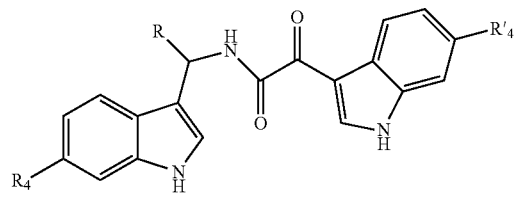

VII wherein:
R$_4$ and R'$_4$ represent independently from each other H, F, Cl, Br, I, at least one of R$_4$ and R'$_4$ represents F, Cl, Br, I,
R represents a (C$_1$-C$_7$)-alkyl, CH$_2$NHCO$_2$(C$_1$-C$_7$)-alkyl, CO$_2$H, CO$_2$—(C$_1$-C$_7$)-alkyl, CONH—(CH$_2$)$_n$OH, (CH$_2$)$_n$OH, CH$_2$NH(CH$_2$)$_n$—OH, CH$_2$NH(CH$_2$)$_n$—NR$_a$R$_b$, CONH—(CH$_2$)$_n$NR$_a$R$_b$.

In an advantageous embodiment, the present invention relates to compounds of formula VII defined above, having the following structure:

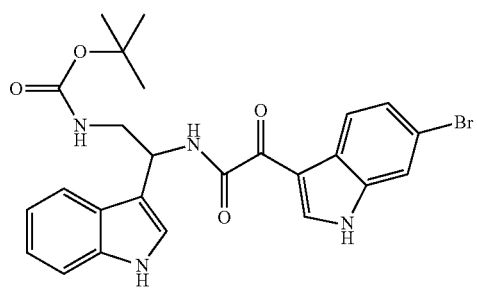

3

In an advantageous embodiment, the present invention relates to compounds defined above, of the following formula V-1

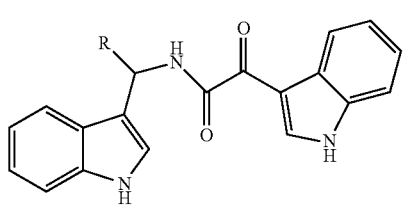

V-1 wherein:
R represents a (C$_1$-C$_7$)-alkyl, CH$_2$NHCO$_2$—(C$_1$-C$_7$)-alkyl, CO$_2$H, CO$_2$—(C$_1$-C$_7$)-alkyl, CONH—(CH$_2$)$_n$OH, (CH$_2$)$_n$OH, CH$_2$NH(CH$_2$)$_n$—OH, CH$_2$NH(CH$_2$)$_n$—NR$_a$R$_b$, CONH—(CH$_2$)$_n$NR$_a$R$_b$.

In an advantageous embodiment, the present invention relates to compounds of formula V-1 defined above, having the following structure:

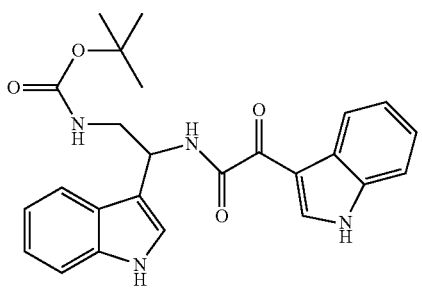

2

It has been found by the inventors that compounds of formula V-1 bearing no halogen atom on the two indole moieties present no antibacterial activity but present a NorA efflux pump inhibition activity.

One of the advantages of the compounds of the invention having a NorA efflux pump inhibition activity is the possibility of said compounds to reverse the resistance of a bacterial strain that became resistant to a classical antibiotic if they are administered with said classical antibiotic provided that classical antibiotic and compounds of the invention belong to different families of antibiotics.

In an advantageous embodiment, the present invention relates to compounds defined above, of the following general formula VIII:

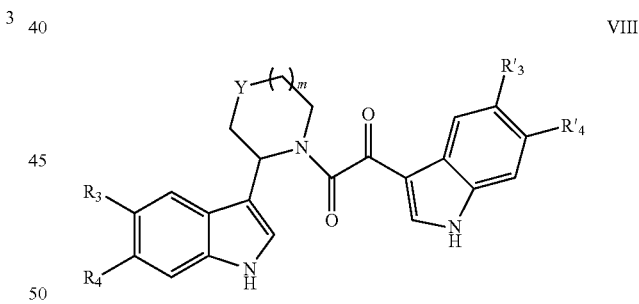

VIII wherein:
Y═N—R$_8$, R$_8$ being NBoc or NH,
Y═CH$_2$, CH—R$_8$, R$_8$ being as defined above,
R$_3$, R$_4$, R'$_3$ and R'$_4$ represent independently from each other H, F, Cl, Br, I,
m=0 or 1.

It has been found by the inventors that compounds of formula VIII do not need the presence of at least one halogen atom on at least one of the two indole moieties to show an antibacterial activity or a NorA efflux pump inhibition activity.

For compounds of formula VIII presenting an antibacterial activity, the determination of the NorA efflux pump inhibition activity is possible only with specific techniques.

Therefore, such compounds are either only antibiotics or present both activities.

In an advantageous embodiment, the present invention relates to compounds of formula VIII defined above, having the following structures:

6a
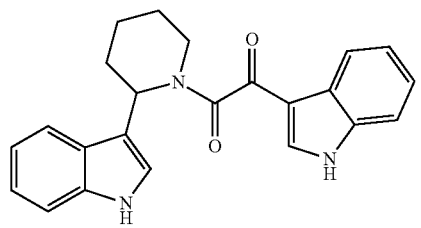

6d
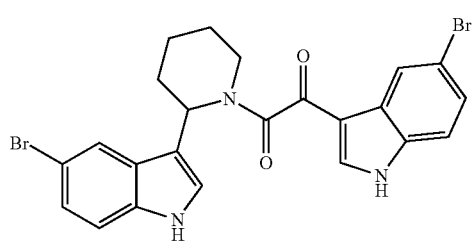

6c
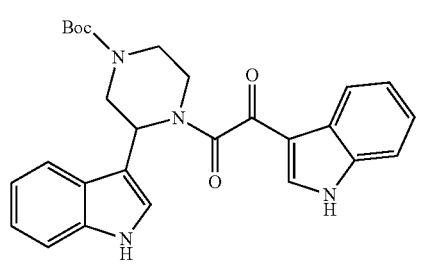

6f
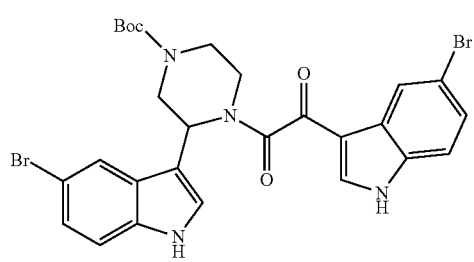

6b
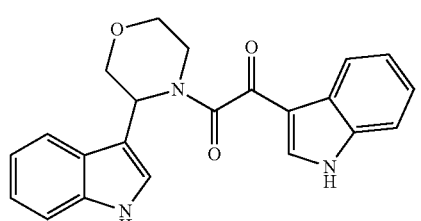

6e
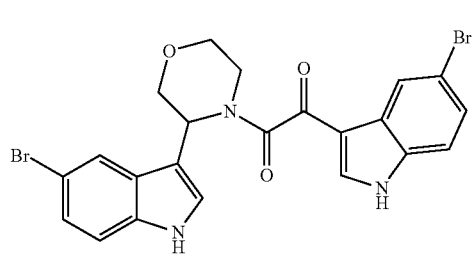

7
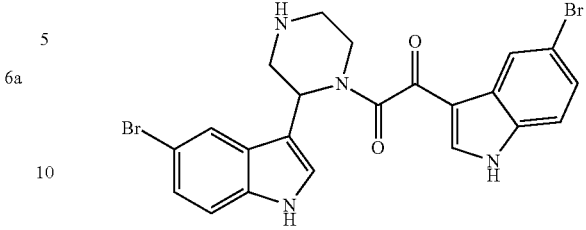

In an advantageous embodiment, the present invention relates to compounds defined above, of the following general formula VIII-1:

VIII-1
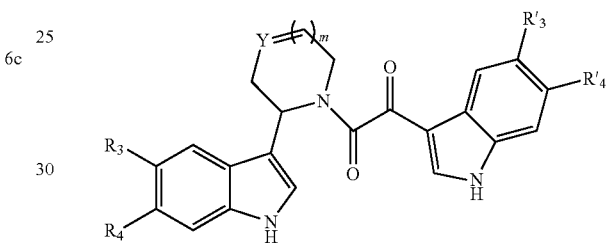

wherein:
Y=CH, C—$R_8$, $R_8$ being as defined above,
$R_3$, $R_4$, $R'_3$ and $R'_4$ represent independently from each other H, F, Cl, Br, I,
m=1.

In another aspect, the present invention relates to a pharmaceutical composition comprising a compound of formula I, in association with a pharmaceutically acceptable vehicle.

The expression "pharmaceutically acceptable vehicle" denotes in particular cellulose, starch, benzyl alcohol, polyethylene glycol, gelatin, lactose, polysorbate, magnesium or calcium stearate, xanthan gum, guar, alginate, colloidal silica.

The compositions according to the invention can be used by oral, parenteral, topic, or rectal route or in aerosols.

As solid compositions for oral administration, tablets, pills, gelatin capsules, powders or granules can be used. In these compositions, the active ingredient according to the invention is mixed with one or more inert diluents or adjuvants, such as saccharose, lactose or starch. These compositions can comprise substances other than the diluents, for example a lubricant such as magnesium stearate or a coating intended for controlled release.

As liquid compositions for oral administration, pharmaceutically acceptable solutions, suspensions, emulsions, syrups and elixirs containing inert diluents such as water or paraffin oil can be used. These compositions can also comprise substances other than the diluents, for example wetting products, sweeteners or flavourings.

The compositions for parenteral administration can be sterile solutions or emulsions. As solvent or vehicle, water, propylene glycol, a polyethylene glycol, vegetable oils, in particular olive oil, injectable organic esters, for example ethyl oleate can be used. These compositions can also contain adjuvants, in particular wetting agents, isotoning agents, emulsifiers, dispersants and stabilizers.

The sterilization can be carried out in several ways, for example using a bacteriological filter, by irradiation or by heating. They can also be prepared in the form of sterile solid compositions which can be dissolved at the moment of use in sterile water or any other injectable sterile medium.

The compositions for topical administration can be for example creams, ointments, lotions or aerosols.

The compositions for rectal administration are suppositories or rectal capsules, which, in addition to the active ingredient, contain excipients such as cocoa butter, semi-synthetic glycerides or polyethylene glycols.

The compositions can also be aerosols.

For use in the form of liquid aerosols, the compositions can be stable sterile solutions or solid compositions dissolved at the moment of use in pyrogen-free sterile water, in serum or any other pharmaceutically acceptable vehicle. For use in the form of dry aerosols intended to be directly inhaled, the active ingredient is finely divided and combined with a diluent or hydrosoluble solid vehicle, for example dextran, mannitol or lactose.

In an advantageous embodiment, the present invention relates to a pharmaceutical composition defined above, administrable by oral route at a dose comprised from about 10 mg/kg to about 200 mg/kg.

In an advantageous embodiment, the present invention relates to a pharmaceutical composition defined above, under a form liable to be administrable by oral route at a dose comprised from 100 mg to 1,500 mg, in particular from 100 mg to 1,000 mg, in particular from 100 to 500 mg.

Said pharmaceutical composition can be administered 2 or 3 times per day.

In an advantageous embodiment, the present invention relates to a pharmaceutical composition defined above, administrable by intraveinous route at a dose comprised from about 5 µg/kg to about 50 mg/kg.

In an advantageous embodiment, the present invention relates to a pharmaceutical composition defined above, under a form liable to be administrable by intraveinous route at a dose comprised from 0.1 mg to 1000 mg, in particular from 10 mg to 1,000 mg, in particular from 10 to 500 mg, in particular from 10 to 100 mg.

Said pharmaceutical composition can be administered 2 or 3 times per day.

In an advantageous embodiment, the present invention relates to a pharmaceutical composition defined above, comprising a compound of the formula V.

In an advantageous embodiment, the present invention relates to a pharmaceutical composition defined above, comprising a compound of the formula VI, such as compounds 4 or 5.

In an advantageous embodiment, the present invention relates to a pharmaceutical composition defined above, comprising a compound of the formula VII, such as compound 3.

In an advantageous embodiment, the present invention relates to a pharmaceutical composition defined above, comprising a compound of the formula V-1, such as compound 2.

In an advantageous embodiment, the present invention relates to a pharmaceutical composition defined above, comprising a compound of the formula VIII, such as compounds 6a, 6b, 6c, 6d, 6e, 6f or 7.

In an advantageous embodiment, the present invention relates to a pharmaceutical composition defined above, comprising further:

at least one antibiotic compound, in particular from the fluoroquinolones family, such as ciprofloxacin, norfloxacin, pefloxacin, enofloxacin, ofloxacin, levofloxacin or moxifloxacin, said pharmaceutical composition being used for simultaneous or separate use or use spread over time intended for the treatment of pathologies associated with bacterial infections for which a resistance to the antibiotic, in particular from the fluoroquinolones family exists.

Said antibiotic compound must be from a different family of the one of the compounds of the invention.

In this embodiment, if a compound of the invention is a NorA efflux pump inhibitor, administration of said compound with an antibiotic for which the bacterium is resistant allows to restore the antibiotic activity against bacteria that became resistant to said antibiotic.

If the compound of the invention presents only an antibacterial activity, administration of said compound with another antibiotic allows having a broader spectrum or increased activity.

EXAMPLES

Experimental Part—Chemistry

Scheme 1

Synthesis of 2-(1H-indol-3-yl)-2-oxoacetyl chlorides (8a-1)

Scheme 2

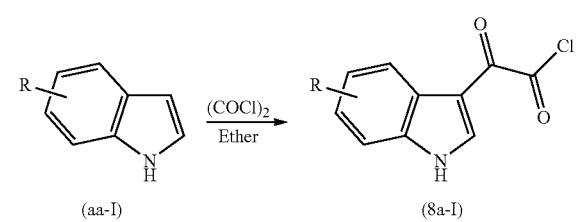

(aa-I)     (8a-I)

Synthesis of indolic β-amino N-hydroxylamines (Xa-1)
Scheme 3
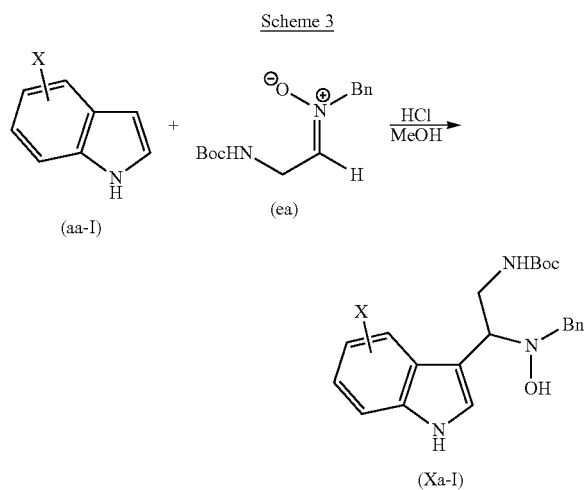
Synthesis of indolic amines (1a-1)
Scheme 4
Path A
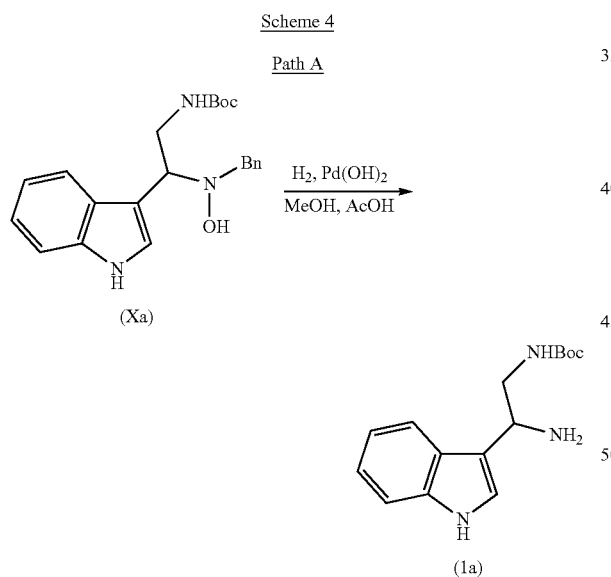
Path B
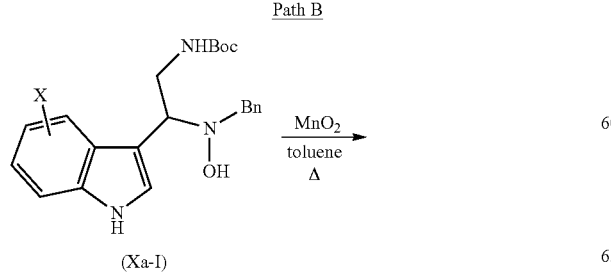
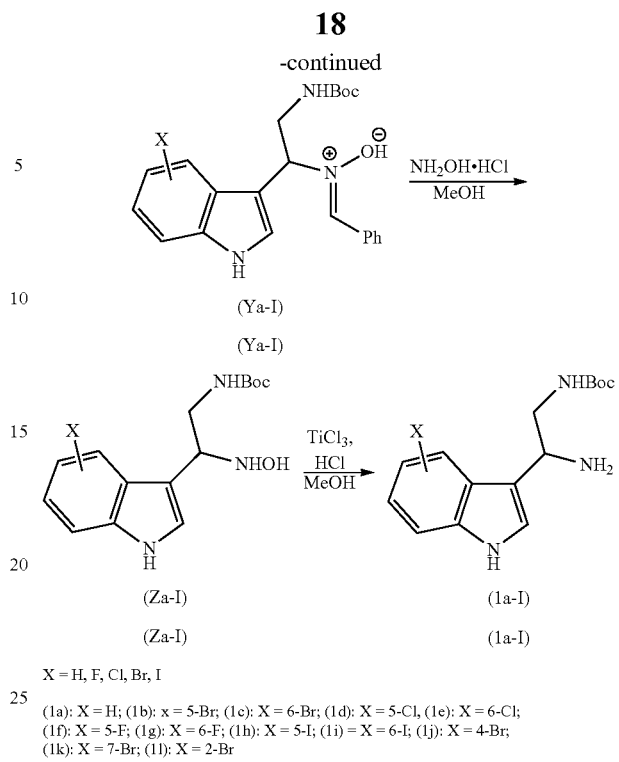
X = H, F, Cl, Br, I
(1a): X = H; (1b): x = 5-Br; (1c): X = 6-Br; (1d): X = 5-Cl; (1e): X = 6-Cl; (1f): X = 5-F; (1g): X = 6-F; (1h): X = 5-I; (1i) = X = 6-I; (1j): X = 4-Br; (1k): X = 7-Br; (1l): X = 2-Br
Synthesis of bis-indoles 2-4
Scheme 5
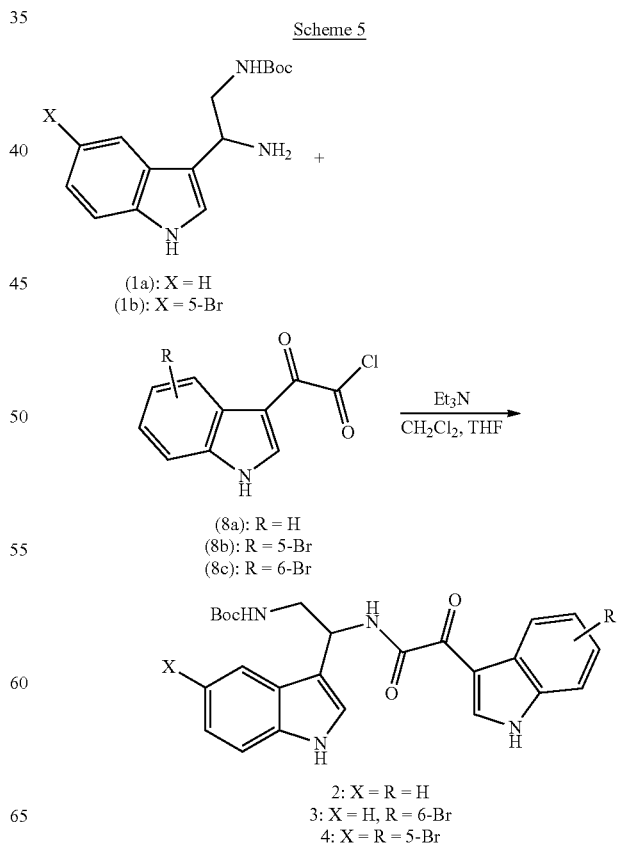
2: X = R = H
3: X = H, R = 6-Br
4: X = R = 5-Br

Synthesis of bis-indole 5
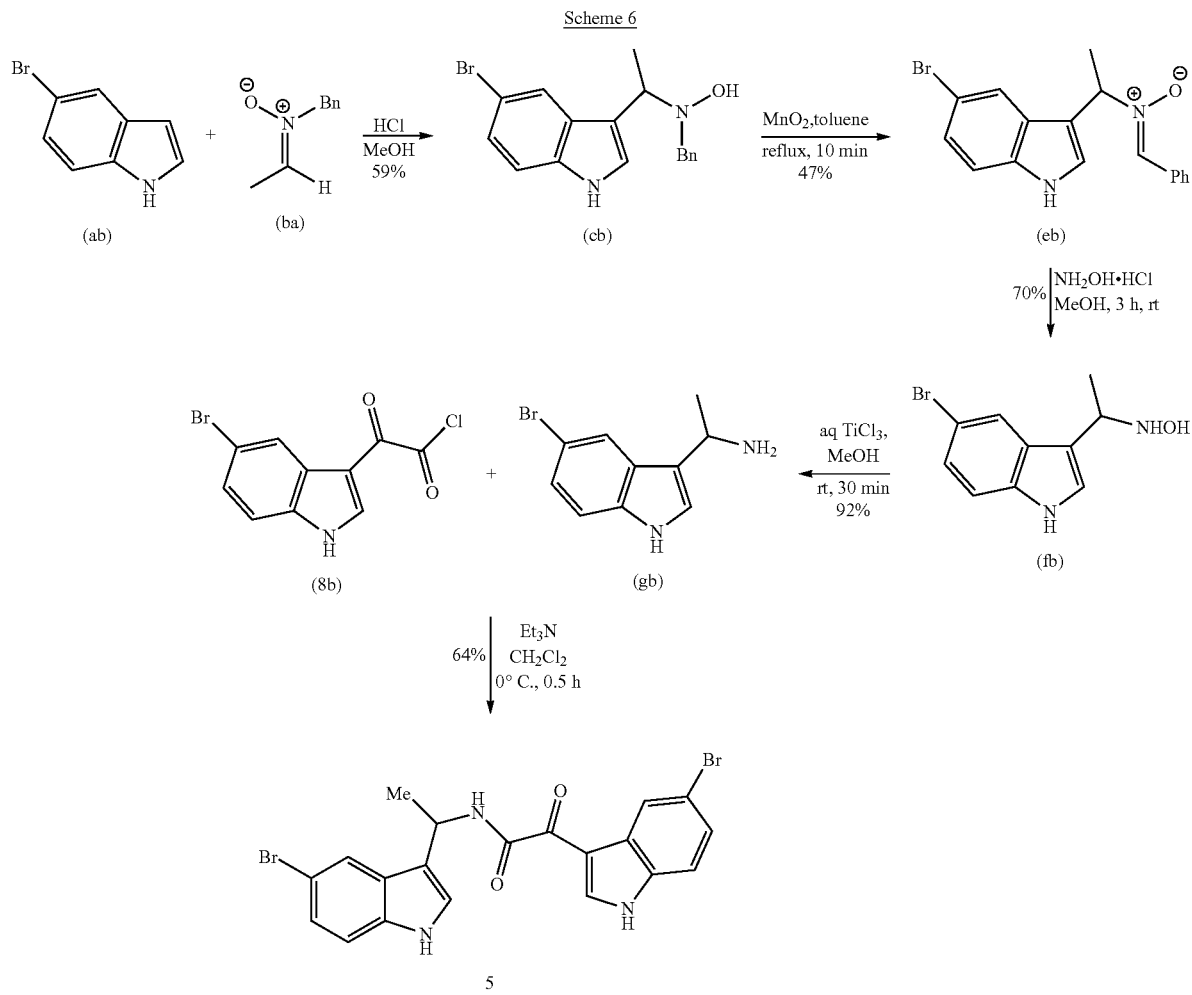
Synthesis of indolic amine (gb)
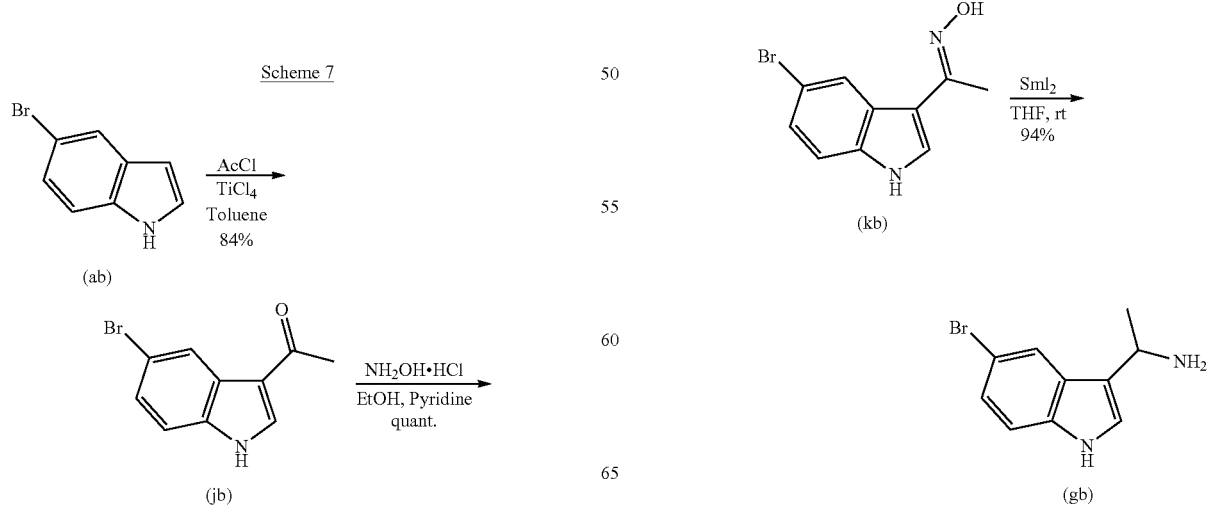

Comparative Examples
Compounds 12, 12a, 13 and 14
Scheme 8
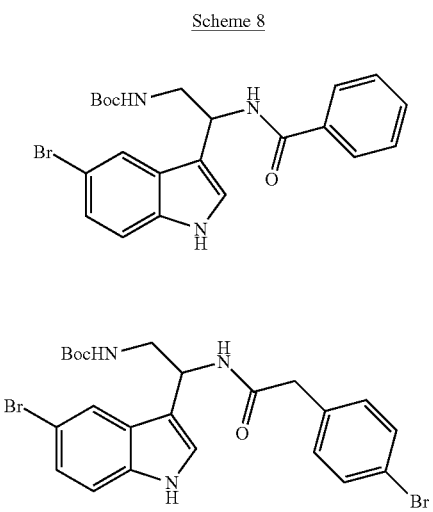
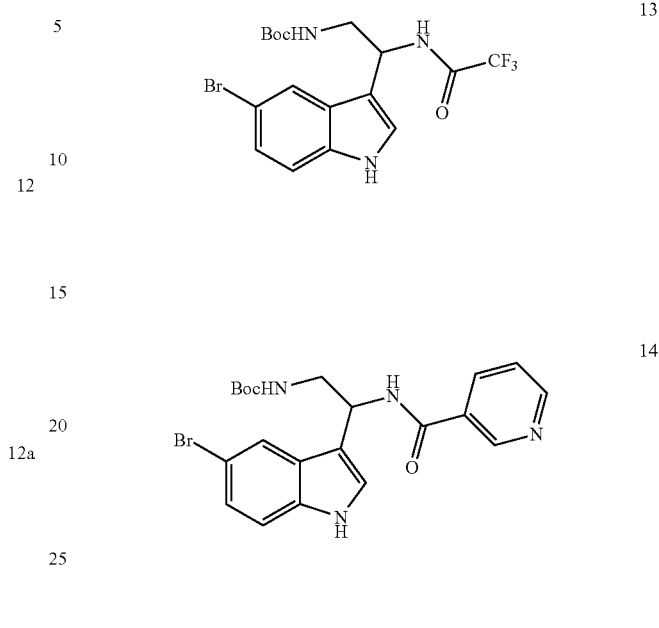
Synthesis of bis-indoles 6a-f and 7
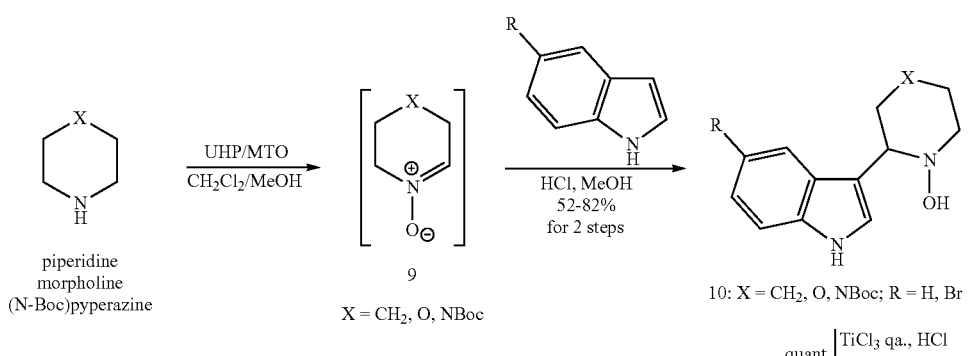
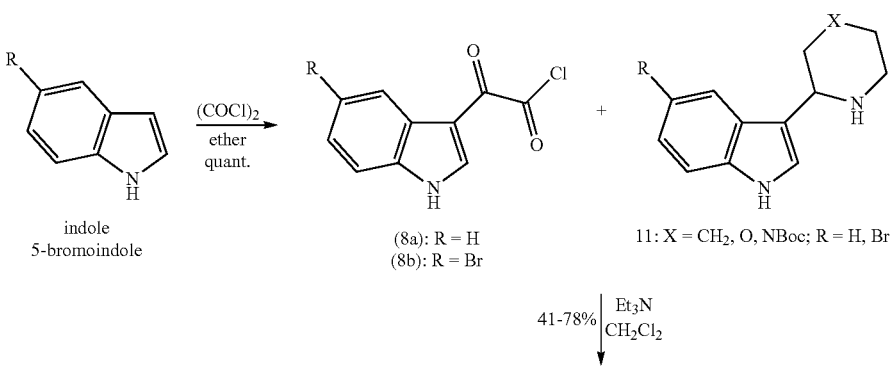

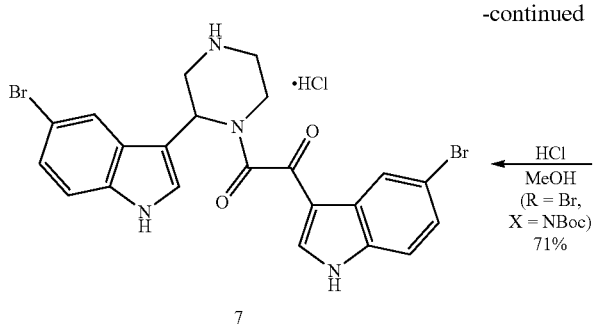

7

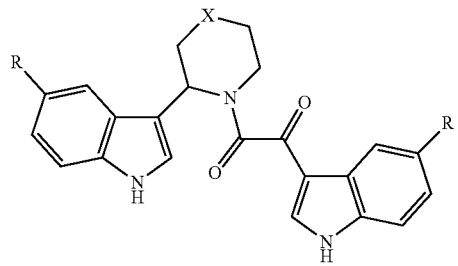

6a: X = CH₂; R = H
6b: X = O; R = H
6c: X = NBoc; R = H
6d: X = CH₂; R = Br
6e: X = O; R = Br
6f: X = NBoc; R = Br

HCl
MeOH
(R = Br,
X = NBoc)
71%

Compounds 9, 10 and 11

9a: X=CH₂; 9b: X=O; 9c: X=NBoc
10a: X=CH₂ and R=H; 10b: X=O and R=H; 10c: X=NBoc and R=H
10d: X=CH₂ and R=Br; 10e: X=O and R=Br; 10f: X=NBoc and R=Br
11a: X=CH₂ and R=H; 11b: X=O and R=H; 11c: X=NBoc and R=H
11d: X=CH₂ and R=Br; 11e: X=O and R=Br; 11f: X=NBoc and R=Br Synthesis of bis-indolic keto-amide derivatives Example 1

Synthesis of 2-(1H-indol-3-yl)-2-oxoacetyl chlorides (8a-1)

The 2-(1H-indol-3-yl)-2-oxoacetyl chlorides (8a) and (8c) were prepared according the procedure described in the literature. See: X. Guinchard, Y. Vallée, J.-N. Denis, <<Total synthesis of marine sponge bis(indole) alkaloids of the topsentin class>>, J. Org. Chem. 2007, 72, 3972-3975; X. Guinchard, Y. Vallée, J.-N. Denis, <<Total syntheses of brominated marine sponge alkaloids>>, Org. Lett. 2007, 9, 3761-3764.

2-(1H-Indol-3-yl)-2-oxoacetyl chloride (8a)

Commercially available:
Sigma-Aldrich P O Box 14508 St. Louis, Mo. 63178 USA
or
Alfa Aesar A Johnson Matthey Company
Shore Road Port of Heysham Industrial Park Heysham, Lancashire, LA3 2XY United Kingdom Phone: 0800 801812
To a solution of indole (468 mg, 4.0 mmol) in anhydrous diethyl ether (10 mL) at 0° C., freshly distilled oxalyl chloride (0.418 mL, 609 mg, 4.8 mmol) was added dropwise. The reaction mixture was stirred at 0° C. for 1.5 h and then allowed to warm to room temperature during an additional hour. After evaporation under vacuum, the resulting solid was collected by filtration, triturated in cold anhydrous diethyl ether, washed twice with this solvent and dried under vacuum. The obtained yellow solid (8a) (764 mg, 3.68 mmol) was used without further purification. Yield: 92%.

2-(5-Bromo-1H-indol-3-yl)-2-oxoacetyl chloride (8b)

Commercially available:
ASW MedChem, Inc. 100 Jersey Ave Box C-10 New Brunswick, N.J. 08901 USA
Under argon, a dry flask was charged with 5-bromoindole (ab) (400 mg, 2.04 mmol) and dry diethyl ether (5 mL). This solution was cooled to 0° C. and freshly distilled oxalyl chloride (0.210 mL, 2.45 mmol) was added. The solution was turned rapidly yellow. After stirring for 1 h30 at 0° C., the crude mixture was evaporated under reduced pressure. The resulting yellow solid was triturated and washed with dry diethyl ether and dried under vacuum. The desired product (8b) (524 mg, 1.83 mmol) was obtained as a yellow solid and was used after its preparation. Yield: 90%.

2-(6-Bromo-1H-indol-3-yl)-2-oxoacetyl chloride (8c)

Commercially available:
ASW MedChem, Inc. 100 Jersey Ave Box C-10 New Brunswick, N.J. 08901 USA
Under argon, a dry flask was charged with 6-bromoindole (ac) (400 mg, 2.04 mmol) and dry diethyl ether (5 mL). This solution was cooled to 0° C. and freshly distilled oxalyl chloride (0.210 mL, 2.45 mmol) was added. The solution was turned rapidly yellow. After stirring for 1 h30 at 0° C., the crude mixture was evaporated under reduced pressure. The resulting yellow solid was triturated and washed with dry diethyl ether and dried under vacuum. The desired product (8c) (479 mg, 1.67 mmol) was obtained as a yellow solid. Yield: 82%.

2-(5-Chloro-1H-indol-3-yl)-2-oxoacetyl chloride (8d)

Commercially available:
ASW MedChem, Inc. 100 Jersey Ave Box C-10 New Brunswick, N.J. 08901 USA
The compound (8d) can be obtained from 5-chloroindole (ad) according to the procedure described in this patent.

2-(6-Chloro-1H-indol-3-yl)-2-oxoacetyl chloride (8e)

Commercially available:
ASW MedChem, Inc. 100 Jersey Ave Box C-10 New Brunswick, N.J. 08901 USA The compound (8e) can be obtained from 6-chloroindole (ae) according to the procedure described in this patent.

2-(5-Fluoro-1H-indol-3-yl)-2-oxoacetyl chloride (8f)

Commercially available:
ASW MedChem, Inc. 100 Jersey Ave Box C-10 New Brunswick, N.J. 08901 USA
The compound (8t) can be obtained from 5-fluoroindole (af) according to the procedure described in this patent.

2-(6-Fluoro-1H-indol-3-yl)-2-oxoacetyl chloride (8g)

Commercially available:
ASW MedChem, Inc. 100 Jersey Ave Box C-10 New Brunswick, N.J. 08901 USA
The compound (8g) can be obtained from 6-fluoroindole (ag) according to the procedure described in this patent.

2-(5-Iodo-1H-indol-3-yl)-2-oxoacetyl chloride (8h)

2-(6-Iodo-1H-indol-3-yl)-2-oxoacetyl chloride (8i)

2-(7-Bromo-1H-indol-3-yl)-2-oxoacetyl chloride (8k)

2-(2-Bromo-1H-indol-3-yl)-2-oxoacetyl chloride (8l)

The compounds (8h-i) and (k-1) can be obtained from indoles (ai-i) and (ak-l) according to the procedure described in this patent.

2-(4-Bromo-1H-indol-3-yl)-2-oxoacetyl chloride (8j)

Commercially available:
ASW MedChem, Inc. 100 Jersey Ave Box C-10 New Brunswick, N.J. 08901 USA
The compound (8j) can be obtained from 4-bromoindole (aj) according to the procedure described in this patent.

Example 2

Synthesis of halo-indolic N-hydroxylamines (Xa-1)

tert-Butyl 2-(benzyl(hydroxy)amino)-2-(1H-indol-3-yl)ethyl carbamate (Xa)

A cold solution of hydrochloric acid was prepared by reaction of 1.12 mL (1.25 g, 15.91 mmol) of freshly distilled acetyl chloride with 40 mL of dry methanol. This solution was stirred at 0° C. during 15 min and then was added a mixture of both indole (aa) (0.93 g, 7.95 mmol) and nitrone (ea) (2.1 g, 7.95 mmol) in 20 mL of methanol. The reaction was stirred at 0° C. during 1 hour to completion. A saturated aqueous solution of NaHCO$_3$ was then added. The mixture was extracted 3 times with CH$_2$Cl$_2$ and the collected organic layers were washed with brine and dried over anhydrous MgSO$_4$. The solvent was removed under vacuum. The crude product was purified by trituration with pentane. The product (1a) was obtained as a white solid (3.0 g, 7.87 mmol). Yield: 99%.
Mp: 145-146° C. IR (neat): 3416, 3341, 3329, 3090, 3060, 3031, 2978, 2932, 2875, 2839, 1693, 1680, 1514, 1505, 1497, 1455, 1434, 1393, 1367, 1280, 1167, 1100 cm$^{-1}$. $^1$H NMR (200 MHz, CDCl$_3$): δ=1.51 (s, 9H, C(CH$_3$)$_3$), 3.50-3.70 (m, 2H, CH$_2$N), 3.75 (ABq, J$_{AB}$=14.4 Hz, δ$_A$-δ$_B$=38.9 Hz, 2H, CH$_2$Ph), 4.14 (t, J=5.4 Hz, 1H, CHN), 4.88 (t, J=6.5 Hz, 1H, NHBoc), 6.56 (s, 1H, OH), 7.08-7.39 (m, 9H, H arom), 7.66 (d, J=7.5 Hz, 1H, H arom), 8.36 (s, 1H, NH indol) ppm. $^{13}$C NMR (75.5 MHz, CDCl$_3$): δ=28.5 (C(CH$_3$)$_3$), 43.7 (CH$_2$), 60.6 (CH$_2$), 63.8 (CHN), 79.7 (C(CH$_3$)$_3$), 111.2 (CH arom), 112.3 (C arom), 119.6 (CH arom), 119.7 (CH arom), 122.2 (CH arom), 123.4 (CH arom), 126.7 (CH arom), 127.2 (C arom), 128.0 (CH arom), 128.6 (CH arom), 136.0 (C arom), 139.0 (C arom), 157.7 (C=O) ppm. LRMS (DCI, NH$_3$+isobutane): m/z=382 [(M+H)$^+$]. Anal. calcd for C$_{22}$H$_{27}$N$_3$O$_3$: C, 69.27; H, 7.13; N, 11.02. Found: C, 69.23; H, 7.36; N, 10.77.

Synthesis of halo-indolic N-hydroxylamines (Xb-1)

General Procedure
A cold solution of hydrochloric acid was prepared by reaction of 0.143 mL (157 mg, 2.0 mmol) of freshly distilled acetyl chloride with 5 mL of dry methanol. This solution was stirred at 0° C. during 15 min and was added to a mixture of both nitrone (ea) (1.0 mmol) and indole (aa-1) (1.0 mmol) in 5 mL of dry methanol. The reaction mixture was stirred at 0° C. during 2 hours to completion. A saturated aqueous solution of NaHCO$_3$ was then added. The mixture was extracted with CH$_2$Cl$_2$ (3×10 mL) and the collected organic layers were washed with brine, dried over anhydrous Na$_2$SO$_4$, filtered and concentrated under vacuum. Purification of the resulting crude product by column chromatography using EtOAc-pentane (from 1/99 to 40/60) yielded pure product (Xb-1).

tert-Butyl 2-(benzyl(hydroxy)amino)-2-(5-bromo-1H-indol-3-yl)ethylcarbamate (Xb)

The compound (Xb) (385 mg, 0.837 mmol) was obtained from nitrone (ea) (264 mg, 1.0 mmol) and 5-bromoindole (ab) (196 mg, 1.0 mmol) as a white solid. Yield: 84%.
Mp: 170-171° C. IR (neat): 3420, 3339, 2980, 2931, 1690, 1518, 1453, 1363, 1167 cm$^{-1}$. $^1$H NMR (300 MHz, CDCl$_3$): δ=1.53 (s, 9H, C(CH$_3$)$_3$), 3.5-3.7 (m, 2H, CH$_2$N), 3.7 (ABq, J$_{AB}$=13.7 Hz, δ$_A$-δ$_B$=45.3 Hz, 2H, CH$_2$Ph), 4.03 (t, J=5.5 Hz, 1H, CHN), 4.87 (t, J=6.9 Hz, 1H, NHBoc), 6.72 (s, 1H, OH), 7.15-7.35 (m, 8H, H arom), 7.84 (s, 1H, H arom), 8.37 (s, 1H, NH indol) ppm. $^{13}$C NMR (75.5 MHz, CDCl$_3$): δ=28.4 (C(CH$_3$)$_3$), 44.0 (CH$_2$), 60.5 (CH$_2$Ph), 63.9 (CHN), 80.0 (C(CH$_3$)$_3$), 112.7 (CH arom), 113.1 (C arom), 122.6 (CH arom), 123.2 (C arom), 124.6 (CH arom), 125.1 (CH arom), 126.8 (CH arom), 128.1 (CH arom), 128.6 (CH arom), 128.8 (C arom), 134.6 (C arom), 138.7 (C arom), 157.8 (C=O) ppm. LRMS (DCI, NH$_3$+isobutane): m/z=460 and 462 [(M+H)$^+$]. Anal. calcd for C$_{22}$H$_{26}$N$_3$O$_3$Br: C, 57.40, H, 5.69, N, 9.13. Found: C, 57.07, H, 5.65, N, 9.22.

tert-Butyl 2-(benzyl(hydroxy)amino)-2-(6-bromo-1H-indol-3-yl)ethylcarbamate (Xc)

The compound (Xc) (400 mg, 0.87 mmol) was obtained from nitrone (ea) (264 mg, 1.0 mmol) and 6-bromoindole (ac) (196 mg, 1.0 mmol) as a white solid. Yield: 87%.
Mp: 150° C. IR (neat): 3418, 3328, 3031, 2980, 2932, 1687, 1615, 1516, 1455, 1395, 1366, 1336, 1288, 1251, 1166, 1050, 1029, 897, 866, 846, 803, 738, 701 cm$^{-1}$. $^1$H NMR (300 MHz, CDCl$_3$): δ=1.50 (s, 9H, C(CH$_3$)$_3$), 3.55-3.70 (m, 2H, CH$_2$N), 3.72 (ABq, J$_{AB}$=14.0 Hz, δ$_A$-δ$_B$=57.8 Hz, 2H, CH$_2$Ph), 4.07 (t, J=5.7 Hz, 1H, CHN), 4.78-4.91 (def. t, 1H, NHBoc), 6.52 (s, 1H, OH), 7.18-7.35 (m, 7H, H arom), 7.51-7.55 (m, 2H, H arom), 8.22 (s, 1H, NH indol) ppm. $^{13}$C NMR (75.5 MHz, CDCl$_3$): δ=28.4 (C(CH$_3$)$_3$), 43.9 (CH$_2$), 60.5 (CH$_2$), 63.2 (CHN), 79.9 (C(CH$_3$)$_3$), 112.2 (C arom), 114.2

(CH arom), 115.8 (CH arom), 120.9 (CH arom), 122.9 (CH arom), 124.1 (CH arom), 126.0 (C arom), 126.8 (CH arom), 128.1 (CH arom), 128.5 (CH arom), 136.7 (C arom), 138.8 (C arom), 157.7 (C=O) ppm. LRMS (DCI, NH$_3$+isobutane): m/z=460 and 462 [(M+H)$^+$]. Anal. calcd for $C_{22}H_{26}N_3O_3Br$: C, 57.40; H, 5.69; N, 9.13. Found: C, 57.09; H, 5.87; N, 9.05.

tert-Butyl 2-(benzyl(hydroxy)amino)-2-(5-chloro-1H-indol-3-yl)ethylcarbamate (Xd)

The compound (Xd) (360 mg, 0.867 mmol) was obtained from nitrone (ea) (264 mg, 1.0 mmol) and 5-chloroindole (ad) (152 mg, 1.0 mmol) as a white solid. Yield: 87%.

IR (neat): 3315, 2970, 1655, 1520, 1295, 1165, 910, 895, 790, 735, 695 cm$^{-1}$. $^1$H NMR (300 MHz, CDCl$_3$-CD$_3$OD): δ=1.48 (s, 9H), 3.58-3.63 (m, 2H), 3.60 (d, J=13.7 Hz, 1H), 3.81 (d, J=13.7 Hz, 1H), 4.07 (t, J=5.4 Hz, 1H), 5.37 (t, J=6.2 Hz, 1H), 7.11 (dd, J=2.0 and 8.6 Hz, 1H), 7.20-7.37 (m, 8H), 7.68 (br s, 1H) ppm. $^{13}$C NMR (75.5 MHz, CDCl$_3$-CD$_3$OD): δ=29.8 (3C), 45.3, 59.0, 63.7, 81.3, 113.9 (2C), 120.7, 123.5 (2C), 126.4 (2C), 126.8, 128.4, 129.5 (2C), 130.3, 136.4, 139.7, 158.0 ppm. LRMS (ESI): m/z (%)=438 (22) [(M+Na)$^+$], 416 (100) [(M+H)$^+$], 293 (18), 237 (89), 193 (16).

tert-Butyl 2-(benzyl(hydroxy)amino)-2-(6-chloro-1H-indol-3-yl)ethylcarbamate (Xe)

The compound (Xe) (340 mg, 0.819 mmol) was obtained from nitrone (ea) (264 mg, 1.0 mmol) and 6-chloroindole (ae) (152 mg, 1.0 mmol) as a white solid. Yield: 82%.

IR (neat): 3405, 3360, 2975, 2850, 1655, 1520, 1455, 1365, 1290, 1160, 1105, 905, 800, 735, 695 cm$^{-1}$. $^1$H NMR (300 MHz, CDCl$_3$): δ=1.50 (s, 9H), 3.54-3.63 (m, 2H), 3.62 (d, J=14.0 Hz, 1H), 3.80 (d, J=14.0 Hz, 1H), 4.07 (t, J=5.6 Hz, 1H), 4.92 (t, J=6.2 Hz, 1H), 6.52 (br s, 1H), 7.08 (dd, J=1.7 and 8.5 Hz, 1H), 7.18-7.26 (m, 6H), 7.33 (d, J=1.4 Hz, 1H), 7.55 (d, J=8.6 Hz, 1H), 8.45 (br s, 1H) ppm. $^{13}$C NMR (75.5 MHz, CDCl$_3$): δ=28.5 (3C), 43.7, 60.6, 64.7, 79.9, 111.2 (2C), 120.4 (2C), 120.5, 124.2, 125.7, 126.8, 128.1 (2C), 128.6, 136.3, 138.7, 157.7 ppm. LRMS (ESI): m/z (%)=438 (17) [(M+Na)$^+$], 416 (97) [(M+H)$^+$], 293 (17), 237 (100), 193 (9).

tert-Butyl 2-(benzyl(hydroxy)amino)-2-(5-fluoro-1H-indol-3-yl)ethylcarbamate (Xf)

The compound (Xf) (390 mg, 0.977 mmol) was obtained from nitrone (ea) (264 mg, 1.0 mmol) and 5-fluoroindole (af) (135 mg, 1.0 mmol) as a white solid. Yield: 98%.

IR (neat): 3410, 3300, 2975, 2890, 1655, 1540, 1490, 1455, 1290, 1165, 935, 845, 745, 695 cm$^{-1}$. $^1$H NMR (300 MHz, CD$_3$OD): δ=1.43 (s, 9H), 3.49-3.81 (m, 4H), 4.13 (t, J=5.4 Hz, 1H), 6.90 (dt, J=2.4 and 9.1 Hz, 1H), 7.20-7.40 (m, 8H) ppm. $^{13}$C NMR (75.5 MHz, CD$_3$OD): δ=28.8 (3C), 44.2, 60.9, 62.4, 78.2, 103.2 (d, J=24.8 Hz), 110.6 (d, J=26.4 Hz), 113.0 (d, J=9.4 Hz), 124.3, 127.3, 127.8, 129.0 (2C), 130.2 (2C), 132.9, 136.7, 140.3, 156.7, 159.3 (d, J=236.1 Hz). $^{19}$F NMR (282 MHz, CD$_3$OD): δ=124.2 (dt, J=4.8 and 9.8 Hz, 1F) ppm. LRMS (ESI): m/z (%)=422 (21) [(M+Na)$^+$], 400 (97) [(M+H)$^+$], 277 (17), 221 (100), 177 (20).

tert-Butyl 2-(benzyl(hydroxy)amino)-2-(6-fluoro-1H-indol-3-yl)ethylcarbamate (Xg)

The compound (Xg) (340 mg, 0.85 mmol) was obtained from nitrone (ea) (264 mg, 1.0 mmol) and 6-fluoroindole (ag) (135 mg, 1.0 mmol) as a white solid. Yield: 85%.

IR (neat): 3410, 3365, 2975, 2875, 1655, 1625, 1520, 1290, 1165, 1140, 1095, 910, 830, 800, 735, 695 cm-1. $^1$H NMR (300 MHz, CDCl$_3$): δ=1.50 (s, 9H), 3.54-3.63 (m, 2H), 3.62 (d, J=14.0 Hz, 1H), 3.83 (d, J=14.0 Hz, 1H), 4.08 (t, J=5.7 Hz, 1H), 4.92 (t, J=6.8 Hz, 1H), 6.50 (br s, 1H), 6.88 (dt, J=2.3 and 9.4 Hz, 1H), 7.02 (dd, J=2.0 and 9.6 Hz, 1H), 7.18-7.27 (m, 6H), 7.56 (dd, J=5.3 and 8.7 Hz, 1H), 8.42 (br s, 1H) ppm. $^{13}$C NMR (75.5 MHz, CDCl$_3$): δ=28.7 (3C), 44.0, 60.9, 64.0, 80.1, 97.7 (d, J=26.2 Hz), 108.7 (d, J=24.4 Hz), 120.7 (d, J=10.4 Hz), 123.9, 124.0, 127.1, 128.3 (2C), 128.8 (2C), 132.3, 136.3, 138.9, 158.7, 160.3 (d, J=238.1 Hz) ppm. $^{19}$F NMR (282 MHz, CDCl$_3$): δ=125.0 (dt, J=4.7 and 9.6 Hz, 1F) ppm. LRMS (ESI): m/z (%)=422 (58) [(M+Na)$^+$], 400 (94) [(M+H)$^+$], 277 (20), 221 (100), 173 (12).

tert-Butyl 2-(benzyl(hydroxy)amino)-2-(5-iodo-1H-indol-3-yl)ethylcarbamate (Xh)

The compound (Xh) (420 mg, 0.828 mmol) was obtained from nitrone (ea) (264 mg, 1.0 mmol) and 5-iodoindole (ah) (243 mg, 1.0 mmol) as a white solid. Yield: 83%.

IR (neat): 3315, 2960, 1660, 1525, 1455, 1390, 1365, 1295, 1165, 910, 880, 790, 740, 695 cm-1.

$^1$H NMR (300 MHz, CDCl$_3$-CD$_3$OD): δ=1.48 (s, 9H), 3.57-3.61 (m, 2H), 3.59 (d, J=14.0 Hz, 1H), 3.83 (d, J=14.0 Hz, 1H), 4.07 (t, J=5.8 Hz, 1H), 5.47 (br s, 1H), 7.18-7.30 (m, 7H), 7.41 (dd, J=1.6 and 8.5 Hz, 1H), 8.03 (s, 1H) ppm. $^{13}$C NMR (75.5 MHz, CDCl$_3$-CD$_3$OD): δ=29.9 (3C), 44.3, 59.1, 63.6, 84.2, 97.8, 115.1 (2C), 123.7, 124.5, 126.4, 126.8, 128.2, 129.6 (2C), 130.4, 131.5, 132.4, 134.9, 138.2, 157.5 ppm. LRMS (ESI): m/z (%)=530 (33) [(M+Na)$^+$], 508 (100) [(M+H)$^+$], 329 (63).

tert-Butyl 2-(benzyl(hydroxy)amino)-2-(6-iodo-1H-indol-3-yl)ethylcarbamate (Xi)

The compound (Xi) can be obtained from nitrone (ea) and 6-iodoindole (ai) according to the procedure described in this patent.

tert-Butyl 2-(benzyl(hydroxy)amino)-2-(4-bromo-1H-indol-3-yl)ethylcarbamate (Xj)

The compound (Xj) (370 mg, 0.806 mmol) was obtained from nitrone (ea) (264 mg, 1.0 mmol) and 4-bromoindole (aj) (196 mg, 1.0 mmol) as a white solid. Yield: 81%.

IR (neat): 3375, 3290, 2980, 2830, 1655, 1560, 1455, 1330, 1290, 1165, 1120, 910, 730, 695 cm-1. $^1$H NMR (300 MHz, CD$_3$OD): δ=1.43 (s, 9H), 3.51-3.69 (m, 2H), 3.69 (d, J=14.3 Hz, 1H), 3.88 (d, J=14.3 Hz, 1H), 5.29 (t, J=6.0 Hz, 1H), 7.00 (t, J=7.8 Hz, 1H), 7.19-7.31 (m, 6H), 7.42 (d, J=8.1 Hz, 1H), 7.60 (s, 1H) ppm. $^{13}$C NMR (75.5 MHz, CD$_3$OD): δ=28.9 (3C), 42.7, 62.2, 64.1, 80.2, 112.1, 114.3, 123.0, 125.1, 125.7, 126.6, 126.9, 127.3, 129.0 (2C), 130.0, 132.8, 135.8, 138.9, 156.4 ppm. LRMS (ESI): m/z (%)=482 (26) [(M+Na)$^+$], 460 (100) [(M+H)$^+$], 281 (37).

tert-Butyl 2-(benzyl(hydroxy)amino)-2-(7-bromo-1H-indol-3-yl)ethylcarbamate (Xk)

The compound (Xk) can be obtained from nitrone (ea) and 7-bromoindole (ak) according to the procedure described in this patent.

tert-Butyl 2-(benzyl(hydroxy)amino)-2-(2-bromo-1H-indol-3-yl)ethylcarbamate (Xl)

The compound (Xl) can be obtained from nitrone (ea) and 2-bromoindole (al) according to the procedure described in this patent.

Example 3

Synthesis of indolic nitrones (Ya-j)

General Procedure

A stirred solution of indolic N-hydroxylamine (Xa-1) (1 equivalent) in toluene was warmed to 100° C. Five equivalents of manganese dioxide were added. The resulting heterogeneous mixture was then stirred at this temperature during 5-10 min. It was then cooled at room temperature and filtered on celite. Resulted heterogeneous solution was concentrated under vacuum. The obtained crude extract was purified by column chromatography on silica gel (previously treated by 2.5% of triethylamine) using EtOAc-pentane (from 5/95 to 90/10) affording pure product (Ya-1).

(Z)-N-Benzylidene-2-(tert-butoxycarbonylamino)-1-(1H-indol-3-yl) ethanamine N-oxide (Ya)

The compound (Ya) (560 mg, 1.48 mmol) was obtained from indolic N-hydroxylamine (Xa) (724 mg, 1.9 mmol) and $MnO_2$ (827 mg, 9.5 mmol) as a beige foam. Yield: 78%.
Mp: 150° C. IR (neat): 3302, 3056, 2979, 2927, 1699, 1686, 1505, 1460, 1369, 1253, 1176 $cm^{-1}$. $^1H$ NMR (300 MHz, $CDCl_3$): δ=1.43 (s, 9H, $C(CH_3)_3$), 3.78-3.95 (m, 1H, 1H of $CH_2$), 3.95-4.10 (m, 1H, 1H of $CH_2$), 5.49 (t, J=5.9 Hz, 1H, CHN), 5.6-5.7 (br s, 1H, NHBoc), 7.11 (quint., J=7.1 Hz, 2H, H arom), 7.22 (d, J=2.0 Hz, 1H, H arom), 7.28 (d, J=4.8 Hz, 1H, H arom), 7.33-7.40 (m, 3H, H arom), 7.57 (s, 1H, H arom), 7.70 (d, J=7.0 Hz, 1H, H arom), 8.17-8.24 (m, 2H, H ortho of Ph), 8.92 (s, 1H, NH) ppm. $^{13}C$ NMR (75.5 MHz, $CDCl_3$): δ=28.3 (C($\underline{C}H_3$)$_3$), 42.9 ($CH_2$), 71.9 (CHN), 79.7 ($\underline{C}(CH_3)_3$), 109.8 (C arom), 111.6 (CH arom), 118.6 (CH arom), 120.1 (CH arom), 122.3 (CH arom), 124.1 (CH arom), 125.9 (C arom), 128.4 (CH arom), 128.8 (CH arom), 130.3 (C arom), 130.5 (CH arom), 134.9 (CH=N), 136.1 (C arom), 156.3 (C=O) ppm. LRMS (DCI, $NH_3$+isobutane): m/z=380 [$(M+H)^+$], 279, 259, 258. HRMS (ESI) calcd for $C_{22}H_{25}N_3O_3Na$: 402.1794. Found: 402.1797 [$(M+Na)^+$].

(Z)-N-Benzylidene-2-(tert-butoxycarbonylamino)-1-(5-bromo-1H-indol-3-yl) ethanamine N-oxide (Yb)

The compound (Yb) (365 mg, 0.797 mmol) was obtained from indolic N-hydroxylamine (Xb) (575 mg, 1.25 mmol) and $MnO_2$ (544 mg, 6.25 mmol) as a beige foam. Yield: 64%.
Mp: 128° C. IR (KBr): 3419, 3299, 3075, 2977, 2929, 1696, 1513, 1453, 1363, 1254, 1164, 887, 801 $cm^{-1}$. $^1H$ NMR (300 MHz, $CDCl_3$): δ=1.42 (s, 9H, $C(CH_3)_3$), 3.72-3.83 (m, 1H, 1H of $CH_2N$), 3.93-4.10 (m, 1H, 1H of $CH_2N$), 5.39 (br s, 1H, NHBoc), 5.54 (br s, 1H, CHN), 6.99 (d, J=8.6 Hz, 1H, H arom), 7.12 (dd, J=1.7 and 8.6 Hz, 1H, H arom), 7.16 (d, J=2.4 Hz, 1H, H arom), 7.30-7.45 (m, 3H, H arom), 7.61 (s, 1H, CH=N), 7.77 (d, J=1.6 Hz, 1H, H arom), 8.15-8.30 (m, 2H, H arom), 9.57 (br s, 1H, NH) ppm. $^{13}C$ NMR (75.5 MHz, $CDCl_3$): δ=28.5 (($\underline{C}H_3$)$_3$C), 43.0 ($CH_2N$), 71.6 (CHN), 80.0 (($CH_3$)$_3\underline{C}$), 109.3 (C arom), 113.3 (CH arom), 113.5 (C arom), 121.1 (CH arom), 125.3 (CH arom), 125.7 (CH arom), 127.8 (C arom), 128.7 (CH arom), 129.1 (CH arom), 130.2 (C arom), 131.0 (CH arom), 134.9 (C arom), 135.5 (CH=N), 156.5 (C=O) ppm. LRMS (DCI, $NH_3$+isobutane): m/z=458 and 460 [$(M+H)^+$], 298 and 300, 281 and 283. HRMS (ESI) calcd for $C_{22}H_{24}N_3O_3^{79}BrNa$: 480.0899. Found: 480.0901 [$(M+Na)^+$].

(Z)-N-benzylidene-2-(tert-butoxycarbonylamino)-1-(6-bromo-1H-indol-3-yl) ethanamine N-oxide (Yc)

The compound (Yc) (430 mg, 0.94 mmol) was obtained from indolic N-hydroxylamine (XC) (598 mg, 1.30 mmol) and $MnO_2$ (566 mg, 6.50 mmol) as a beige foam. Yield: 72%.
Mp: 186° C. IR (neat): 3276, 2979, 2934, 1699, 1505, 1460, 1369, 1253, 1169, 807, 691 $cm^{-1}$.
$^1H$ NMR (300 MHz, $CDCl_3$): δ=1.43 (s, 9H, $C(CH_3)_3$), 3.70-3.80 (m, 1H, 1H of $CH_2$), 3.80-4.10 (m, 1H, 1H of $CH_2$), 5.40 (br s, 1H, CHN), 5.50-5.55 (m, 1H, NHBoc), 7.11-7.18 (m, 2H, H arom), 7.31 (d, J=1.4 Hz, 1H, H arom), 7.37-7.43 (m, 3H, Ph), 7.53 (d, J=8.4 Hz, 1H, H arom), 7.60 (s, 1H, H arom), 8.15-8.25 (m, 2H, 2H ortho Ph), 9.37 (br s, 1H, NH) ppm. $^{13}C$ NMR (75.5 MHz, $CDCl_3$): δ=28.3 (C($\underline{C}H_3$)$_3$), 42.7 ($CH_2$), 71.6 (CHN), 79.9 ($\underline{C}(CH_3)_3$), 109.8 (C arom), 114.6 (CH arom), 115.8 (C arom), 119.8 (CH arom), 123.3 (CH arom), 128.6 (CH arom), 128.9 (CH arom), 130.0 (C arom), 130.9 (C arom), 135.5 (CH=N), 136.9 (C arom), 156.4 (C=O) ppm. LRMS (ESI): m/z=480 and 482 [$(M+Na)^+$], 458 and 460 [$(M+H)^+$], 281 and 283. HRMS: (ESI) calcd for $C_{22}H_{24}N_3O_3Na^{79}Br$: 480.0899. Found: 480.0891 [$(M+Na)^+$].

(Z)-N-Benzylidene-2-(tert-butoxycarbonylamino)-1-(5-chloro-1H-indol-3-yl) ethanamine N-oxide (Yd)

The compound (Yd) (190 mg, 0.459 mmol) was obtained from indolic N-hydroxylamine (Xd) (290 mg, 0.70 mmol) and $MnO_2$ (305 mg, 3.50 mmol) as a beige foam. Yield: 66%.
IR (neat): 3265, 2980, 1695, 1505, 1450, 1365, 1250, 1160, 1130, 895, 795, 750, 690 $cm^{-1}$. $^1H$ NMR (300 MHz, $CDCl_3$): δ=1.41 (s, 9H), 3.71-3.76 (m, 1H), 3.95-4.03 (m, 1H), 5.39-5.55 (m, 2H), 6.90-6.98 (m, 2H), 7.02-7.10 (m, 1H), 7.30-7.39 (m, 3H), 7.59-7.62 (m, 2H), 8.20-8.24 (m, 2H), 9.70 (br s, 1H, NH) ppm. $^{13}C$ NMR (75.5 MHz, $CDCl_3$): δ=28.2 (3C), 42.7, 71.5, 79.8, 108.9, 112.7, 117.8, 122.4, 125.6, 125.7, 126.9, 128.5 (2C), 128.9 (2C), 129.9, 130.8, 134.4, 135.3, 156.2 ppm. LRMS (ESI): m/z (%)=436 (40) [$(M+Na)^+$], 414 (34) [$(M+H)^+$], 293 (12), 237 (100), 193 (12).

(Z)-N-benzylidene-2-(tert-butoxycarbonylamino)-1-(6-chloro-1H-indol-3-yl) ethanamine N-oxide (Ye)

The compound (Ye) (205 mg, 0.496 mmol) was obtained from indolic N-hydroxylamine (Xe) (290 mg, 0.70 mmol) and $MnO_2$ (305 mg, 3.50 mmol) as a beige foam. Yield: 71%.
IR (neat): 3275, 2970, 1685, 1505, 1450, 1365, 1250, 1160, 1130, 905, 800, 750, 690 $cm^{-1}$. $^1H$ NMR (300 MHz, $CDCl_3$): δ=1.41 (s, 9H), 3.67-3.80 (m, 1H), 3.94-4.06 (m, 1H), 5.43-5.58 (m, 2H), 6.93-7.07 (m, 3H), 7.33-7.38 (m, 3H), 7.48-7.53 (m, 1H), 7.61 (s, 1H), 8.20-8.24 (m, 2H), 9.65 (br s, 1H, NH) ppm. $^{13}C$ NMR (75.5 MHz, $CDCl_3$): δ=28.2 (3C), 42.6, 71.7, 79.8, 109.3, 111.6, 119.2, 120.5, 124.4, 124.9, 127.9, 128.5 (2C), 128.9 (2C), 129.9, 130.8, 135.4, 136.4, 156.3 ppm. LRMS (ESI): m/z (%)=436 (81) [$(M+Na)^+$], 414 (33) [$(M+H)^+$], 293 (16), 237 (100), 193 (14).

(Z)-N-benzylidene-2-(tert-butoxycarbonylamino)-1-(5-fluoro-1H-indol-3-yl) ethanamine N-oxide (Yf)

Compound (Yf) (210 mg, 0.529 mmol) was obtained from N-hydroxylamine (Xf) (320 mg, 0.80 mmol) and $MnO_2$ (348 mg, 4.00 mmol) as a beige foam. Yield: 66%.

IR (neat): 3465, 3295, 3060, 2970, 1685, 1505, 1455, 1370, 1240, 1175, 1150, 1130, 940, 785, 695, 670 cm$^{-1}$. $^1$H NMR (300 MHz, CDCl$_3$): δ=1.44 (s, 9H), 3.78-3.87 (m, 1H), 3.98-4.07 (m, 1H), 5.22-5.29 (m, 1H), 5.52-5.57 (m, 1H), 6.88 (dt, J=2.5 and 9.1 Hz, 1H), 7.18 (dd, J=4.4 and 9.0 Hz, 1H), 7.34-7.42 (m, 5H), 8.22-8.25 (m, 2H), 8.86 (br s, 1H, NH). $^{13}$C NMR (75.5 MHz, CDCl$_3$-CD$_3$OD): δ=27.9 (3C), 42.2, 71.4, 79.6, 103.0 (d, J=23.1 Hz), 110.2 (d, J=26.3 Hz), 112.1 (d, J=9.6 Hz), 125.7, 128.2 (2C), 128.9 (2C), 129.6, 130.8, 132.4, 136.2, 156.7, 157.7 (d, J=234.7 Hz). $^{19}$F NMR (282 MHz, CDCl$_3$): δ=123.3 (dt, J=4.3 and 9.3 Hz, 1F) ppm. LRMS (ESI): m/z (%)=420 (47) [(M+Na)$^+$], 398 (28) [(M+H)$^+$], 277 (15), 221 (100), 177 (15).

(Z)-N-benzylidene-2-(tert-butoxycarbonylamino)-1-(6-fluoro-1H-indol-3-yl) ethanamine N-oxide (Yg)

Compound (Yg) (200 mg, 0.504 mmol) was obtained from indolic N-hydroxylamine (Xg) (280 mg, 0.70 mmol) and MnO$_2$ (305 mg, 3.50 mmol) as a beige foam. Yield: 72%.

IR (neat): 3370, 3160, 2985, 2910, 1685, 1530, 1455, 1320, 1270, 1135, 950, 835, 685, 675 cm$^{-1}$. $^1$H NMR (300 MHz, CDCl$_3$): δ=1.44 (s, 9H), 3.80-3.88 (m, 1H), 3.98-4.07 (m, 1H), 5.22-5.29 (m, 1H), 5.56-5.60 (m, 1H), 6.87 (dt, J=2.3 and 9.4 Hz, 1H), 6.95 (dd, J=2.1 and 9.4 Hz, 1H), 7.28 (d, J=2.3 Hz, 1H), 7.39-7.42 (m, 3H), 7.57 (s, 1H), 7.62-7.67 (m, 1H), 8.21-8.25 (m, 2H), 8.80 (br s, 1H, NH). $^{13}$C NMR (75.5 MHz, CDCl$_3$-CD$_3$OD): δ=27.6 (3C), 42.0, 71.4, 79.3, 97.3 (d, J=23.8 Hz), 108.0 (d, J=25.0 Hz), 108.7, 118.7 (d, J=8.7 Hz), 122.3, 124.2 (d, J=3.4 Hz), 128.1 (2C), 128.9 (2C), 129.5, 130.6, 135.9 (d, J=12.6 Hz), 136.4, 156.6, 159.5 (d, J=237.2 Hz). $^{19}$F NMR (282 MHz, CDCl$_3$): δ=120.4 (m, 1F) ppm. LRMS (ESI): m/z (%)=420 (100) [(M+Na)$^+$], 398 (12) ([M+H]$^+$), 331 (8), 277 (6), 221 (36), 177 (5).

(Z)-N-benzylidene-2-(tert-butoxycarbonylamino)-1-(5-iodo-1H-indol-3-yl)ethanamine N-oxide (Yh)

Compound (Yh) (240 mg, 0.475 mmol) was obtained from indolic N-hydroxylamine (Xh) (355 mg, 0.70 mmol) and MnO$_2$ (305 mg, 3.50 mmol) as a beige foam. Yield: 68%.

IR (neat): 3275, 2970, 2930, 1695, 1505, 1450, 1365, 1250, 1160, 880, 795, 750, 690 cm-1. $^1$H NMR (300 MHz, CDCl$_3$): δ=1.42 (s, 9H), 3.71-3.81 (m, 1H), 3.94-4.05 (m, 1H), 5.29-5.40 (m, 1H), 5.48-5.55 (m, 1H), 6.87 (d, J=9.5 Hz, 1H), 7.10 (d, J=2.3 Hz, 1H), 7.28 (dd, J=1.4 and 8.6 Hz, 1H), 7.36-7.41 (m, 3H), 7.61 (s, 1H), 7.97 (s, 1H), 8.21-8.25 (m, 2H), 9.50 (br.s, 1H) ppm. $^{13}$C NMR (75.5 MHz, CDCl$_3$): δ=28.3 (3C), 42.8, 71.3, 80.0, 83.7, 108.7, 113.6, 125.1, 127.1, 128.4, 128.6 (2C), 128.9 (2C), 130.0, 130.6, 130.8, 135.1, 135.3, 156.2 ppm. LRMS (ESI): m/z (%)=528 (100) [(M+Na)$^+$], 506 (40) [(M+H)$^+$], 439 (6), 329 (86).

(Z)-N-benzylidene-2-(tert-butoxycarbonylamino)-1-(6-iodo-1H-indol-3-yl)ethanamine N-oxide (Yi)

The compound (Yi) can be obtained from indolic N-hydroxylamine (Xi) according to the procedure described in this patent.

(Z)-N-benzylidene-2-(tert-butoxycarbonylamino)-1-(4-bromo-1H-indol-3-yl) ethanamine N-oxide (Yj)

(Z)-N-benzylidene-2-(tert-butoxycarbonylamino)-1-(7-bromo-1H-indol-3-yl) ethanamine N-oxide (Yk)

(Z)-N-benzylidene-2-(tert-butoxycarbonylamino)-1-(2-bromo-1H-indol-3-yl) ethanamine N-oxide (Yl)

The compounds (Yj), (Yk) and (Yl) can be obtained from indolic N-hydroxylamines (Xj), (Xk) and (Xl) respectively according to the procedure described in this patent.

Example 4

Synthesis of indolic N-hydroxylamines (Za-1)

General Procedure

To a stirred solution of one equivalent of indolic nitrone (Ya-1) in methanol, three equivalents of hydroxylamine hydrochloride were added. The resulting mixture was stirred during 1 hour at room temperature and then the solution was concentrated under vacuum. A saturated aqueous solution of NaHCO$_3$ was added. The mixture was then extracted with diethyl ether (3×10 mL) and the collected organic layers were washed with brine, dried over anhydrous Na$_2$SO$_4$, filtered, and concentrated under vacuum. The resulting crude mixture was purified by column chromatography using EtOAc-pentane (10/90-99/1) to afford the corresponding pure product (Za-1).

tert-Butyl 2-(1H-indol-3-yl)-2-(hydroxyamino)ethylcarbamate (Za)

Compound (Za) (265 mg, 0.91 mmol) was obtained from indolic nitrone (Ya) (531 mg, 1.40 mmol) and NH$_2$OH.HCl (292 mg, 4.20 mmol) as a beige foam. Yield: 65%.

$^1$H NMR (300 MHz, CDCl$_3$): δ=1.43 (s, 9H, C(CH$_3$)$_3$), 3.4-3.6 (m, 1H, H of CH$_2$), 3.6-3.8 (m, 1H, H of CH$_2$), 4.37 (t, J=5.2 Hz, 1H, CHN), 5.04 (br s, 1H, NHBoc), 7.00 (s, 1H, H indol), 7.09 (t, J=7.0 Hz, 1H, H indol), 7.15 (t, J=7.0 Hz, 1H, H indol), 7.29 (d, J=7.9 Hz, 1H, H indol), 7.58 (d, J=7.9 Hz, 1H, H indol), 8.66 (s, 1H, NH indol) ppm. $^{13}$C NMR (75.5 MHz, CDCl$_3$,): δ=28.4 (C(CH$_3$)$_3$), 42.5 (CH$_2$N), 58.5 (CHN), 79.7 (C(CH$_3$)$_3$), 111.4 (CH indol), 112.5 (C indol), 118.9 (CH indol), 119.6 (CH indol), 122.2 (CH indol), 122.8 (CH indol), 126.2 (C indol), 136.0 (C indol), 157.0 (C=O) ppm. LRMS (DCI, NH$_3$+isobutane): m/z=314 (M+Na)$^+$, 292 [(M+H)$^+$], 279, 203. HRMS: (ESI) calcd for C$_{15}$H$_{22}$N$_3$O$_3$ [(M+H)$^+$]: 292.1661. Found: 292.1661.

tert-Butyl 2-(5-bromo-1H-indol-3-yl)-2-(hydroxyamino)ethylcarbamate (Zb)

Compound (Zb) (145 mg, 0.39 mmol) was obtained from nitrone (Yb) (320 mg, 0.70 mmol) and NH$_2$OH.HCl (146 mg, 2.10 mmol) as a beige foam. Yield: 56%.

Mp: 87° C. IR (KBr): 3419, 3307, 2977, 2936, 1692, 1516, 1456, 1366, 1254, 1172, 805 cm$^{-1}$.

$^1$H NMR (300 MHz, CDCl$_3$,): δ=1.43 (s, 9H, (CH$_3$)$_3$C), 3.35-3.65 (m, 2H, CH$_2$N), 4.25 (t, J=5.4 Hz, 1H, CHN), 5.11 (br s, 1H, NHBoc), 6.98 (d, J=1.7 Hz, 1H, H indol), 7.12 (d, J=8.7 Hz, 1H, H indol), 7.19 (dd, J=1.7 and 8.7 Hz, 1H, H indol), 7.72 (s, 1H, H indol), 9.05 (s, 1H, NH indol) ppm. $^{13}$C NMR (75.5 MHz, CDCl$_3$): δ=28.3 ((CH$_3$)$_3$C), 42.5 (CH$_2$N), 58.6 (CHN), 79.9 ((CH$_3$)$_3$C), 112.4 (C indol), 112.8 (C indol), 112.9 (CH indol), 121.7 (CH indol), 124.0 (CH indol), 124.9 (CH indol), 128.0 (C indol), 134.7 (C indol), 157.1 (C=O) ppm. LRMS (DCI, $NH_3$+isobutane): m/z=370 and 372 [(M+H)$^+$], 298 and 300, 281 and 283. HRMS (ESI) calcd for $C_{15}H_{20}N_3O_3{}^{79}BrNa$ [(M+Na)$^+$]: 392.0586. Found: 392.0591.

tert-Butyl 2-(6-bromo-1H-indol-3-yl)-2-(hydroxyamino)ethylcarbamate (Zc)

Compound (Zc) (170 mg, 0.46 mmol) was obtained from nitrone (Yc) (366 mg, 0.80 mmol) and $NH_2OH·HCl$ (167 mg, 2.40 mmol) as a beige foam. Yield: 57%.

Mp: 80° C. IR (KBr): 3419, 3302, 2979, 2934, 1693, 1518, 1454, 1369, 1253, 911, 807, 736 cm$^{-1}$. $^1H$ NMR (300 MHz, $CDCl_3$): δ=1.44 (s, 9H, $C(CH_3)_3$), 3.35-3.55 (m, 1H, H of $CH_2N$), 3.55-3.75 (m, 1H, H of $CH_2N$), 4.35 (t, J=5.1 Hz, 1H, CHN), 4.96 (br s, 1H, NHBoc), 7.06 (s, 1H, OH), 7.17 (dd, J=1.4 and 8.6 Hz, 1H, H indol), 7.46 (s, 1H, H indol), 7.47 (d, J=7.4 Hz, 1H, H indol), 8.66 (br s, 1H, NH indol) ppm. $^{13}C$ NMR (75.5 MHz, $CDCl_3$): δ=28.4 ($C(CH_3)_3$), 42.4 ($CH_2N$), 58.5 (CHN), 80.0 ($\underline{C}(CH_3)_3$), 112.9 (C indol), 114.4 (CH indol), 115.7 (C indol), 120.3 (CH indol), 123.0 (CH indol), 123.4 (CH indol), 125.2 (C indol), 136.9 (C indol), 157.1 (C=O) ppm. LRMS (ESI): m/z=370 and 372 [(M+H)$^+$], 281 and 283. HRMS (ESI) calcd for $C_{15}H_{21}N_3O_3{}^{79}Br$ [(M+H)$^+$]: 370.0766. Found: 370.0768 and 372.0747.

tert-Butyl 2-(5-chloro-1H-indol-3-yl)-2-(hydroxyamino)ethylcarbamate (Zd)

Compound (Zd) (80 mg, 0.246 mmol) was obtained from indolic nitrone (Yd) (165 mg, 0.40 mmol) and $NH_2OH·HCl$ (83 mg, 1.20 mmol) as a beige foam. Yield: 62%.

IR (neat): 3410, 3290, 2975, 2925, 1685, 1515, 1455, 1365, 1250, 1160, 895, 860, 795 cm$^{-1}$. $^1H$ NMR (300 MHz, $CDCl_3$): δ=1.44 (s, 9H), 3.40-3.45 (m, 1H), 3.56-3.70 (m, 1H), 4.29 (t, J=5.3 Hz, 1H), 5.03 (br s, 1H), 7.05-7.10 (m, 2H), 7.20 (d, J=9.0 Hz, 1H), 7.59 (s, 1H), 8.84 (br s, 1H) ppm. $^{13}C$ NMR (75.5 MHz, $CDCl_3$): δ=28.3 (3C), 42.5, 58.7, 79.9, 112.4, 118.7, 122.5, 124.1, 125.3, 127.3, 134.5 (2C), 157.1 ppm. LRMS (ESI): m/z (%)=348 (14) [(M+Na)$^+$], 326 (16) [(M+H)$^+$], 237 (100), 193 (12).

tert-Butyl 2-(6-chloro-1H-indol-3-yl)-2-(hydroxyamino)ethylcarbamate (Ze)

Compound (Ze) (100 mg, 0.308 mmol) was obtained from nitrone (Ye) (165 mg, 0.40 mmol) and $NH_2OH·HCl$ (83 mg, 1.20 mmol) as a beige foam. Yield: 77%.

IR (neat): 3415, 3280, 2975, 2925, 1685, 1510, 1455, 1365, 1250, 1160, 905, 800 cm$^{-1}$. $^1H$ NMR (300 MHz, $CDCl_3$): δ=1.43 (s, 9H), 3.40-3.62 (m, 2H), 4.30 (t, J=5.4 Hz, 1H), 5.06 (br s, 1H), 6.98-7.03 (m, 2H), 7.24-7.26 (m, 1H), 7.45 (d, J=9.0 Hz, 1H), 8.87 (br s, 1H) ppm. $^{13}C$ NMR (75.5 MHz, $CDCl_3$): δ=28.3 (3C), 42.4, 58.5, 79.9, 111.3, 119.8, 120.3, 123.3, 124.8, 128.0, 136.4 (2C), 157.1 ppm. LRMS (ESI): m/z (%)=348 (18) [(M+Na)$^+$], 326 (14) [(M+H)$^+$], 301 (12), 237 (100), 193 (11).

tert-Butyl 2-(5-fluoro-1H-indol-3-yl)-2-(hydroxyamino)ethylcarbamate (Zf)

Compound (Zf) (80 mg, 0.259 mmol) was obtained from indolic nitrone (Yf) (179 mg, 0.45 mmol) and $NH_2OH·HCl$ (94 mg, 1.35 mmol) as a beige foam. Yield: 58%.

IR (neat): 3415, 3300, 2975, 2925, 1685, 1510, 1490, 1455, 1365, 1250, 1160, 935, 850, 795 cm$^{-1}$. $^1H$ NMR (300 MHz, $CDCl_3$): δ=1.42 (s, 9H), 3.43-3.50 (m, 1H), 3.55-3.68 (m, 1H), 4.28 (t, J=5.3 Hz, 1H), 5.04 (br s, 1H), 6.88 (dt, J=2.4 and 9.0 Hz, 1H), 7.07 (s, 1H), 7.19 (dd, J=4.4 and 8.8 Hz, 1H), 7.21-7.30 (m, 1H), 8.79 (br s, 1H) ppm. $^{13}C$ NMR (75.5 MHz, $CDCl_3$): δ=28.3 (3C), 42.4, 58.7, 79.9, 104.1 (d, J=23.2 Hz), 110.6 (d, J=26.5 Hz), 112.0 (d, J=9.2 Hz), 124.4, 126.6 (d, J=10.2 Hz), 132.6 (2C), 157.2, 157.8 (d, J=236.7 Hz) ppm. $^{19}F$ NMR (282 MHz, $CDCl_3$): δ=124.1 (m, 1F) ppm. LRMS (ESI): m/z (%)=332 (49) [(M+Na)$^+$], 310 (7) [(M+H)$^+$], 239 (44), 221 (100).

tert-Butyl 2-(6-fluoro-1H-indol-3-yl)-2-(hydroxyamino)ethylcarbamate (Zg)

Compound (Zg) (50 mg, 0.162 mmol) was obtained from indolic nitrone (Yg) (159 mg, 0.40 mmol) and $NH_2OH·HCl$ (83 mg, 1.20 mmol) as a beige foam. Yield: 40%.

IR (neat): 3415, 3290, 2975, 2920, 1685, 1500, 1455, 1365, 1250, 1160, 1140, 950, 800 cm$^{-1}$.

$^1H$ NMR (300 MHz, $CDCl_3$): δ=1.43 (s, 9H), 3.45-3.51 (m, 1H), 3.60-3.65 (m, 1H), 4.34 (t, J=5.3 Hz, 1H), 5.02 (br s, 1H), 6.83 (dt, J=2.3 and 9.6 Hz, 1H), 6.97 (dd, J=2.3 and 9.6 Hz, 1H), 7.03 (s, H), 7.49 (dd, J=5.3 and 8.7 Hz, 1H), 8.74 (br s, 1H) ppm. $^{13}C$ NMR (75.5 MHz, $CDCl_3$): δ=28.4 (3C), 42.4, 58.6, 79.9, 97.6 (d, J=26.2 Hz), 108.4 (d, J=24.5 Hz), 122.8, 122.9, 128.8 (d, J=12.2 Hz), 136.0, 136.1, 158.4, 160.0 (d, J=238.5 Hz) ppm. $^{19}F$ NMR (282 MHz, $CDCl_3$): δ=120.7 (m, 1F) ppm. LRMS (ESI): m/z (%)=332 (43) [(M+Na)$^+$], 310 (6) [(M+H)$^+$], 239 (100), 221 (75).

tert-Butyl 2-(5-iodo-1H-indol-3-yl)-2-(hydroxyamino)-ethylcarbamate (Zh)

Compound (Zh) (125 mg, 0.30 mmol) was obtained from nitrone (Yh) (202 mg, 0.40 mmol) and $NH_2OH·HCl$ (83 mg, 1.20 mmol) as a beige foam. Yield: 75%.

IR (neat): 3410, 3280, 2975, 2925, 1685, 1510, 1455, 1365, 1250, 1160, 795, 750 cm$^{-1}$. $^1H$ NMR (300 MHz, $CDCl_3$): δ=1.44 (s, 9H), 3.40-3.49 (m, 1H), 3.50-3.61 (m, 1H), 4.26 (t, J=5.2 Hz, 1H), 5.08 (br s, 1H), 6.95 (s, 1H), 7.04 (d, J=8.5 Hz, 1H), 7.35 (dd, J=1.4 and 8.5 Hz, 1H), 7.94 (s, 1H), 8.96 (br s, 1H) ppm. $^{13}C$ NMR (75.5 MHz, $CDCl_3$): δ=28.3 (3C), 42.5, 58.5, 79.9, 83.0, 112.1, 113.4, 123.5, 127.9, 128.8, 130.3, 135.1, 157.0 ppm. LRMS (ESI): m/z (%)=440 (18) [(M+Na)$^+$], 418 (56) [(M+H)$^+$], 376 (100).

tert-Butyl 2-(6-iodo-1H-indol-3-yl)-2-(hydroxyamino)-ethylcarbamate (Zi)

The compound (Zi) can be obtained from indolic N-hydroxylamine (Yi) according to the procedure described in this patent.

tert-Butyl 2-(4-bromo-1H-indol-3-yl)-2-(hydroxyamino)ethylcarbamate (Zj)

Compound (Zj) (75 mg, 0.202 mmol) was obtained from nitrone (Yj) (137 mg, 0.30 mmol) and $NH_2OH·HCl$ (63 mg, 0.90 mmol) as a beige foam. Yield: 68%.

IR (neat): 3415, 3275, 2975, 2925, 1685, 1510, 1365, 1335, 1250, 1160, 775, 735 cm$^{-1}$. $^1H$ NMR (300 MHz, $CDCl_3$): δ=1.43 (s, 9H), 3.57-3.75 (m, 2H), 5.06-5.16 (m, 2H), 6.93 (t, J=7.8 Hz, 1H), 7.18-7.25 (m, 3H), 9.18 (br s, 1H) ppm. $^{13}C$ NMR (75.5 MHz, $CDCl_3$): δ=28.3 (3C), 42.2, 57.2, 79.8 (C), 110.9, 112.9, 113.3, 122.8, 124.2, 124.4, 124.5, 137.5, 157.4 ppm. LRMS (ESI): m/z (%)=384 (28) [(M+Na)+], 372 (14) [(M+H)+], 360 (11), 328 (100), 293 (23).

tert-Butyl 2-(7-bromo-1H-indol-3-yl)-2-(hydroxyamino)ethylcarbamate (Zk)

tert-Butyl 2-(2-bromo-1H-indol-3-yl)-2-(hydroxyamino)ethylcarbamate (Zi)

The compounds (Zk) and (Zl) can be obtained from indolic N-hydroxylamines (Yk) and (Yl) respectively according to the procedure described in this patent.

Example 5

Synthesis of indolic amines (1a-1)

5.1. Synthesis of indolic amines (1a-d)

tert-Butyl 2-amino-2-(1H-indol-3-yl)ethylcarbamate (1a)

Synthesis from primary hydroxylamine (Za)

To a stirred solution of primary hydroxylamine (Za) (70 mg (0.24 mmol) in 1 mL of methanol was added 0.51 mL of a 15% aqueous solution of titanium trichloride (74 mg, 0.48 mmol). The resulting mixture was stirred at room temperature during 30 min. A large excess of an aqueous 20% solution of sodium hydroxide saturated with sodium chloride was added. Methanol was removed under vacuum and the crude mixture was extracted three times with EtOAc. The combined organic layers were washed with water and brine, dried over anhydrous $MgSO_4$ and evaporated. The residue was purified by column chromatography on silica gel (Eluent: EtOAc). The product (1a) was obtained as a white solid (64 mg, 0.23 mmol). Yield: 97%.

Synthesis from indolic N-hydroxylamine (Xa)

For this procedure, see: Xavier Guinchard, "thèse de l'Université Joseph Fourier, Grenoble 1", 2006.
To a stirred solution of indolic N-hydroxylamine (Xa) (2.0 g, 5.25 mmol) in 93 mL of methanol and 3.5 mL of acetic acid was added 0.8 g of Pearlman's catalyst (Pd(OH)$_2$). Argon was replaced by hydrogen. The resulting mixture was then stirred at room temperature during 40 h. It was then filtered through celite. The resulting filtrate was treated by a 6N aqueous solution of sodium hydroxide. Methanol was then evaporated under vacuum. The resulting aqueous phase was extracted three times with EtOAc. Combined organics layers were washed with brine and dried over anhydrous $MgSO_4$. After the removal of the solvent, the residue was purified by column chromatography on silica gel (Eluent: EtOAc). The product (Za) was obtained as a white solid (1.31 g, 4.75 mmol). Yield: 90%.

Mp: 145-146° C. IR (neat): 3404, 3339, 3308, 3053, 2977, 2930, 1703, 1693, 1682, 1537, 1531, 1519, 1514, 1504, 1455, 1393, 1367, 1337, 1251, 1170 cm$^{-1}$. $^1$H NMR (300 MHz, CDCl$_3$): δ=1.44 (s, 9H, C(CH$_3$)$_3$), 1.76 (br s, 2H, NH$_2$), 3.39 (ddd, J=6.5, 7.0 and 13.0 Hz, 1H, 1H of CH$_2$N), 3.57 (ddd, J=5.5, 6.5 and 13.0 Hz, 1H, 1H of CH$_2$N), 4.41 (dd, J=5.5 and 7.0 Hz, 1H, CHN), 4.90 (br s, 1H, NHBoc), 7.12 (ddd, J=1.0, 7.5 and 7.5 Hz, 1H, H indol), 7.13 (s, 1H, H indol), 7.20 (ddd, J=1.0, 7.5 and 7.5 Hz, 1H, H indol), 7.37 (d, J=8.0 Hz, 1H, H indol), 7.71 (d, J=8.0 Hz, 1H, H indol), 8.30 (br s, 1H, NH) ppm. $^{13}$C NMR (75.5 MHz, CDCl$_3$): δ=28.4 (C(CH$_3$)$_3$), 47.5 (CH$_2$), 48.7 (CHN), 79.3 (C(CH$_3$)$_3$), 111.3 (CH indol), 118.6 (C indol), 119.3 (CH indol), 119.6 (CH indol), 121.0 (CH indol), 122.3 (CH indol), 125.9 (C indol), 136.6 (C indol), 156.2 (C=O) ppm. LRMS (DCI, NH$_3$+isobutane): m/z=276 [(M+H)+]. Anal. calcd for C$_{15}$H$_{21}$N$_3$O$_2$: C, 65.43; H, 7.69; N, 15.26. Found: C, 65.22; H, 7.69; N, 15.19.

tert-Butyl 2-amino-2-(5-bromo-1H-indol-3-yl)ethylcarbamate (1b)

To a stirred solution of primary hydroxylamine (Zb) (556 mg, 1.50 mmol) in 5 mL of methanol was added 3.53 mL of a 15% aqueous solution of titanium trichloride (509 mg, 3.3 mmol). The resulting mixture was stirred at room temperature during 30 min. A large excess of a 20% aqueous solution of sodium hydroxide saturated with sodium chloride was added. Methanol was removed under vacuum and the crude mixture was extracted three times with EtOAc. The combined organic layers were washed with water and brine, dried on anhydrous $MgSO_4$ and evaporated. The obtained residue was purified by column chromatography on silica gel (Eluent: EtOAc). The product (Zb) was obtained as a white solid (438 mg, 1.24 mmol). Yield: 83%.

Mp: 151° C. IR (film): 3423, 3296, 2977, 2925, 1692, 1508, 1456, 1363, 1280, 1250, 1164 cm$^{-1}$. $^1$H NMR (300 MHz, MeOD): δ=1.41 (s, 9H, C(CH$_3$)$_3$), 3.20-3.50 (m, 2H, CH$_2$N), 4.28 (dd, J=5.9 and 7.3 Hz, 1H, CHN), 7.18 (dd, J=1.8 and 8.6 Hz, 1H, H indol), 7.26 (d, J=8.5 Hz, 1H, H indol), 7.26 (s, 1H, H indol), 7.81 (d, J=1.5 Hz, 1H, H indol) ppm. $^{13}$C NMR (75.5 MHz, MeOD): δ=28.7 (C(CH$_3$)$_3$), 48.9 (CH$_2$), 49.4 (CHN), 80.1 (C(CH$_3$)$_3$), 113.1 (C indol), 114.0 (CH indol), 117.6 (C indol), 122.3 (CH indol), 124.2 (CH indol), 125.3 (CH indol), 129.2 (C indol), 136.7 (C indol), 158.5 (C=O) ppm. LRMS (ESI): m/z=354 and 356 [(M+H)+]. HRMS (ESI) calcd for C$_{15}$H$_{21}$N$_3$O$_2$$^{79}$Br: 354.0817. Found: 354.0837 [(M+H)+].

tert-Butyl 2-amino-2-(6-bromo-1H-indol-3-yl)ethylcarbamate (1c)

To a stirred solution of 280 mg (0.756 mmol) of primary hydroxylamine (Zc) in 3 mL of methanol was added 1.78 mL of a 15% aqueous solution of titanium trichloride (257 mg, 1.66 mmol). The resulting mixture was stirred at room temperature during 30 min. A large excess of a 20% aqueous solution of sodium hydroxide saturated with sodium chloride was added. Methanol was removed under vacuum and the crude mixture was extracted three times by EtOAc. The combined organic layers were washed with water and brine, dried over anhydrous $MgSO_4$ and evaporated. The resulting residue was purified by column chromatography on silica gel (Eluent: EtOAc) to afford the product (1c) as a white solid (248 mg, 0.70 mmol). Yield: 92%.

Mp: 80° C. IR (neat): 3287, 2977, 2931, 1692, 1505, 1458, 1364, 1171, 803 cm$^{-1}$. $^1$H NMR (300 MHz, MeOD): δ=1.42 (s, 9H, C(CH$_3$)$_3$), 3.20-3.30 (m, 1H, CH of CH$_2$), 3.42-3.50 (m, 1H, H of CH$_2$), 4.31 (dd, J=5.5 and 7.9 Hz, 1H, CHN), 7.13 (dd, J=1.8 and 8.5 Hz, 1H, H indol), 7.24 (s, 1H, H indol), 7.51 (d, J=1.7 Hz, 1H, H indol), 7.58 (d, J=8.2 Hz, 1H, H indol) ppm.

$^{13}$C NMR (75.5 MHz, MeOD): δ=28.7 (C(CH$_3$)$_3$), 48.8 (CH$_2$), 49.6 (CHN), 80.2 (C(CH$_3$)$_3$), 115.2 (CH indol), 114.0 (C indol), 118.0 (C indol), 121.1 (CH indol), 123.0 (CH indol), 123.6 (CH indol), 126.4 (C indol), 139.0 (C indol), 158.5 (C=O) ppm. LRMS (ESI): m/z=354 and 356 [(M+H)+]. HRMS (ESI) calcd for C$_{15}$H$_{21}$N$_3$O$_2$$^{79}$Br: 354.0817. Found: 354.0812 [(M+H)+].

tert-Butyl 2-amino-2-(5-chloro-1H-indol-3-yl)ethyl-carbamate (1d)

To a stirred solution of indolic N-hydroxylamine (Zd) (326 mg, 1.0 mmol) in 5 mL of methanol was added 1.7 mL of 15% aqueous solution of titanium trichloride (339 mg, 2.2 mmol). The resulting mixture was stirred at room temperature during 30 min. A large excess of a 20% aqueous solution of sodium hydroxide saturated with NaCl was added. Methanol was then removed under vacuum and the crude mixture was extracted with EtOAc (3×20 mL). Combined organic layers were washed with $H_2O$ and brine, dried over anhydrous $Na_2SO_4$, filtered and concentrated under vacuum. Pure amine (1c) was obtained as a white solid (288 mg, 0.932 mmol). Yield: 93%.

$^1$H NMR (300 MHz, $CD_3OD$): δ=1.41 (s, 9H), 3.39-3.45 (m, 2H), 4.30-4.34 (m, 1H), 7.06 (d, J=7.8 Hz, 1H), 7.28-7.33 (m, 2H), 7.66 (s, 1H) ppm. $^{13}$C NMR (75.5 MHz, $CD_3OD$): δ=28.8 (3C), 48.7, 49.3, 80.2, 113.6, 117.2, 119.2, 122.8, 124.5, 125.7, 128.6, 136.5, 156.5 ppm. LRMS (ESI): m/z (%)=310 (13) [(M+H)$^+$], 237 (100) [(M $C_4H_9O+H$)$^+$].

5.2. Synthesis of amines (1e-l)

These compounds can be prepared according the method described in this patent.

tert-Butyl 2-amino-2-(6-chloro-1H-indol-3-yl)ethyl-carbamate (1e)

tert-Butyl 2-amino-2-(5-fluoro-1H-indol-3-yl)ethyl-carbamate (1f)

tert-Butyl 2-amino-2-(6-fluoro-1H-indol-3-yl)ethyl-carbamate (1g)

tert-Butyl 2-amino-2-(5-iodo-1H-indol-3-yl)ethylcarbamate (1h)

tert-Butyl 2-amino-2-(6-iodo-1H-indol-3-yl)ethylcarbamate (1i)

tert-Butyl 2-amino-2-(4-iodo-1H-indol-3-yl)ethylcarbamate (1j)

tert-Butyl 2-amino-2-(7-iodo-1H-indol-3-yl)ethylcarbamate (1k)

tert-Butyl 2-amino-2-(2-iodo-1H-indol-3-yl)ethylcarbamate (1l)

Example 6

Synthesis of α-keto-amides 2-4

The compounds 2-4 were prepared from the corresponding 2-(1H-indol-3-yl)-2-oxoacetyl chlorides (8a-c) and indolic primary amines (1a) and (1b) according the procedure described in the literature: X. Guinchard, Y. Vallée, J.-N. Denis, <<Total syntheses of brominated marine sponge alkaloids>>, *Org. Lett.* 2007, 9, 3761-3764.

tert-Butyl(2-(2-(1H-indol-3-yl)-2-oxoacetamido)-2-(1H-indol-3-yl)ethyl)carbamate 2

To a cooled solution of amine (1a) (200 mg, 0.73 mmol) at 0° C. in THF was added $Et_3N$ (73 mg, 0.73 mmol) and then the acid chloride (8a) (150 mg, 0.73 mmol). Reaction was stirred at 0° C. during two hours and then $H_2O$ was added. The resulting mixture was extracted twice with EtOAc. Combined organic layers were washed with brine and dried over anhydrous $MgSO_4$. After the removal of the solvents, the amide 2 was obtained as a yellow solid (317 mg, 0.71 mmol). Yield: 97%.

$^1$H NMR (300 MHz, $(CD_3)_2CO$): δ=1.39 (s, 9H, $C(CH_3)_3$), 3.65-3.85 (m, 2H, $CH_2$), 5.60 (m, 1H, CHN), 6.28 (br s, 1H, NHBoc), 7.05 (dt, J=1.0 and 6.9 Hz, 1H, H indol), 7.12 (dt, J=1.3 and 7.0 Hz, 1H, H indol), 7.20-7.30 (m, 2H, H indol), 7.41 (d, J=8.0 Hz, 1H, H indol), 7.44 (d, J=2.2 Hz, 1H, H indol), 7.52-7.60 (m, 1H, H indol), 7.79 (d, J=7.9 Hz, 1H, H indol), 8.15-8.28 (m, 1H, NH), 8.30-8.40 (m, 1H, H indol), 9.05-9.1 (m, 1H, H indol), 10.20 (br s, 1H, NH) 11.22 (br s, 1H, NH). $^{13}$C NMR (75.5 MHz, DMSO-$d_6$): δ=28.2 (C ($\underline{C}H_3)_3$), 45.0 ($CH_2$), 45.9 (CHN), 77.8 ($\underline{C}(CH_3)_3$), 111.5 (CH indol), 112.2 (C indol), 112.5 (CH indol), 113.7 (C indol), 118.6 (C indol), 121.1 (CH indol), 121.2 (CH indol), 122.5 (CH indol), 122.7 (CH indol), 123.4 (CH indol), 126.2 (C indol), 136.1 (C indol), 136.2 (C indol), 138.3 (CH indol), 156.0 (C indol), 162.9 (C=O), 163.0 (C=O), 182.1 (C=O) ppm. LRMS (ESI): m/z=469 [(M+Na)$^+$], 485 [(M+K)$^+$], 915 [(2M+Na)$^+$]. HRMS (ESI) calcd for $C_{25}H_{26}N_4O_4K$ [(M+K)$^+$]: 485.1591. Found: 485.1586.

tert-Butyl(2-(2-(6-bromo-1H-indol-3-yl)-2-oxoacetamido)-2-(1H-indol-3-yl)ethyl) carbamate 3

In a dry flask under argon, the indolic primary amine (1a) (80 mg, 0.29 mmol) and triethylamine (47 mg, 0.465 mmol) were dissolved in 3 mL of dry dichloromethane and 0.1 mL of dry THF. After cooling this solution to 0° C., the acid chloride (8c) (100 mg, 0.349 mmol) was added and the mixture was stirred at 0° C. for 20 minutes. The reaction was then quenched with an aqueous saturated solution of $NaHCO_3$ and diluted with ethyl acetate. The organic layer was washed with saturated $NaHCO_3$ and water, dried over anhydrous $MgSO_4$ and concentrated. The crude material was purified by flash chromatography (EtOAc/pentane, 7/3) to afford the desired product 3 (120 mg, 0.23 mmol) as a white solid. Yield: 79%.

Mp: 145° C. IR (ATR): 3310, 2976, 1682, 1621, 1495, 1437, 1410, 1244, 1158 cm$^{-1}$. $^1$H NMR (300 MHz, DMSO-$d_6$): δ=1.36 (s, 9H, $CH_3$), 3.48-3.57 (m, 2H, $CH_2$), 5.42-5.49 (m, 1H, CH), 6.98-7.11 (m, 3H, CH and NH), 7.34-7.41 (m, 3H, CH), 7.68 (d, J=7.8 Hz, 1H, CH), 7.74 (s, 1H, CH), 8.16 (d, J=8.7 Hz, 1H, CH), 8.77-8.80 (m, 2H, CH and NH), 10.98 (br s, 1H, NH), 12.30 (br s, 1H, NH) ppm. $^{13}$C NMR (75.5 MHz, DMSO-$d_6$): δ=28.0 ($CH_3$), 43.9 ($CH_2$), 45.9 (CH), 77.7 (C), 111.4 (CH), 112.12 (C), 113.6 (C), 115.2 (CH), 115.8 (C), 118.52 (CH), 118.54 (CH), 121.1 (CH), 122.7 (CH), 122.8 (CH), 125.2 (C), 125.3 (CH), 126.1 (CH), 136.1 (C), 137.1 (C), 139.1 (CH), 155.9 (C), 162.6 (C), 182.2 (C) ppm.

tert-Butyl(2-(5-bromo-1H-indol-3-yl)-2-(2-(5-bromo-1H-indol-3-yl)-2-oxoacetamido)ethyl) carbamate 4

In a dry flask under argon, the indolic primary amine (1a) (170 mg, 0.48 mmol) and triethylamine (77 mg, 0.768 mmol) were dissolved in 5 mL of dry dichloromethane and 1 mL of dry THF. After cooling this solution to 0° C., the acid chloride (8b) (165 mg, 0.576 mmol) was added and the mixture was stirred at 0° C. for one hour. The reaction was then quenched with an aqueous saturated solution of $NaHCO_3$ and diluted with ethyl acetate. The organic layer was washed with saturated $NaHCO_3$ and water, dried over anhydrous $MgSO_4$ and concentrated. The crude material was purified by flash chromatography (EtOAc/pentane, 7/3) to afford the desired product 4 (180 mg, 0.30 mmol) as a white solid. Yield: 62%.

Mp: 207° C. IR (ATR): 3480, 3332, 3175, 1672, 1615, 1494, 1425, 1286, 1226, 1149 cm$^{-1}$. $^1$H NMR (400 MHz, DMSO-d$_6$): δ=1.34 (s, 9H, CH$_3$), 3.45-3.52 (m, 2H, CH$_2$), 5.34-5.40 (m, 1H, CH), 6.98 (t, J=5.6 Hz, 1H, NH), 7.19 (d, J=8.4 Hz, 1H, CH), 7.31 (d, J=8.8 Hz, 1H, CH), 7.38-7.42 (m, 2H, CH), 7.51 (d, J=8.4 Hz, 1H, CH), 7.84 (s, 1H, CH), 8.34 (d, J=1.6 Hz, 1H,
CH), 8.74 (s, 1H, CH), 8.92 (d, J=8.8 Hz, 1H, NH), 11.19 (br s, 1H, NH), 12.39 (br s, 1H, NH) ppm. $^{13}$C NMR (100 MHz, DMSO-d$_6$): δ=28.1 (CH$_3$), 43.8 (CH$_2$), 45.6 (CH), 77.7 (C), 111.23 (C), 111.6 (C), 113.4 (CH), 113.6 (C), 114.6 (CH), 115.2 (C), 120.9 (CH), 123.2 (CH), 123.5 (CH), 124.5 (CH), 125.9 (CH), 127.9 (C), 128.0 (C), 134.7 (C), 135.0 (C), 139.2 (CH), 155.8 (C), 162.7 (C), 182.1 (C) ppm.

Example 7

Synthesis of Compound 5

(Z)-N-Ethylidene-1-phenylinethanamine N-oxide (ba)

The synthesis of this compound was described in the literature. See: J.-N. Denis, H. Mauger, Y. Vallée *Tetrahedron Lett.* 1997, 38, 8515-8518; H. Chalaye-Mauger, J.-N. Denis, M.-T. Averbuch-Pouchot, Y. Vallée *Tetrahedron* 2000, 56, 791-804. It was prepared according to the procedure described in these references.

In a dry flask, freshly distilled acetaldehyde (1.39 g, 31.5 mmol) was dissolved in dry dichloromethane (50 mL). To this solution, N-benzylhydroxylamine (3.70 g, 30 mmol) and excess of anhydrous MgSO$_4$ (15 g) were added. The mixture was stirred for 1 hour at room temperature under argon. The solution was then filtered through a short pad of celite to remove MgSO$_4$ and concentrated under vacuum. The desired product (ba) was obtained without any further purification as a white solid. Yield: 100%.

$^1$H NMR (300 MHz, DMSO-d$_6$): δ=1.82 (d, J=5.7 Hz, 3H, CH$_3$), 4.87 (s, 2H, CH$_2$), 7.21 (q, J=5.7 Hz, 1H, CH), 7.29-7.43 (m, 5H, CH) ppm. $^{13}$C NMR (75.5 MHz, DMSO-d$_6$): δ=12.2 (CH$_3$), 67.7 (CH$_2$), 127.8 (CH), 128.2 (CH), 128.8 (CH), 133.0 (CH), 134.5 (C) ppm. LRMS (ESI): m/z=150 [(M+H)$^+$].

N-Benzyl-N-(1-(5-bromo-1H-indol-3-yl)ethyl)hydroxylamine (cb)

The synthesis of this compound was described in the literature. See: J.-N. Denis, H. Mauger, Y. Vallée *Tetrahedron Lett.* 1997, 38, 8515-8518; H. Chalaye-Mauger, J.-N. Denis, M.-T. Averbuch-Pouchot, Y. Vallée *Tetrahedron* 2000, 56, 791-804. It was prepared according to the procedure described in these references.

In a dry flask cooled at 0° C. under argon, freshly distilled acetyl chloride (2.85 mL, 40 mmol) was slowly added to dry methanol (40 mL). This solution was stirred for 10 minutes at 0° C. in order to obtain a HCl solution in methanol. In another dry flask, 5-bromoindole (ab) (3.92 g, 20 mmol) and nitrone (ba) (3.07 g, 20.6 mmol) were dissolved n dry methanol (50 mL) and this solution was slowly (over 5 minutes) added to the previous one. Temperature was maintained around 0° C. The reaction was stirred for 2 h30 at 0° C. and for 45 minutes at room temperature before quenching with a saturated aqueous solution of NaHCO$_3$. Methanol was then removed by evaporation under reduced pressure. The crude material was extracted three times with dichloromethane, washed with saturated NaHCO$_3$ and brine, dried over anhydrous MgSO$_4$ and concentrated. After purification by flash chromatography (AcOEt/pentane, 2/8 then 1/1), the desired product (cb) was obtained as a white solid. Yield: 59%.

$^1$H NMR (300 MHz, DMSO-d$_6$): δ=1.49 (d, J=6.6 Hz, 3H, CH$_3$), 3.47-3.64 (m, 2H, CH$_2$), 4.11-4.16 (m, 1H, CH), 7.15-7.33 (m, 8H, CH), 7.67 (s, 1H, OH), 7.95 (s, 1H, CH), 11.11 (br s, 1H, NH) ppm. $^{13}$C NMR (75.5 MHz, DMSO-d$_6$): δ=18.0 (CH$_3$), 59.1 (CH), 59.6 (CH$_2$), 110.8 (C), 113.2 (CH), 122.4 (CH), 123.2 (CH), 124.7 (CH), 126.2 (CH), 127.6 (CH), 128.3 (C), 128.7 (CH), 135.0 (C), 139.7 (C) ppm. LMRS (ESI): m/z=343 and 345 [(M−H)$^−$].

(Z)-N-Benzylidene-1-(5-bromo-1H-indol-3-yl)ethanamine N-oxide (eb)

The synthesis of this compound is described in the following paper: O. N. Burchak, E. Le Pihive, L. Maigre, X. Guinchard, P. Bouhours, C. Jolivalt, D. Schneider, M. Maurin, C. Giglione, T. Meinnel, J.-M. Paris, J.-N. Denis, <<Synthesis and evaluation of 1-(1H-indol-3-yl)ethanamine derivatives as new antibacterial agents>>, *Bioorg. Med. Chem.* 2011, 19, 3204-3215. It's structure was protected by the following patent: J.-N. Denis, X. Guinchard, N. Moreau, L. Neuville, Y. Vallée. Synthesis of new indole derivatives, their preparation processes, and their antibacterial uses, WO 2008110690 A2 20080918 CAN 149:356082. It was prepared according to the general procedure used for the synthesis of indolic nitrones (Y).

Compound (cb) (3.54 g, 10.27 mmol) was dissolved in warm toluene (90 mL). After complete dissolution, MnO$_2$ (4.47 g, 51.37 mmol) was added. The solution was refluxed for 10 minutes and filtered through a short pad of celite. The celite was carefully washed with ethyl acetate. Then, the clear brown solution was concentrated to afford thick brown oil. This crude material was purified by flash chromatography with silica pre-treated with 2.5% of triethylamine (neat Et$_2$O then Et$_2$O with 1% and 2% of methanol) and the desired product (eb) was obtained as a yellowish solid. Yield: 47%.

$^1$H NMR (400 MHz, DMSO-d$_6$): δ=1.80 (d, J=6.8 Hz, 3H, CH$_3$), 5.66 (q, J=6.8 Hz, 1H, CH), 7.19 (dd, J=2.0 and 8.8 Hz, 1H, CH), 7.34-7.42 (m, 4H), 7.59 (d, J=2.4 Hz, 1H, CH), 7.95 (d, J=2.0 Hz, 1H, CH), 8.15 (s, 1H, CH), 8.22 (dd, J=2.4 and 8.0 Hz, J=2.4 Hz, 2H, CH), 11.39 (br s, 1H, NH) ppm. $^{13}$C NMR (100 MHz, DMSO-d$_6$): δ=19.8 (CH$_3$), 68.1 (CH), 112.6 (C), 113.8 (C), 114.6 (CH), 115.1 (CH), 122.2 (CH), 124.3 (CH), 124.7 (CH), 127.4 (CH), 128.7 (C), 128.8 (CH), 129.2 (CH), 130.5 (CH), 131.9 (CH), 132.1 (C), 135.8 (C) ppm. LRMS (ESI): m/z=341 and 343 [(M−H)$^−$].

N-(1-(5-Bromo-1H-indol-3-yl)ethyl)hydroxylamine (fb)

The synthesis of this compound is described in the following paper: O. N. Burchak, E. Le Pihive, L. Maigre, X. Guinchard, P. Bouhours, C. Jolivalt, D. Schneider, M. Maurin, C. Giglione, T. Meinnel, J.-M. Paris, J.-N. Denis, <<Synthesis and evaluation of 1-(1H-indol-3-yl)ethanamine derivatives as new antibacterial agents>>, *Bioorg. Med. Chem.* 2011, 19, 3204-3215. It was prepared according to the general procedure used for the synthesis of indolic N-hydroxylamines (Z).

Under argon, compound (eb) (1.57 g, 4.57 mmol) was stirred for 3 hours at room temperature with hydroxylamine hydrochloride (1.59 g, 22.88 mmol) in methanol (15 mL). The solution was then concentrated, dissolved in ethyl acetate, washed with a saturated aqueous solution of NaHCO$_3$ and brine. After drying over anhydrous MgSO$_4$, the organic layer was evaporated. The residue was purified by flash chromatography (AcOEt/pentane, from 1/1 to neat EtOAc) to afford the desired product (fb) as a white solid. Yield: 70%.

IR (neat): 3405, 3120, 2805, 1455, 1435, 1375, 1330, 1245, 1225, 1085, 885, 865, 795 cm$^{-1}$. $^1$H NMR (400 MHz, DMSO-d$_6$): δ=1.38 (d, J=6.4 Hz, 3H, CH$_3$), 4.20 (q, J=6.4 Hz, 1H, CH), 5.51 (br s, 1H, OH), 7.15 (dd, J=2.0 and 8.4 Hz, 1H, CH), 7.18 (s, 1H, NH), 7.26 (s, 1H, CH), 7.30 (d, J=8.4 Hz, 1H, CH), 7.82 (d, J=2.0 Hz, 1H, CH), 11.05 (br s, 1H, NH) ppm. $^{13}$C NMR (100 MHz, DMSO-d$_6$): δ=19.2 (CH$_3$), 53.7 (CH), 110.7 (C), 113.2 (CH), 116.6 (C), 121.6 (CH), 123.1 (CH), 124.1 (CH), 128.2 (C), 134.9 (C) ppm. LRMS (ESI): m/z=253 and 255 [(M−H)$^-$].

1-(5-Bromo-1H-indol-3-yl)ethanamine (gb)

In a flask, the hydroxylamine (fb) (780 mg, 3.06 mmol) was dissolved in methanol (10 mL). A 20% wt. aqueous solution of TiCl$_3$ (4.3 mL, 6.73 mmol) was added dropwise at room temperature. When the dark TiCl$_3$ solution was added, the mixture became black but lost rapidly this dark color to become clear (due to the rapid reaction between TiCl$_3$ and the hydroxylamine). After stirring for 30 minutes, the mixture was poured in a 20% wt. aqueous solution of NaOH saturated with NaCl. The resulting solution was extracted three times with ethyl acetate. The organics were washed with water and brine, dried over anhydrous MgSO$_4$ and concentrated. The desired product (gb) was obtained without any further purification as a brown solid. Yield: 92%.

$^1$H NMR (400 MHz, DMSO-d$_6$): δ=1.38 (d, J=6.8 Hz, 3H, CH$_3$), 2.16 (br s, 2H, NH$_2$), 4.25 (q, J=6.8 Hz, 1H, CH), 7.15 (dd, J=1.6 and 8.6 Hz, 1H, CH), 7.23 (s, 1H, CH), 7.30 (d, J=8.6 Hz, 1H, CH), 7.84 (s, 1H, CH), 11.00 (br s, 1H, NH) ppm. $^{13}$C NMR (100 MHz, DMSO-d$_6$): δ=25.0 (CH$_3$), 43.4 (CH), 110.6 (C), 113.2 (CH), 119.2 (C), 121.4 (CH), 122.6 (CH), 123.1 (CH), 127.5 (C), 135.1 (C) ppm. LRMS (ESI): m/z=237 and 239 [(M−H)$^-$].

2-(5-Bromo-1H-indol-3-yl)-N-(1-(5-bromo-1H-indol-3-yl)ethyl)-2-oxoacetamide 5

In a dry flask under argon, the amine (gb) (100 mg, 0.42 mmol) and triethylamine (67 mg, 0.67 mmol) were dissolved in 3 mL of dry dichloromethane. After cooling this solution to 0° C., the acid chloride (8b) (143 mg, 0.502 mmol) was added and the mixture was stirred at 0° C. for 30 minutes. The reaction was then quenched with an aqueous saturated solution of NaHCO$_3$ and diluted with ethyl acetate. The organic layer was washed with saturated NaHCO$_3$ and water, dried over anhydrous MgSO$_4$ and concentrated. The crude material was purified by flash chromatography (EtOAc/pentane, 1/1) to afford the desired product 5 (130 mg, 0.266 mmol) as a white solid. Yield: 63%.

Mp: 141° C. IR (ATR): 3270, 2975, 1665, 1614, 1494, 1418, 1229, 1124 cm$^{-1}$. $^1$H NMR (300 MHz, DMSO-d$_6$): δ=1.62 (d, J=6.9 Hz, 3H, CH$_3$), 5.34-5.44 (m, 1H, CH), 7.17 (d, J=8.4 Hz, 1H, CH), 7.32-7.41 (m, 3H, CH), 7.52 (d, J=8.4 Hz, 1H, CH), 7.86 (s, 1H, CH), 8.34 (d, J=2.1 Hz, 1H, CH), 8.74 (s, 1H, CH), 8.94 (d, J=8.8 Hz, 1H, NH), 11.15 (br s, 1H, NH), 12.41 (br s, 1H, NH) ppm. $^{13}$C NMR (75.5 MHz, DMSO-d$_6$): δ=20.3 (CH$_3$), 40.6 (CH), 111.18 (C), 111.7 (C), 113.4 (CH), 114.6 (CH), 115.2 (C), 116.9 (CH), 121.1 (CH), 123.2 (CH), 123.5 (CH), 124.1 (CH), 126.0 (CH), 127.5 (C), 127.8 (C), 134.97 (C), 135.03 (C), 139.1 (CH), 162.5 (C), 182.6 (C) ppm.

Example 8

Alternative synthesis of indolic amine (gb)

1-(5-Bromo-1H-indol-3-yl)ethanone (jb)

A 1.0 M solution of SnCl$_4$ (10 mL, 10.0 mmol) was added to a stirred solution of 5-bromoindole (ab) (980 mg, 5.0 mmol) and acetyl chloride (0.714 mL, 785 mg, 10.0 mmol) in 20 mL of dry toluene at 0° C. The resulting mixture was stirred at room temperature during 4 hours, and then 50 ml, of water was added. The mixture was extracted with EtOAc (3×20 mL) and the collected organic layers were washed with water, brine, dried over anhydrous MgSO$_4$, filtered and concentrated under vacuum. Column chromatography using EtOAc-pentane (from 5/95 to 80/20) yielded pure acetylindole (jb) (1.0 g, 4.2 mmol) as a white solid. Yield: 84%.

$^1$H NMR (300 MHz, DMSO-d$_6$): δ=2.44 (s, 3H), 7.33 (dd, J=2.0 and 8.6 Hz, 1H), 7.45 (dd, J=0.4 and 8.6 Hz, 1H), 8.31 (dd, J=0.4 and 2.0 Hz, 1H), 8.34 (s, 1H) ppm. $^{13}$C NMR (75.5 MHz, DMSO-d$_6$): δ=27.1, 114.2, 114.5, 116.2, 123.4, 125.3, 127.0, 135.4, 135.5, 192.8 ppm.

1-(5-Bromo-1H-indol-3-yl)ethanone oxime (kb)

NH$_2$OH.HCl (834 mg, 12.0 mmol) was added to a stirred solution of 3-acetyl-5-bromoindole (jb) (952 mg, 4.0 mmol) and pyridine (0.967 mL, 948 mg, 12.0 mmol) in 20 mL of ethanol. The resulting mixture was stirred at reflux for 2 hours and then ethanol was evaporated. Water (50 mL) was added and then the mixture was extracted with EtOAc (3×30 mL). The collected organic layers were washed with water, brine, dried over anhydrous MgSO$_4$, filtered and concentrated under vacuum. Pure oxime (kb) (1.0 g, 3.95 mmol) was obtained as a colorless oil. Yield: 99%.

$^1$H NMR (300 MHz, CD$_3$OD): δ=2.22 (s, 3H), 7.18-7.28 (m, 2H), 7.45 (s, 1H), 8.37 (s, 1H) ppm.

1-(5-Bromo-1H-indol-3-yl)ethanamine (gb)

To a stirred and carefully deoxygenated solution of indolic oxime (kb) (633 mg, 2.5 mmol) and H$_2$O (720 mg, 40.0 mmol, 16 equiv.) in 10 mL of THF, a 0.1 M solution of SmI$_2$ (110 mL, 11.0 mmol, 4.4 equiv.) in THF was added at room temperature under argon. After 10 minutes, a saturated solution of Na$_2$S$_2$O$_3$ (20 mL) and NaHCO$_3$ (20 mL) then EtOAc (50 mL) were added. After extraction, the organic phase was washed with brine, dried over anhydrous Na$_2$SO$_4$, filtered, and concentrated. Pure amine (gb) (560 mg, 2.34 mmol) was obtained as a white solid. Yield: 94%.

$^1$H NMR (300 MHz, CDCl$_3$): δ=1.38 (d, J=6.6 Hz, 3H), 2.50 (br s, 2H), 4.26 (q, J=6.6 Hz, 1H), 6.88 (s, 1H), 6.9-7.02 (m, 1H), 7.09-7.12 (m, 1H), 7.66 (s, 1H), 9.00 (br s, 1H) ppm. $^{13}$C NMR (75.5 MHz, CDCl$_3$): δ=24.3, 43.6, 112.3, 112.8, 121.2, 121.4, 121.5, 124.6, 127.5, 135.1 ppm.

Example 9

Comparative Examples t-Butyl(2-benzamido-2-(5-bromo-1H-indol-3-yl)ethyl) carbamate 12

In a dry flask under argon, the [2-amino-2-(5-bromo-1H-indol-3-yl)ethyl]carbamic acid tert-butyl ester (1b) (60 mg, 0.17 mmol) and triethylamine (0.028 mL, 0.20 mmol) were dissolved in 2 mL of dry dichloromethane. After cooling this solution to 0° C., benzoyl chloride (0.020 mL, 0.17 mmol) was added dropwise and the mixture was stirred at 0° C. for 15 minutes. The reaction was then quenched with water and diluted with ethyl acetate. The organic layer was washed with a 1M aqueous solution of HCl and water, dried over anhydrous $MgSO_4$ and concentrated. The crude material was purified by flash chromatography (EtOAc/pentane, 1/1 then 7/3). After recrystallization in a mixture of ethyl acetate and pentane, the desired product 12 (45 mg, 0.098 mmol) was obtained as a white solid. Yield: 58%.

Mp: 187° C. IR (ATR): 3375, 3310, 1661, 1629, 1519, 1276, 1163 cm$^{-1}$. $^1$H NMR (400 MHz, DMSO-d$_6$): δ=1.33 (s, 9H, CH$_3$), 3.44-3.52 (m, 2H, CH$_2$), 5.42-5.49 (m, 1H, CH), 7.00 (t, J=5.8 Hz, 1H, NH), 7.17 (d, J=6.4 Hz, 1H, CH), 7.32 (d, J=8.8 Hz, 1H, CH), 7.38 (s, 1H, CH), 7.44 (t, J=7.2 Hz, 2H, CH), 7.51 (t, J=7.2 Hz, 1H, CH), 7.82-7.88 (m, 3H, CH and NH), 8.55 (d, J=8.8 Hz, 1H, CH), 11.14 (br s, 1H, NH) ppm. $^{13}$C NMR (100 MHz, DMSO-d$_6$): δ=28.1 (CH$_3$), 44.1 (CH$_2$), 46.2 (CH), 77.6 (C), 111.1 (C), 113.3 (CH), 114.5 (C), 121.0 (CH), 123.4 (CH), 124.2 (CH), 127.3 (CH), 128.0 (CH), 130.9 (CH), 134.61 (C), 134.65 (C), 134.71 (C), 155.8 (C), 165.8 (C) ppm. LRMS (ESI): m/z=480 and 482 [(M+Na)$^+$].

tert-Butyl(2-(4-bromo)benzamido-2-(5-bromo-1H-indol-3-yl)ethyl)carbamate 12a

In a dry flask under argon, 4-bromophenylacetic acid (860 mg, 4 mmol) was dissolved in dry dichloromethane (30 mL) and few drops of dry DMF. The sluggish solution was cooled to 0° C. and freshly distilled oxalyl chloride (0.412 mL, 4.8 mmol) was added dropwise. The mixture was then stirred for 2 hours at room temperature and directly evaporated under reduced pressure. The desired acid chloride was obtained and dissolved in 4 mL of dichloromethane to make a 1M solution.

In a dry flask under argon, the [2-amino-2-(5-bromo-1H-indol-3-yl)ethyl]carbamic acid tert-butyl ester (1b) (60 mg, 0.17 mmol) and triethylamine (0.033 mL, 0.24 mmol) were dissolved in 1 mL of dry dichloromethane. After cooling this solution to 0° C., the 1M solution of 2-(4-bromophenyl)acetyl chloride previously obtained (0.204 mL, 0.204 mmol) was added dropwise and the mixture was stirred at 0° C. for one hour. The reaction was then quenched with water and diluted with ethyl acetate. The organic layer was washed with a 1M aqueous solution of HCl and water, dried over anhydrous $MgSO_4$ and concentrated. The crude material was purified by flash chromatography (EtOAc/pentane, 1/1 then 8/2). After recrystallization in a mixture of ethyl acetate and pentane, the desired product 12a (50 mg, 0.09 mmol) was obtained as a white solid. Yield: 54%.

Mp: 131° C. IR (ATR): 3425, 3338, 1678, 1634, 1533, 1488, 1458, 1276, 1169 cm$^{-1}$. $^1$H NMR (400 MHz, DMSO-d$_6$): δ=1.34 (s, 9H, CH$_3$), 3.29-3.43 (m, 2H, CH$_2$), 3.41 (s, 2H, CH$_2$), 5.17-5.23 (m, 1H, CH), 6.82 (t, J=6.0 Hz, 1H, NH), 7.17 (dd, J=1.6 and 8.4 Hz, 1H, CH), 7.21 (d, J=8.4 Hz, 2H, CH), 7.29-7.31 (m, 2H, CH), 7.45 (d, J=8.4 Hz, 2H, CH), 7.66 (s, 1H, CH), 8.30 (d, J=8.8 Hz, 1H, NH), 11.13 (br s, 1H, NH) ppm. $^{13}$C NMR (100 MHz, DMSO-d$_6$): δ=29.1 (CH$_3$), 42.6 (CH$_2$), 45.1 (CH$_2$), 46.3 (CH), 78.6 (C), 112.1 (C), 114.3 (CH), 115.2 (C), 120.4 (C), 122.0 (CH), 124.5 (CH), 124.8 (CH), 128.9 (C), 131.9 (CH), 132.1 (CH), 135.8 (C), 136.8 (C), 156.6 (C), 170.0 (C) ppm. LRMS (ESI): m/z=572, 574 and 576 and [(M+Na)$^+$].

tert-Butyl(2-(5-bromo-1H-indol-3-yl)-2-(2,2,2-trifluoroacetamido)ethyl)carbamate 13

In a dry flask under argon, the [2-amino-2-(5-bromo-1H-indol-3-yl)ethyl]carbamic acid tert-butyl ester (1b) (80 mg, 0.226 mmol) and triethylamine (0.063 mL, 0.452 mmol) were dissolved in 2 mL of dry dichloromethane. After cooling this solution to 0° C., trifluoroacetic anhydride (0.035 mL, 0.248 mmol) was added and the mixture was stirred at 0° C. for 15 minutes. The reaction was then quenched with an aqueous saturated solution of NaHCO$_3$ and diluted with dichloromethane. The organic layer was washed with saturated NaHCO$_3$, 1M aqueous HCl and water, dried over anhydrous $MgSO_4$ and concentrated. The crude material was purified by flash chromatography (EtOAc/pentane, 3/7) to afford the desired product 13 (70 mg, 0.156 mmol) as a white solid. Yield: 69%.

IR (ATR): 3441, 3323, 1676, 1533, 1457, 1275, 1162 cm$^{-1}$. $^1$H NMR (300 MHz, DMSO-d$_6$): δ=1.36 (s, 9H, CH$_3$), 3.43-3.48 (m, 2H, CH$_2$), 5.25-5.32 (m, 1H, CH), 7.03 (t, J=5.7 Hz, 1H, NH), 7.20 (dd, J=2.0 and 8.7 Hz, 1H, CH), 7.34 (d, J=8.7 Hz, 1H, CH), 7.38 (d, J=2.0 Hz, 1H, CH), 7.72 (s, 1H, CH), 9.63 (d, J=8.7 Hz, 1H, NH), 11.24 (br s, 1H, NH) ppm. $^{13}$C NMR (75.5 MHz, DMSO-d$_6$): δ=28.0 (CH$_3$), 43.4 (CH$_2$), 46.6 (CH), 77.8 (C), 111.4 (C), 112.3 (C), 133.5 (CH), 120.6 (CH), 123.7 (CH), 127.7 (CH), 155.9 (CF$_3$, J$_{C-F}$=288.8 Hz), 127.7 (C), 134.7 (C), 155.6 (C, J$_{C-F}$=15.8 Hz), 156.0 (C) ppm. LRMS (ESI): m/z=472 and 474 [(M+Na)$^+$].

tert-Butyl(2-(5-bromo-1H-indol-3-yl)-2-(nicotinamido)ethyl) carbamate 14

In a dry flask under argon, nicotinic acid (492 mg, 4 mmol) was dissolved in dry dichloromethane (30 mL) and few drops of dry DMF. The sluggish solution was cooled to 0° C. and freshly distilled oxalyl chloride (0.412 mL, 4.8 mmol) was added dropwise. The mixture was then stirred for 2 hours at room temperature and directly evaporated under reduced pressure. The solid was washed with pentane and dried under vacuum. The desired nicotinoyl chloride hydrochloride was obtained as a white solid and used straightaway.

In a dry flask under argon, the [2-amino-2-(5-bromo-1H-indol-3-yl)ethyl]carbamic acid tert-butyl ester (1b) (80 mg, 0.226 mmol) and triethylamine (0.094 mL, 0.68 mmol) were dissolved in 2 mL of dry dichloromethane. After cooling this solution to 0° C., the nicotinoyl chloride hydrochloride previously obtained (48 mg, 0.271 mmol) was added and the mixture was stirred at 0° C. for 30 minutes. The reaction was then quenched with water and diluted with ethyl acetate. The organic layer was washed with a 1M aqueous solution of HCl and water, dried over anhydrous $MgSO_4$ and concentrated. The crude material was purified by flash chromatography (EtOAc/pentane, from 1/1 to EtOAc). After recrystallization in a mixture of ethyl acetate and pentane, the desired product 14 (60 mg, 0.131 mmol) was obtained as a white solid. Yield: 58%.

Mp: 195° C. IR (ATR): 3325, 3209, 2972, 1682, 1634, 1544, 1272, 1167 cm$^{-1}$. $^1$H NMR (400 MHz, DMSO-d$_6$): δ=1.32 (s, 9H, CH$_3$), 3.46-3.50 (m, 2H, CH$_2$), 5.43-5.49 (m, 1H, CH), 7.03 (t, J=6.0 Hz, 1H, NH), 7.18 (d, J=8.4 Hz, 1H, CH), 7.32 (d, J=8.4 Hz, 1H, CH), 7.40 (s, 1H, CH), 7.49 (dd, J=4.8 and 8.0 Hz, 1H, CH), 7.83 (s, 1H, CH), 8.19 (d, J=8.0 Hz, 1H, CH), 8.68 (d, J=3.6 Hz, 1H, CH), 8.77 (d, J=8.8 Hz, 1H, NH), 9.02 (s, 1H, CH), 11.16 (s, 1H, NH) ppm. $^{13}$C NMR (100 MHz, DMSO-d$_6$): δ=29.1 (CH$_3$), 45.1 (CH$_2$), 47.3 (CH$_3$), 78.6 (C), 112.2 (C), 114.4 (CH), 115.1 (C), 121.9 (CH), 124.2 (CH), 124.4 (CH), 125.3 (CH), 129.0 (C), 131.1 (C), 135.7 (C), 136.0 (CH), 149.5 (CH), 152.6 (CH), 156.8 (C), 165.4 (C) ppm. LRMS (ESI): m/z=459 and 461 [(M+H)$^+$].

Example 10

Synthesis of cyclic keto-amides 6a-f

10.1. Synthesis of N-hydroxylamines 10a-c

General Procedure

To a stirred suspension of methyltrioxorhenium (MTO) (6 mg, 0.025 mmol) and urea hydrogen peroxide (UHP) (4.7 g, 50.0 mmol) in dichloromethane (100 mL), 1 mL of MeOH was added at room temperature. Within 15 min the yellow colour appeared, the reaction mixture was cooled in an ice bath and cyclic amine (piperidine, morpholine or (N-Boc) pyperazine) (5.0 mmol) was added in one portion, the yellow color disappeared. The ice bath was removed and another portion of MTO (6 mg, 0.025 mmol) was added at room temperature. The color of reaction mixture turned pale yellow. After 5 minutes of stirring, the excess of UHP was filtered off Dichloromethane and MeOH were evaporated under reduced pressure. The residue was diluted with dichloromethane (100 mL), a solid substance was filtered off and the filtrate was washed with brine, dried over anhydrous $MgSO_4$ and concentrated under reduced pressure till 50 ml. The nitrone solution 9a-c was used for the next step without any purification.

A cold solution of hydrochloric acid was prepared by reaction of freshly distilled acetyl chloride (0.714 ml, 785 mg, 10.0 mmol) with 5 mL of dry methanol. This solution was stirred at 0° C. during 15 min and was added to a solution of both nitrone 9a-c (5.0 mmol) and indole (aa or ab) (5.0 mmol) in 15 mL of dry methanol and 50 ml of dry dichloromethane. The reaction mixture was stirred at 0° C. during 2 hours to completion. A saturated aqueous solution of $NaHCO_3$ was then added. The mixture was extracted with dichloromethane (3×20 mL) and the collected organic layers were washed with brine, dried over anhydrous $Na_2SO_4$, filtered and concentrated under vacuum.

Column chromatography using EtOAc-pentane (10/90-80/20) yielded pure N-hydroxylamines 10a-f as white solids.

2-(1H-Indol-3-yl)piperidin-1-ol 10a

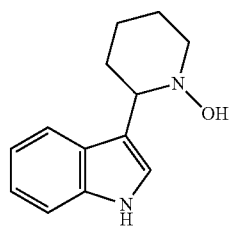 [SMILES: ON1CCCCC1c1c[nH]c2ccccc12]

The compound 10a (840 mg, 3.89 mmol) was obtained from piperidine (425 mg, 5.0 mmol) and indole (aa) (585 mg, 5.0 mmol). Yield: 78%.

IR (neat): 3300, 2925, 2855, 2830, 1445, 1335, 1315, 1225, 1095, 1065, 1035, 1010, 870, 775, 730 $cm^{-1}$. $^1H$ NMR (300 MHz, $CDCl_3$): δ=1.31-1.68 (m, 1H), 1.72-1.81 (m, 3H), 1.86-1.92 (m, 2H), 2.61 (dt, J=3.8 and 10.9 Hz, 1H), 3.34 (d, J=11.4 Hz, 1H), 3.69 (dd, J=6.5 and 8.2 Hz, 1H), 5.59 (br s, 1H), 6.98 (d, J=2.4 Hz, 1H), 7.09 (ddd, J=1.2, 7.1 and 7.8 Hz, 1H), 7.17 (ddd, J=1.2, 7.1 and 8.1 Hz, 1H), 7.30 (dt, J=1.2 and 8.1 Hz, 1H), 7.83 (d, J=7.8 Hz, 1H), 8.10 (br s, 1H) ppm. $^{13}C$ NMR (75.5 MHz, $CDCl_3$): δ=24.3, 25.9, 33.9, 59.1, 65.9, 111.1, 117.9, 119.3, 120.0, 121.9, 122.1, 126.8, 136.2 ppm. LRMS (ESI): m/z (%)=217 (100) [(M+H)$^+$].

3-(1H-Indol-3-yl)morpholin-4-ol 10b

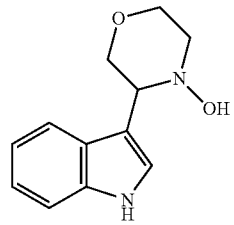 [SMILES: ON1CCOCC1c1c[nH]c2ccccc12]

The compound 10b (890 mg, 4.08 mmol) was obtained from morpholine (435 mg, 5.0 mmol) and indole (aa) (585 mg, 5.0 mmol). Yield: 82%.

IR (neat): 3340, 2920, 2855, 1455, 1435, 1340, 1435, 1340, 1300, 1220, 1100, 1085, 965, 875, 745 $cm^{-1}$. $^1H$ NMR (300 MHz, $CDCl_3$-$CD_3OD$): δ=2.88 (td, J=3.6 and 11.5 Hz, 1H), 3.21 (d, J=10.9 Hz, 1H), 3.65-3.96 (m, 5H), 7.02-7.15 (m, 2H), 7.16 (s, 1H), 7.33 (d, J=7.9 Hz, 1H), 7.76 (d, J=7.9 Hz, 1H) ppm. $^{13}C$ NMR (75.5 MHz, $CDCl_3$-$CD_3OD$): δ=57.7, 64.8, 66.3, 71.1, 111.0, 111.3, 118.7, 118.8, 121.2, 122.8, 126.4, 136.1 ppm. LRMS (ESI): m/z (%)=219 (100) [(M+H)$^+$], 201 (18) [(M–$H_2O$+H)$^+$].

tert-Butyl 4-hydroxy-3-(1H-indol-3-yl)piperazin-1-carboxylate 10c

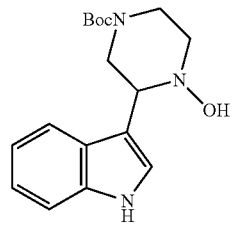 [SMILES: CC(C)(C)OC(=O)N1CCN(O)C(c2c[nH]c3ccccc23)C1]

The compound 10c (1.208 g, 3.81 mmol) was obtained from N-Boc-piperazine (930 mg, 5.0 mmol) and indole (aa) (585 mg, 5.0 mmol). Yield: 76%.

IR (neat): 3305, 2915, 2885, 1740, 1660, 1615, 1455, 1430, 1365, 1280, 1250, 1165, 1135, 1015, 745 $cm^{-1}$. $^1H$ NMR (300 MHz, $CD_3OD$): δ=1.47 (s, 9H), 2.61-2.74 (m, 1H), 3.08-3.20 (m, 2H), 3.23-3.30 (m, 1H), 3.71-3.79 (m, 1H), 4.06-4.13 (m, 2H), 7.01 (ddd, J=1.2, 7.8 and 9.0 Hz, 1H), 7.10 (ddd, J=1.2, 7.0 and 9.3 Hz, 1H), 7.25 (s, 1H), 7.35 (d, J=8.1 Hz, 1H), 7.74 (d, J=7.7 Hz, 1H) ppm. $^{13}C$ NMR (75.5 MHz, $CD_3OD$): δ=28.7 (3C), 58.5, 58.8, 61.6, 65.7, 81.5 (C), 112.3, 114.3, 119.9, 120.2, 122.5, 124.1, 128.1, 138.1, 156.2 ppm. LRMS (ESI): m/z (%)=340 (22) [(M+Na)$^+$], 318 (42) [(M+H)$^+$], 262 (100) [(M t-Bu+H)$^+$].

2-(5-Bromo-1H-indol-3-yl)piperidin-1-ol 10d

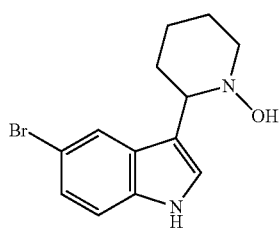 [SMILES: ON1CCCCC1c1c[nH]c2ccc(Br)cc12]

The compound 10d (915 mg, 3.10 mmol) was obtained from piperidine (425 mg, 5.0 mmol) and 5-bromoindole (ab) (980 mg, 5.0 mmol). Yield: 62%.

IR (neat): 3280, 2940, 2920, 2855, 2825, 1465, 1445, 1315, 1250, 1225, 1120, 1095, 1060, 1035, 880, 790, 775, 760 cm$^{-1}$. $^1$H NMR (300 MHz, CD$_3$OD): δ=1.33-1.52 (m, 1H), 1.68-1.98 (m, 5H), 2.65 (td, J=4.1 and 10.8 Hz, 1H), 3.38 (d, J=10.4 Hz, 1H), 3.63 (dd, J=6.5 and 8.2 Hz, 1H), 7.15 (dd, J=1.9 and 8.6 Hz, 1H), 7.22 (s, 1H), 7.25 (dd, J=0.5 and 8.6 Hz, 1H), 7.89 (d, J=1.9 Hz, 1H) ppm. $^{13}$C NMR (75.5 MHz, CD$_3$OD): δ=25.5, 27.0, 35.0, 60.9, 67.0, 112.8, 113.8, 118.1, 123.2, 124.9, 125.1, 130.3, 136.7 ppm. LRMS (ESI): m/z (%)=295 (100) and 297 (95) [(M+H)$^+$].

3-(5-Bromo-1H-indol-3-yl)morpholin-4-ol 10e

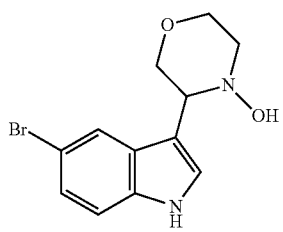

The compound 10e (1.13 g, 3.79 mmol) was obtained from morpholine (435 mg, 5.0 mmol) and 5-bromoindole (ab) (980 mg, 5.0 mmol). Yield: 76%.

IR (neat): 3310, 2885, 2860, 1465, 1330, 1295, 1100, 1055, 1045, 965, 875, 780, 745 cm$^{-1}$. $^1$H NMR (300 MHz, CDCl$_3$-CD$_3$OD): δ=2.86 (td, J=3.6 and 11.5 Hz, 1H), 3.23 (d, J=10.9 Hz, 1H), 3.62-3.97 (m, 5H), 7.16-7.24 (m, 3H), 7.92 (d, J=1.3 Hz, 1H) ppm. $^{13}$C NMR (75.5 MHz, CDCl$_3$-CD$_3$OD): δ=57.8, 64.6, 66.3, 70.9, 111.1, 111.8, 112.4, 121.4, 123.9, 124.1, 128.1, 134.7 ppm. LRMS (ESI): m/z (%)=297 (100) and 299 (95) [(M+H)$^+$].

tert-Butyl 3-(5-bromo-1H-indol-3-yl)-4-hydroxypiperazine-1-carboxylate 10f

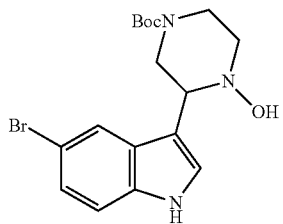

The compound 10f (1.03 g, 2.61 mmol) was obtained from (N-Boc)piperazine (930 mg, 5.0 mmol) and 5-bromoindole (ab) (980 mg, 5.0 mmol). Yield: 52%.

IR (neat): 3290, 2970, 2920, 2855, 1655, 1430, 1365, 1270, 1250, 1165, 1135, 1110, 880, 865, 785 cm$^{-1}$. $^1$H NMR (300 MHz, CD$_3$OD): δ=1.48 (s, 9H), 2.65-2.72 (m, 1H), 3.08-3.18 (m, 2H), 3.30-3.34 (m, 1H), 3.67-3.71 (m, 1H), 4.05-4.14 (m, 2H), 7.18 (dd, J=1.9 and 8.7 Hz, 1H), 7.27 (dd, J=0.6 and 8.7 Hz, 1H), 7.28 (s, 1H), 7.90 (s, 1H) ppm. $^{13}$C NMR (75.5 MHz, CD$_3$OD): δ=28.7 (3C), 49.3, 49.5, 58.9, 65.5, 81.6 (C), 113.1, 114.0, 114.3, 123.0, 125.2, 125.7, 129.8, 136.8, 156.2 ppm. LRMS (ESI): m/z=418 and 420 [(M+Na)$^+$], 396 and 398 [(M+H)$^+$].

10.2 Synthesis of amines 11a-f

General Procedure

To a stirred solution of each indolic N-hydroxylamine 10a-f (1.0 mmol) in 5 mL of methanol was added 1.7 g of a 20% aqueous solution of titanium trichloride (339 mg, 2.2 mmol). The resulting mixture was stirred at room temperature during 30 min. A large excess of an aqueous 20% NaOH solution saturated with NaCl was added. Methanol was then removed under vacuum and the crude mixture was extracted with ethyl acetate (3×20 mL). Combined organic layers were washed with H$_2$O, brine, dried over anhydrous Na$_2$SO$_4$, filtered and concentrated under vacuum.

Pure amines 11a-f were obtained as white solids and were used without purification.

3-(Piperidin-2-yl)-1H-indole 11a

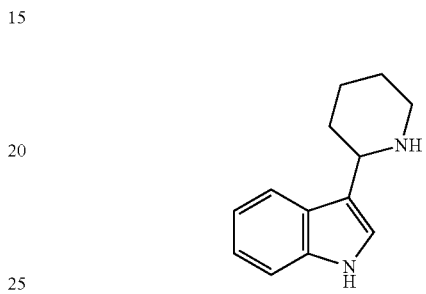

The compound 11a (200 mg, 1 mmol) was obtained from N-hydroxylamine 10a (216 mg, 1.0 mmol). Yield: 100%.

IR (neat): 3160, 2940, 2925, 1590, 1450, 1440, 1430, 1340, 1230, 1105, 1000, 745 cm$^{-1}$. $^1$H NMR (300 MHz, CD$_3$OD): δ=1.73-2.06 (m, 4H), 2.12-2.20 (m, 2H), 3.20 (td, J=3.6 and 12.5 Hz, 1H), 3.35-3.42 (m, 1H), 4.50-4.55 (m, 1H), 7.11 (td, J=1.3 and 7.9 Hz, 1H), 7.17 (td, J=1.3 and 7.1 Hz, 1H), 7.42 (dt, J=0.8 and 7.9 Hz, 1H), 7.47 (s, 1H), 7.73 (dt, J=0.8 and 7.7 Hz, 1H) ppm. $^{13}$C NMR (75.5 MHz, CD$_3$OD): δ=23.6, 24.4, 31.5, 46.7, 54.8, 112.8, 113.1, 119.2, 120.7, 123.3, 124.7, 126.8, 137.9 ppm. LRMS (ESI): m/z (%)=201 (100) [(M+H)$^+$].

3-(1H-Indol-3-yl)morpholine 11b

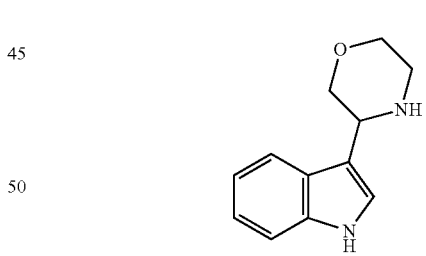

The compound 11b (200 mg, 0.99 mmol) was obtained from N-hydroxylamine 10b (218 mg, 1.0 mmol). Yield: 99%.

IR (neat): 3405, 3280, 2970, 2855, 1550, 1450, 1440, 1340, 1225, 1100, 930, 865, 840, 740 cm$^{-1}$. $^1$H NMR (300 MHz, CDCl$_3$): δ=1.99-2.16 (br s, 1H), 3.00 (dt, J=2.2 and 11.9 Hz, 1H), 3.15 (td, J=3.3 and 11.1 Hz, 1H), 3.55 (dd, J=9.9 and 11.1 Hz, 1H), 3.68 (td, J=2.7 and 11.1 Hz, 1H), 3.86-3.95 (m, 1H), 4.02 (dd, J=3.1 and 11.1 Hz, 1H), 4.30 (dd, J=3.1 and 9.9 Hz, 1H), 7.08-7.21 (m, 3H), 7.28-7.31 (m, 1H), 7.69-7.73 (m, 1H), 8.53 (br s, 1H) ppm. $^{13}$C NMR (75.5 MHz, CDCl$_3$): δ=46.7, 53.1, 67.3, 73.1, 111.2, 115.5, 118.9, 119.5, 121.5, 122.1, 126.1, 136.1 ppm. LRMS (ESI): m/z (%)=203 (100) [(M+H)$^+$].

tert-Butyl 3-(1H-indol-3-yl)piperazine-1-carboxylate 11c

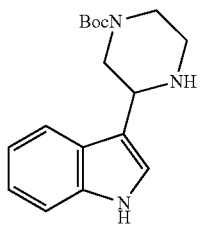 [SMILES: CC(C)(C)OC(=O)N1CCNC(c2c[nH]c3ccccc23)C1]

The compound 11c (283 mg, 0.94 mmol) was obtained from N-hydroxylamine 10c (317 mg, 1.0 mmol). Yield: 94%.

IR (neat): 3325, 2905, 2855, 2800, 1670, 1455, 1440, 1400, 1365, 1270, 1245, 1165, 1020, 740 cm$^{-1}$. $^1$H NMR (300 MHz, CD$_3$OD): δ=1.48 (s, 9H), 2.81-3.05 (m, 4H), 4.00-4.05 (m, 2H), 4.24 (d, J=12.7 Hz, 1H), 7.03 (t, J=7.2 Hz, 1H), 7.12 (t, J=7.2 Hz, 1H), 7.23 (s, 1H), 7.36 (d, J=8.1 Hz, 1H), 7.63 (d, J=7.8 Hz, 1H) ppm. $^{13}$C NMR (75 MHz, CD$_3$OD): δ=28.8 (3C), 46.7, 48.8, 49.3, 53.9, 81.4 (C), 112.5, 115.7, 119.3, 120.1, 122.8 (2C), 127.3, 138.0, 156.4 ppm. LRMS (ESI): m/z (%)=302 (57) [(M+H)$^+$], 246 (100) [(M t-Bu+H)$^+$].

5-Bromo-3-(piperidin-2-yl)-1H-indole 11d

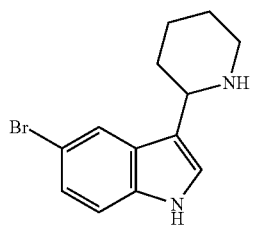 [SMILES: Brc1ccc2[nH]cc(C3CCCCN3)c2c1]

The compound 11d (279 mg, 1 mmol) was obtained from N-hydroxylamine 10d (295 mg, 1.0 mmol). Yield: 100%.

IR (neat): 3195, 2925, 2805, 1455, 1435, 1320, 1300, 1225, 1115, 1100, 885, 865, 785 cm$^{-1}$. $^1$H NMR (300 MHz, CDCl$_3$-CD$_3$OD): δ=1.55-1.81 (m, 4H), 1.90-2.08 (m, 2H), 2.88 (td, J=3.1 and 11.8 Hz, 1H), 3.22 (d, J=11.8 Hz, 1H), 3.96-4.00 (m, 1H), 4.00 (br s, 1H), 7.20-7.38 (m, 3H), 7.73-7.74 (m, 1H) ppm. $^{13}$C NMR (75.5 MHz, CDCl$_3$-CD$_3$OD): δ=24.5, 24.6, 32.5, 46.8, 53.5, 112.1, 112.8, 116.6, 120.5, 122.8, 124.3, 127.3, 134.7 ppm. LRMS (ESI): m/z (%)=279 (100) and 281 (100) [(M+H)$^+$].

3-(5-Bromo-1H-indol-3-yl)morpholine 11e

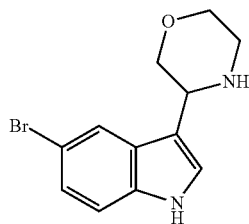 [SMILES: Brc1ccc2[nH]cc(C3COCCN3)c2c1]

The compound 11e (280 mg, 1 mmol) was obtained from N-hydroxylamine 10e (297 mg, 1.0 mmol). Yield: 100%.

IR (neat): 3295, 2960, 2915, 2855, 1455, 1435, 1285, 1205, 1100, 1065, 1020, 875, 805, 775 cm$^{-1}$. $^1$H NMR (300 MHz, CDCl$_3$-CD$_3$OD): δ=2.99 (dt, J=2.2 and 11.8 Hz, 1H), 3.08 (br s, 1H), 3.13 (ddd, J=3.2, 11.1 and 12.1 Hz, 1H), 3.53 (dd, J=10.0 and 11.2 Hz, 1H), 3.68 (td, J=2.8 and 11.1 Hz, 1H), 3.87-3.94 (m, 1H), 3.96 (dd, J=3.2 and 11.2 Hz, 1H), 4.21 (dd, J=2.8 and 10.0 Hz, 1H), 7.18-7.26 (m, 3H), 7.79-7.80 (m, 1H) ppm. $^{13}$C NMR (75.5 MHz, CDCl$_3$-CD$_3$OD): δ=46.2, 52.5, 66.9, 72.5, 112.4, 112.8, 113.8, 121.1, 123.0, 124.7, 127.6, 134.7 ppm. LRMS (ESI): m/z (%)=281 (100) and 283 (95) [(M+H)$^+$].

tert-Butyl 3-(5-bromo-1H-indol-3-yl)piperazine-1-carboxylate 11f

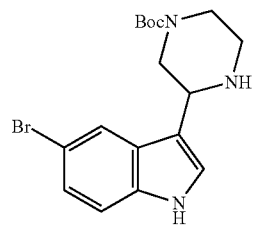 [SMILES: CC(C)(C)OC(=O)N1CCNC(c2c[nH]c3ccc(Br)cc23)C1]

The compound 11f (375 mg, 0.99 mmol) was obtained from N-hydroxylamine 10f (396 mg, 1.0 mmol). Yield: 99%.

IR (neat): 3280, 2970, 2905, 2865, 1665, 1455, 1425, 1365, 1245, 1165, 1125, 880, 860 795 cm$^{-1}$. $^1$H NMR (300 MHz, CDCl$_3$): δ=1.50 (s, 9H), 2.08-2.16 (br s, 1H), 2.87-3.08 (m, 4H), 3.96-4.19 (m, 3H), 7.10 (br s, 1H), 7.16-7.26 (m, 2H), 7.87 (s, 1H), 8.85 (br s, 1H) ppm. $^{13}$C NMR (75.5 MHz, CDCl$_3$): δ=28.5 (3C), 46.0, 48.5, 48.8, 52.8, 79.9 (C), 112.7, 112.8, 116.0, 121.8, 122.6, 124.9, 127.7, 134.9, 154.9 ppm. LRMS (ESI): m/z (%)=380 (25) and 382 (25) [(M+H)$^+$], 324 (100) and 326 (95) [M t-Bu+H)$^+$].

10.3 Synthesis of bis-indoles 6a-f

General Procedure

To a stirred solution of indolic amine 11a-f (1.0 mmol) in 5 mL of dry dichloromethane, indolic oxoacetyl chloride (8a) or (8b) (1.2 mmol) was added at 0° C. The resulting mixture was stirred at room temperature during 1 hour. A saturated aqueous solution of NaHCO$_3$ was then added. The mixture was extracted with EtOAc (3×20 mL) and the collected organic layers were washed with brine, dried over anhydrous MgSO$_4$, filtered and concentrated under vacuum.

Column chromatography using EtOAc-pentane (from 10/90 to 80/20) yielded pure bis-indole 6a-f as a beige foam.

1-(2-(1H-Indol-3-yl)piperidin-1-yl)-2-(1H-indol-3-yl)ethane-1,2-dione 6a

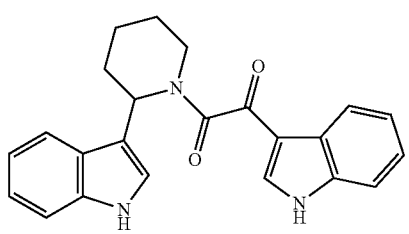 [SMILES: O=C(C(=O)N1CCCCC1c1c[nH]c2ccccc12)c1c[nH]c2ccccc12]

The compound 6a (205 mg, 0.55 mmol) was obtained from amine 11a (200 mg, 1.0 mmol) and oxoacetyl chloride (8a) (249 mg, 1.2 mmol). Yield: 55%.

IR (neat): 3270, 2930, 2850, 1600, 1520, 1460, 1420, 1240, 1125, 945, 740 cm$^{-1}$. $^1$H NMR (300 MHz, CDCl$_3$): δ=1.40-1.68 (m, 4H), 1.70-1.82 (m, 1H), 2.23 (d, J=13.4 Hz, 1H), 2.95-3.01 (m, 1H), 3.40 (d, J=13.4 Hz, 1H), 6.16 (d, J=4.8 Hz, 1H), 6.92-7.19 (m, 6H), 7.23-7.25 (m, 2H), 7.69-7.75 (m, 2H), 8.16-8.21 (m, 1H), 9.23 (br s, 1H) ppm. $^{13}$C NMR (75 MHz, CDCl$_3$): 6=24.3, 30.4, 32.3, 46.9, 49.8, 115.3, 116.1, 117.1, 117.9, 123.3, 125.7, 126.0, 126.9, 127.2, 127.4, 128.0, 129.1, 130.3, 139.9, 140.4, 140.5, 140.8, 170.8, 190.7 ppm. LRMS (ESI): m/z (%)=394 (100) [(M+Na)$^+$].

1-(3-(1H-Indol-3-yl)morpholino)-2-(1H-indol-3-yl)ethane-1,2-dione 6b

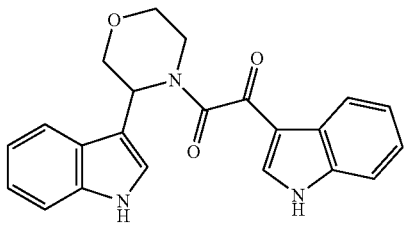 [SMILES: O=C(C(=O)N1CCOCC1c1c[nH]c2ccccc12)c1c[nH]c2ccccc12]

The compound 6b (230 mg, 0.617 mmol) was obtained from amine 11b (202 mg, 1.0 mmol) and oxoacetyl chloride (8a) (249 mg, 1.2 mmol). Yield: 62%.
IR (neat): 3270, 2960, 2920, 2840, 1605, 1520, 1455, 1420, 1240, 1115, 1060, 940, 740 cm$^{-1}$.
$^1$H NMR (300 MHz, CD$_3$OD): δ=3.28-3.39 (m, 2H), 3.60 (td, J=3.4 and 11.3 Hz, 1H), 3.81 (dd, J=2.4 and 11.7 Hz, 1H), 3.99 (dd, J=3.4 and 11.7 Hz, 1H), 4.39 (d, J=11.7 Hz, 1H), 5.96 (d, J=2.7 Hz, 1H), 7.10 (t, J=7.1 Hz, 1H), 7.17 (t, J=7.1 Hz, 2H), 7.23 (t, J=7.1 Hz, 1H), 7.42 (dd, J=2.4 and 8.0 Hz, 1H), 7.61 (s, 1H), 7.75 (s, 1H), 7.94 (d, J=8.0 Hz, 1H), 8.15 (d, J=7.5 Hz, 1H) ppm. $^{13}$C NMR (75.5 MHz, CD$_3$OD): δ=43.6, 46.9, 68.5, 71.3, 112.5, 112.9, 113.3, 114.9, 120.3, 120.4, 122.5, 123.0, 124.1, 125.2, 126.4, 126.5, 127.9, 137.7, 137.8, 138.6, 167.9, 187.5 ppm. LRMS (ESI): m/z (%)=396 (100) [(M+Na)$^+$].

tert-Butyl 4-(2-(1H-indol-3-yl)-2-oxoacetyl)-3-(1H-indol-3-yl)piperazine-1-carboxylate 6c

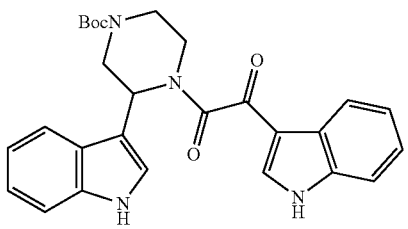 [SMILES: CC(C)(C)OC(=O)N1CCN(C(=O)C(=O)c2c[nH]c3ccccc23)C(c2c[nH]c3ccccc23)C1]

The compound 6c (195 mg, 0.413 mmol) was obtained from amine 11c (301 mg, 1.0 mmol) and oxoacetyl chloride (8a) (249 mg, 1.2 mmol). Yield: 41%.
IR (neat): 3360, 2970, 2920, 2865, 1675, 1610, 1585, 1460, 1430, 1365, 1245, 1155, 1120, 935, 740 cm$^{-1}$. $^1$H NMR (300 MHz, CD$_3$OD): δ=1.42 (s, 9H), 2.87-3.52 (m, 4H), 3.98 (d, J=12.2 Hz, 1H), 4.58-4.72 (m, 1H), 6.13 (br s, 1H) 7.05 (t, J=7.5 Hz, 1H), 7.13 (t, J=7.5 Hz, 2H), 7.16-7.25 (m, 3H), 7.38-7.44 (m, 2H), 7.81 (d, J=7.9 Hz, 1H), 7.92 (s, 1H), 8.19 (d, J=7.5 Hz, 1H) ppm. $^{13}$C NMR (75.5 MHz, CD$_3$OD): δ=28.7 (3C), 47.2, 48.9, 49.1, 49.3, 81.9 (C), 112.6, 113.4, 115.0, 120.2, 120.5, 122.6, 123.2, 124.1, 125.1, 125.3, 126.5, 127.0, 127.7, 137.9, 138.1, 138.7, 156.2, 167.8, 187.4 ppm. LRMS (ESI): m/z (%)=495 (100) [(M+Na)$^+$], 373 (35) [(M-Boc+H)$^+$].

1-(5-Bromo-1H-indol-3-yl)-2-(2-(5-bromo-1H-indol-3-yl)piperidin-1-yl)ethane-1,2-dione 6d

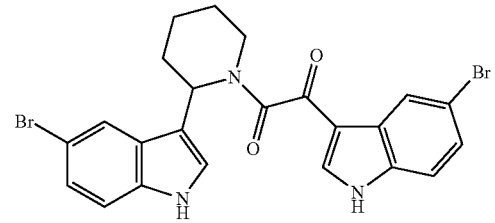 [SMILES: O=C(C(=O)N1CCCCC1c1c[nH]c2ccc(Br)cc12)c1c[nH]c2ccc(Br)cc12]

The compound 6d (410 mg, 0.775 mmol) was obtained from amine 11d (279 mg, 1.0 mmol) and oxoacetyl chloride (8b) (344 mg, 1.2 mmol). Yield: 78%.
IR (neat): 3170, 2940, 1610, 1520, 1445, 1430, 1230, 950, 885, 810, 805, 675 cm$^{-1}$. $^1$H NMR (300 MHz, DMSO-d$_6$): δ=1.35-1.59 (m, 2H), 1.60-1.82 (m, 2H), 1.84-2.08 (m, 2H), 2.32-2.36 (m, 1H), 2.85-2.95 (m, 1H), 6.03 (d, J=4.3 Hz, 1H), 7.24 (dd, J=1.9 and 8.6 Hz, 1H), 7.37-7.45 (m, 2H), 7.50-7.54 (m, 2H), 7.83 (d, J=1.9 Hz, 1H), 8.16 (s, 1H), 8.25-8.28 (m, 2H), 11.32 (br s, 1H). $^{13}$C NMR (75.5 MHz, DMSO-d$_6$): δ=20.5, 26.4, 28.2, 42.6, 45.2, 112.1, 112.5, 113.1, 114.1, 115.3, 115.8, 121.7, 123.6, 124.3, 126.4, 126.8, 127.1, 128.5, 135.5, 136.2, 137.6, 166.0, 186.7 ppm. LRMS (ESI): m/z (%)=550 (42), 552 (84) and 554 (42) [(M+Na)$^+$], 304 (100) and 306 (100) [(M C$_{10}$H$_5$BrO$_2$+Na)$^+$].

1-(5-Bromo-1H-indol-3-yl)-2-(3-(5-bromo-1H-indol-3-yl)morpholino)ethane-1,2-dione 6e

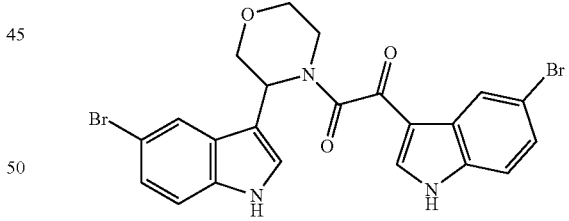

The compound 6e (380 mg, 0.716 mmol) was obtained from amine 11e (281 mg, 1.0 mmol) and oxoacetyl chloride (8b) (344 mg, 1.2 mmol). Yield: 72%.
IR (neat): 3290, 2900, 2865, 1635, 1615, 1520, 1445, 1420, 1295, 1230, 1145, 1100, 940, 880, 790, 745 cm$^{-1}$. $^1$H NMR (300 MHz, DMSO-d$_6$): δ=3.22-3.29 (m, 1H), 3.48 (td, J=3.0 and 11.2 Hz, 1H), 3.83 (dd, J=2.5 and 11.2 Hz, 1H), 3.99 (dd, J=3.5 and 11.8 Hz, 1H), 4.07-4.14 (m, 1H), 4.36 (d, J=11.8 Hz, 1H), 5.78 (d, J=2.5 Hz, 1H), 7.25 (dd, J=1.9 and 8.6 Hz, 1H), 7.39-7.44 (m, 2H), 7.50 (s, 1H), 7.62 (d, J=2.4 Hz, 1H), 7.94 (d, J=1.9 Hz, 1H), 8.09 (s, 1H), 8.23 (d, J=1.7 Hz, 1H), 11.35 (br s, 1H), 12.53 (br s, 1H) ppm. $^{13}$C NMR (75.5 MHz, DMSO-d$_6$): δ=41.9, 44.4, 66.8, 69.4, 111.3, 111.6, 112.6, 113.6, 114.7, 115.3, 121.2, 123.0, 123.8, 126.3, 126.6, 126.8, 128.1, 134.6, 135.6, 137.4, 165.0, 185.4 ppm. LRMS (ESI): m/z (%)=552, 554 (100) and 556 [(M+Na)+], 530, 532 (29) and 534 [(M+H)+].

tert-Butyl 3-(5-bromo-1H-indol-3-yl)-4-(2-(5-bromo-1H-indol-3-yl)-2-oxoacetyl) piperazine-1-carboxylate 6f

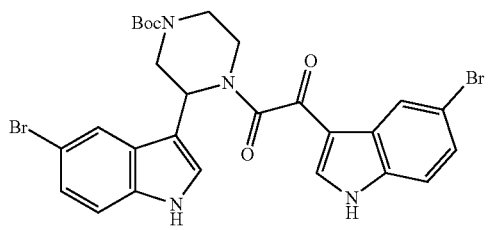 [SMILES: CC(C)(C)OC(=O)N1CCN(C(=O)C(=O)c2c[nH]c3ccc(Br)cc23)C(c2c[nH]c3ccc(Br)cc23)C1]

The compound 6f (416 mg, 0.66 mmol) was obtained from amine 11f (380 mg, 1.0 mmol) and oxoacetyl chloride (8b) (344 mg, 1.2 mmol). Yield: 66%.

IR (neat): 3275, 2970, 2925, 2855, 1675, 1615, 1445, 1420, 1365, 1235, 1160, 1125, 885 cm$^{-1}$.

$^1$H NMR (300 MHz, CDCl$_3$): δ=1.31 (s, 9H), 2.81-2.99 (m, 2H), 3.17-3.41 (m, 2H), 3.78-3.85 (m, 1H), 4.43-4.59 (m, 1H), 5.90 (br s, 1H), 6.91-7.19 (m, 6H), 7.79 (s, 1H), 8.26 (s, 1H), 8.68 (br s, 1H), 10.04 (br s, 1H) ppm. $^{13}$C NMR (75.5 MHz, CDCl$_3$): δ=28.4 (3C), 41.7, 41.3, 45.7, 60.5, 80.9 (C), 111.5, 112.9, 113.0, 113.2, 113.4, 113.9, 116.9, 121.7, 124.5, 125.2, 126.8, 127.3, 127.9, 134.9, 135.2, 136.5, 154.7, 166.0, 185.0 ppm. LRMS (ESI): m/z (%)=651, 653 (100) and 655 [(M+Na)+].

Example 11

Synthesis of bis-indole 7

1-(5-bromo-1H-indol-3-yl)-2-(2-(5-bromo-1H-indol-3-yl)piperazin-1-yl)ethane-1,2-dione hydrochloride 7

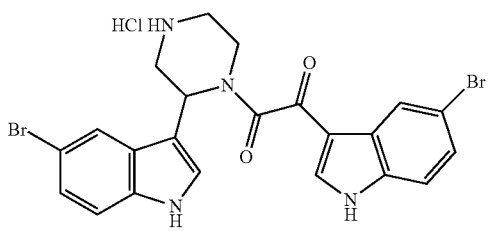

A cold solution of hydrochloric acid was prepared by reaction of freshly distilled acetyl chloride (0.143 mL, 157 mg, 2.0 mmol) with 3 mL of dry methanol. This solution was stirred at 0° C. during 15 min and was then added to a solution of bis-indole 6f (126 mg, 0.2 mmol) in 2 mL of dry methanol. The resulting mixture was stirred during 2 hours at room temperature. Methanol was then slowly evaporated under vacuum (t<20° C.) till 1 mL. The saturated solution then was added dropwise to 50 mL of ether and the solid precipitate was filtered off and dried under vacuum. The bis-indolic amine salt 7 (80 mg, 0.14 mmol) was obtained as a rose-grey solid. Yield: 71%.

IR (neat): 3205, 2930, 1615, 1445, 1425, 1230, 1145, 1105, 885, 780 cm$^{-1}$. $^1$H NMR (300 MHz, CDCl$_3$): δ=2.78-2.92 (m, 2H), 3.08-3.37 (m, 2H), 3.81-3.89 (m, 1H), 4.36-4.55 (m, 1H), 5.92 (br s, 1H), 6.81-7.07 (m, 6H), 7.79 (s, 1H), 8.27 (s, 1H), 8.70 (br s, 1H), 10.05 (br s, 1H) ppm.

$^{13}$C NMR (75.5 MHz, CDCl$_3$): δ=41.3, 41.4, 45.3, 60.1, 110.8, 112.0, 112.6, 112.8, 113.0, 113.5, 116.5, 121.3, 124.1, 124.8, 126.4, 126.9, 127.5, 134.5, 134.8, 136.1, 165.6, 184.6 ppm. LRMS (ESI): m/z (%)=529, 531 (100) and 533 [(M+H)+].

Experimental Part

Biology

Example 12

Evaluation of the Antibacterial Activity and NorA Efflux Pump Inhibition 12.1: Determinaton of the Minimum Inhibitory Concentration (MIC)

The microdilution method recommended by the Clinical and Laboratory Standard Institute [M07-A8, Vol. 29, N° 2] was used. The activity of indolic compounds was tested against 29 bacterial strains belonging to 17 different species and 12 different genera (*Staphylococcus, Streptococcus, Enterococcus, Listeria, Bacillus, Haemophilus, Escherichia, Klebsiella, Enterobacter, Serratia, Pseudomonas*, and *Acinetobacter*). Bacterial inocula were prepared in Mueller Hinton broth (MH2, bioMerieux, Marcy L'Etoile, France), supplemented with 10% sheep blood for fastidious species (i.e., *Streptococcus pneumoniae* and *Haemophilus influenzae*). They were dispensed in 96 well microtiter plates (5×10$^5$ CFU/ml of final inoculum). Indolic compounds were added to the wells as to obtain two-fold serial concentrations (0.50-128 mg/L of final concentrations). Plates were incubated at 37° C. in ambient air, or at 37° C. in 5% CO$_2$ enriched atmosphere for fastidious species. MICs were read after 18 hours incubation of cultures, and corresponded to the minimum indolic compound concentration that allowed complete visual growth inhibition of bacteria. Drug-free cultures served as growth controls. Cultures receiving gentamicin, ciprofloxacin or cefotaxime served as positive controls.

The results are given in the following Table I-1:

Compounds of the invention present a strong intrinsic antibacterial activity, in particular against *Staphylococcus aureus* and *Staphylococcus epidermidis*.

Further, compounds of the invention present an anti-*Staphylococcus* activity even against strains presenting an acquired resistance to beta-lactams, including methicillin-resistant *Staphylococcus aureus* (MRSA) strains such as CIP65.25 (MetiR) and ATCC 33592 (MetiR), and/or to glycopeptides such as the VISA (vancomycin-intermediate *S. aureus*) strain ATCC 106414. These multi-resistant bacterial strains are frequently implicated in severe hospital infections.

The lack of intrinsic antibacterial activity of compounds 12, 12a, 13 and 14 shows that the presence of the bis-indoles moieties is essential for the antibacterial activity of the compounds of the invention.

TABLE I-1

| | Compound | | | | | | | | | | | | |
|---|---|---|---|---|---|---|---|---|---|---|---|---|---|
| | 2 | 3 | 4 | 5 | 6a | 6b | 6c | 6d | 6f | 12 | 12a | 13 | 14 |
| *Staphylococcus* (Micrococcaceae Gram+) | | | | | | | | | | | | | |
| S. aureus ATCC 25923 | >128 | 4 | 1.6 | 1 | >128 | >128 | >128 | >128 | >128 | >128 | >128 (>32) | >128 | >128 |
| S. aureus ATCC 29213 | >128 | 2 | 0.8 | 1 | >128 | >128 | >128 | 2-4 | 2-4 | >128 | >32 | 128 | 64 |
| S. aureus ATCC 9144 | >128 | 4 | 0.8 | 1 | >128 | >128 | >128 | >128 | >128 | >128 | >32 | >128 | >128 |
| S. aureus ATCC 6538 | >128 | 4 | 0.8 | 1 | >128 | >128 | >128 | >128 | >128 | >128 | >32 | 64 | 128 |
| S. aureus CIP 65.6 | >128 | 4 | 0.8 | 2 | >128 | >128 | >128 | >128 | >128 | >128 | >32 | >128 | 128 |
| S. aureus CIP 103428 | >128 | 4 | 1.6 | 1 | >128 | >128 | >128 | >128 | >128 | >128 | >32 | 64 | 128 |
| S. aureus CIP 65.25 (MRSA) | >128 | 4 | 1.6 | 1 | >128 | >128 | >128 | >128 | >128 | >128 | >32 | >128 | 128 |
| S. aureus ATCC 33592 (MRSA) | >128 | 4 | 0.8 | 1 | >128 | >128 | >128 | >128 | >128 | >128 | >32 | >128 | 128 |
| S. aureus ATCC 106414 (VISA) | >128 | 4 | 0.8 | 1 | >128 | >128 | >128 | >128 | >128 | >128 | >32 | >128 | 128 |
| S. epidermidis ATCC 12228 | >128 | 4 | 0.8 | 2 | >128 | >128 | >128 | >128 | >128 | >128 | >32 | >128 | >128 |
| S. epidermidis CIP 81.55 | >128 | 8 | 1.6 | 2 | >128 | >128 | >128 | >128 | >128 | >128 | >32 | >128 | >128 |
| S. epidermidis CIP 103627 | >128 | >16 | 1.6 | 2 | >128 | >128 | >128 | >128 | >128 | >128 | >32 | >128 | >128 |
| S. aureus SA-1199B | >128 | 4 | 1.6 | 2 | >128 | >128 | >128 | >128 | >128 | >128 | >32 | 64 | 128 |
| *Streptococcus* and *Enterococcus* (Streptococcaceae Gram+) | | | | | | | | | | | | | |
| S. pneumoniae ATCC 49619 | >128 | >128 | — | 32 | >128 | >128 | >128 | >128 | >128 | >128 | | 128 | >128 |
| S. pneumoniae ATCC 6303 | >128 | 64 | — | 32 | >128 | >128 | >128 | >128 | >128 | >128 | 128 | 128 | >128 |
| S. agalactiae (group B) ATCC 12400 | >128 | 64 | — | 64 | >128 | >128 | >128 | >128 | >128 | >128 | 64 | 128 | >128 |
| S. pyogenes (group A) CIP 104226 | >128 | 128 | — | 32 | >128 | >128 | >128 | >128 | >128 | >128 | >128 | 128 | >128 |
| S. mitis CIP 103335 | >128 | >128 | — | 64 | >128 | >128 | >128 | >128 | >128 | >128 | >128 | >128 | >128 |
| E. faecium CIP 54.32 | >128 | 32 | — | 64 | >128 | >128 | >128 | >128 | >128 | >128 | >128 | >128 | >128 |
| E. faecalis ATCC 29212 | >128 | >128 | — | 128 | >128 | >128 | >128 | >128 | >128 | >128 | >128 | >128 | >128 |
| *Listeria* (Listeriaceae Gram+) | | | | | | | | | | | | | |
| Listeria innocua CIP 80.11 | >128 | >128 | — | 64 | >128 | >128 | >128 | >128 | >128 | >128 | >128 | >128 | >128 |
| *Bacillus* (Bacillaceae Gram+) | | | | | | | | | | | | | |
| Bacillus subtilis CIP 5262 | >128 | 128 | — | 64 | >128 | >128 | >128 | >128 | >128 | >128 | >128 | 128 | 128 |
| Enterobacteriaceae (Gram−) | | | | | | | | | | | | | |
| Escherichia coli ATCC 25922 | >128 | >128 | >128 | >128 | >128 | >128 | >128 | >128 | >128 | >128 | | >128 | >128 |
| Klebsiella pneumoniae ATCC 35657 | >128 | >128 | >128 | >128 | >128 | >128 | >128 | >128 | >128 | >128 | 64 | >128 | >128 |
| Enterobacter cloacae ATCC 13047 | >128 | >128 | >128 | >128 | >128 | >128 | >128 | >128 | >128 | >128 | | >128 | >128 |
| Serratia marcescens CIP 103551 | >128 | >128 | >128 | >128 | >128 | >128 | >128 | >128 | >128 | >128 | | >128 | >128 |
| Pseudomonadaceae (Gram−) | | | | | | | | | | | | | |
| Pseudomonas aeruginosa CIP 5933 | >128 | >128 | >128 | >128 | >128 | >128 | >128 | >128 | >128 | >128 | >128 (>32) | >128 | >128 |
| *Acinetobacter* (Moraxellaceae Gram−) | | | | | | | | | | | | | |
| Acinetobacter baumanii ATCC 19606 | >128 | >128 | >128 | >128 | >128 | >128 | >128 | >128 | >128 | >128 | >128 (>32) | >128 | >128 |
| *Haemophilus* (Pasteurellaceae Gram−) | | | | | | | | | | | | | |
| Haemophilus influenzae ATCC 49766 | >128 | 32 | — | 32 | >128 | >128 | >128 | >128 | >128 | >128 | | >128 | >128 |

MRSA: methicillin-resistant *Staphylococcus aureus*
VISA: vancomycin intermediate *Staphylococcus aureus*

12.2: Determinaton of the Minimum Inhibitory Concentration (MIC) of Compounds 4 and 5 Against a Large Panel of *Staphylococcus* Strains (Table I-2):

MICs Determination

We used the previously described protocol, with subtle modifications. The microdilution method recommended by the Clinical and Laboratory Standard Institute [M07-A9, Vol. 32, N° 2] was used. The activity of bis-indolic compounds was tested against 35 bacterial strains belonging to 12 different *Staphylococcus* species.

Bacterial inocula were prepared in Mueller Hinton broth (MH2, BioMerieux, Marcy L'Etoile, France). They were dispensed in 96 well microtiter plates ($5 \times 10^5$ CFU/ml of final inoculum, 192 µL per well). Indolic compounds diluted in pure DMSO (8 µL per well, concentrated 25 times) were added to the wells as to obtain two-fold serial concentrations (0.5-32 mg/L of final concentrations). The final concentration of DMSO was 4% in each well.

To avoid cross-contaminations in microtiter plates, one row was left blank between each strain tested. Microplates were incubated for 18 h at 37° C. in ambient air or at 37° C. in 5% $CO_2$ enriched atmosphere for fastidious species. Then MICs were read visually and, in case of visual reading difficulties, confirmed using a spectrophotometer at a wavelength of 630 nm (BioTek® EL808 Absorbance Microplate Reader). MICs corresponded to the minimum bis-indolic compound concentration that allowed complete visual growth inhibition of bacteria. Drug-free cultures served as growth controls.

Bacterial Strains

We used four *Staphylococcus aureus* strains. Two reference strains were provided by the French reference center for *Staphylococcus* spp. (Lyon, France), including one methicillin-susceptible (MSSA 476) and one methicillin-resistant (MRSA 252) *S. aureus* strains. The two remaining *S. aureus* strains were purchased from the CRBIP (Centre de Ressources Biologiques de l'Institut Pasteur): a vancomycin-intermediate strain (ATCC 106414) and a *S. aureus* strain (SA-1199B) resistant to fluoroquinolones due to overexpression of the NorA multidrug efflux pump.

Coagulase-negative *Staphylococcus* strains included three reference strains purchased from CRBIP: a methicillin-susceptible *S. epidermidis* strain (ATCC 12228), a methicillin-resistant *S. epidermidis* strain (ATCC 49461), and a methicillin-susceptible *S. sciuri* strain (ATCC 29061). We also used clinical strains belonging to the following coagulase-negative *Staphylococcus* species: *S. auricularis* (two strains), *S. warneri* (five strains), *S. capitis* (five strains), *S. haemolyticus* (four strains), *S. hominis* (seven strains), *S. cohnii* (two strains), and *S. saprophyticus*, *S. caprae* and *S. simulans* (one strain each). Identification of the clinical strains was obtained using VITEK® 2 System (Biomérieux). The results are presented in Table I-2 below:

TABLE I-2

| | Compounds | |
|---|---|---|
| *Staphylococcus* (Micrococcaceae Gram+) | 4 | 5 |
| *Staphylococcus aureus* ATCC 106414 (VISA) | 1 | 1 |
| *Staphylococcus aureus* MRSA 252 | 1 | 2 |
| *Staphylococcus aureus* MSSA 476 | 1 | 2 |
| *Staphylococcus aureus* SA-1199B (NorA) | 1 | 2 |
| *Staphylococcus auricularis* (CHUG-Saur1) | 1 | 1 |
| *Staphylococcus auricularis* (CHUG-Saur3) | 1 | 1 |
| *Staphylococcus capitis* (CHUG-Scap1) | 1 | 2 |
| *Staphylococcus capitis* (CHUG-Scap5) | 1 | 2 |
| *Staphylococcus capitis* (CHUG-Scap4) | 1 | 1 |
| *Staphylococcus capitis* (CHUG-Scap6) | 1 | 1 |
| *Staphylococcus capitis* (CHUG-Scap7) | 1 | 2 |
| *Staphylococcus caprae* (CHUG-Scapra1) | 1 | 2 |
| *Staphylococcus cohnii* (CHUG-Scoh1) (MRSA) | 1 | 2 |
| *Staphylococcus cohnii* (CHUG-Scoh2) | 2 | 2 |
| *Staphylococcus epidermidis* ATCC 12228 | 1 | 2 |
| *Staphylococcus epidermidis* ATCC 49461 | 1 | 2 |
| *Staphylococcus haemolyticus* (CHUG-Shae1) | 1 | 4 |
| *Staphylococcus haemolyticus* (CHUG-Scap5) | 1 | 4 |
| *Staphylococcus haemolyticus* (CHUG-Scap4) | 2 | 4 |
| *Staphylococcus haemolyticus* (CHUG-Scap6) | 2 | 4 |
| *Staphylococcus hominis* (CHUG-Shom1) | 2 | 4 |
| *Staphylococcus hominis* (CHUG-Shom6) | 1 | 2 |
| *Staphylococcus hominis* (CHUG-Shom4) | 1 | 2 |
| *Staphylococcus hominis* (CHUG-Shom7) | 1 | 2 |
| *Staphylococcus hominis* (CHUG-Shom5) | 1 | 1 |
| *Staphylococcus hominis* (CHUG-Shom3) | 1 | 2 |
| *Staphylococcus hominis* (CHUG-Shom8) | 1 | 2 |
| *Staphylococcus saprophyticus* (CHUG-Ssap2) | 1 | 2 |
| *Staphylococcus sciuri* ATCC 29061 | 2 | 4 |
| *Staphylococcus simulans* (CHUG-Ssim1) | 1 | 2 |
| *Staphylococcus warneri* (CHUG-Swar1) | 1 | 2 |
| *Staphylococcus warneri* (CHUG-Swar5) | 1 | 1 |
| *Staphylococcus warneri* (CHUG-Swar4) | 1 | 2 |
| *Staphylococcus warneri* (CHUG-Swar6) | 1 | 2 |
| *Staphylococcus warneri* (CHUG-Swar7) | 1 | 2 |

MRSA: methicillin-resistant *Staphylococcus aureus*
VISA: vancomycin intermediate *Staphylococcus aureus*
NorA: overexpression of NorA efflux pump 12.2: Determination of the Minimum Bactericidal Concentration (MBC)

The MBC was determined using a macro-method. Sterile tubes were filled with a primary bacterial inoculum prepared in Mueller Hinton broth as above ($10^6$ CFU/mL of final inoculum) and indolic compounds were added at twofold serial concentrations (0.25-64 mg/L of final concentrations). After 18 hours incubation of cultures, ten-fold serial dilutions of the cultures with no visible bacterial growth were prepared, and 100 µl of each dilution were inoculated to Mueller Hinton agar media for 24-48 hours. CFU counts were then determined and the MBC corresponded to the minimal indolic compound concentration for which 99.9% or more bacterial cells were killed after 18 hours of incubation.

12.3: Determination of the Killing Curves

The method described by Motyl et al. [M. Motyl, K. Dorso, J. Barrett, R. Giacobbe, Basic Microbiological Techniques Used in Antibacterial Drug Discovery. *Current Protocols in Pharmacology*. UNIT 13A.3. January, 2006] was used.

Killing curves corresponded to the measure of the kinetic of bactericidal activity of indolic compounds over time (time-kill curves) or after 18 h incubation of cultures according to different drug concentrations (concentration-killing curves). Sterile tubes were inoculated with: 1/ sterile Mueller Hinton broth, to serve as negative control; 2/ a drug-free bacterial inoculum, to serve as a growth control; 3/ a bacterial inoculum ($10^5$ CFU/ml of final concentration) with various concentrations of the tested indolic compound. The tubes were incubated at 37° C. with agitation (50 rpm). Bacterial inocula are determined in each tube using the CFU count method at the beginning of the experiments, and then after 18 h for concentration-killing curves, or after 1 h, 2 h, 4 h, 8 h and 18 h for time-kill curves. A significant bactericidal effect corresponds to reduction of the initial bacterial load of 3 logs or more at any time of incubation.

12.4: Determination of the Mutation Frequency

The mutation frequency is the number of individuals in a population with a particular mutation. In the present case, the mutation frequency was determined for a specific bacterial species and a specific indolic compound. Mueller Hinton agar plates containing various indolic compound concentrations, i.e., MIC×2, MIC×4, MIC×8, and MIC×16 were prepared. These plates were inoculated with various bacterial suspensions: $10^7$, $10^8$ or $10^9$ UFC/ml. After 24 hours incubation of media at 37° C., CFU were numerated. The mutation frequency corresponded to the ratio of resistant mutants counted on a specific plate to the CFU count of the primary inoculum, expressed as a percentage.

The mutation frequency was determined for *S. aureus* ATCC 25923 strain.

12.5: In Vitro Selection of Resistant Mutants.

In vitro mutant strains that resisted to the most active indolic compounds were selected. A bacterial inoculum ($5 \times 10^4$ CFU/mL) was prepared in Mueller Hinton broth and dispensed in a 24-well microtiter plate (1 ml per well). Each row received two-fold serial concentrations of the tested indolic compound (1/2 to 16 times the MIC of the wild-type strain). Plates were incubated 72-96 hours, and bacterial growth obtained in the well with the highest indolic compound concentration were harvested, diluted 1/40 and dispensed in a new 24-well microtiter plate with increased drug concentrations (1/2 to 16 times the new MIC).

The procedure was repeated several fold until we obtained high-level resistant mutants. The final and intermediate resistant mutant populations were all kept frozen at −80° C. for later analysis.

Several independent mutant strains with acquired resistance to indolic compounds in *S. aureus* and in *S. epidermidis* strains have been selected. Selection of resistance was slow and difficult to obtain, but high-level resistant mutants (MIC of 64-128 mg/L) could be isolated. These mutants have been used to better characterize the mode of action of indolic compounds and resistance mechanisms that may be developed by *Staphylococcus* species to resist the action of these new antibiotics.

12.6: Determination of Antibacterial Activity as Efflux Pump Inhibition

The efflux pump inhibition potential of the bis-indolic derivatives was tested using two steps. In a first step, the intrinsic antibacterial activity of the compounds was assayed against the following strains:

*Staphylococcus aureus* (ATCC 25923), *Staphylococcus aureus* 1199B, which is resistant to fluoroquinolones due notably to the overexpression of the NorA efflux pump (G. W. Kaatz, S. M. Seo, *Antimicrob. Agents Chemother.* 1995, 39, 2650-2655) and *Staphylococcus aureus* K2378 which overexpresses the efflux pump NorA from a multicopy plasmid (S. Sabatini, G. W. Kaatz, G. M. Rossolini, D. Brandini, A. Fravolini *J. Med. Chem.* 2008, 51, 4321-4330).

The following experimental protocol was used: indolic derivatives (initially solubilised in DMSO at 10 mg/mL) were dispensed in a 96-wells microplate by two fold serial dilutions in Muller-Hinton medium (MH, Bio Rad) using a Biomek 2000 (Beckman) handling robot. 100 μL of the bacterial inoculum (an overnight culture at 37° C. in 5 mL MH diluted 100-fold) was then added in each well. The total volume was 200 μL in each well and the final bacteria concentration $10^6$ CFU/mL (CFU: colony forming unit). The highest final indolic derivative concentration was 128 mg/L. Growth was assayed with a microplate reader by monitoring absorption at 620 nm after 1, 2, 5, 7 and 24 h incubation at 37° C. In addition, the plates were read visually after 24 hours incubation. Cultures containing 5 μL DMSO were used as growth controls. In addition, two controls containing a sub-inhibitory or a inhibitory antibiotic concentration for the tested strain were performed. The antibiotics used were ampicillin (0.5 and 32 μg/mL) for *E. coli*, kanamycin (0.5 and 16 μg/mL) for *S. aureus* ATCC 25923, ciprofloxacin (4 and 64 mg/L) for *S. aureus* 1199B, ciprofloxacin (0.5 and 2 mg/L) for *S. aureus* K2378. All experiments were performed in duplicate.

In spite of slight differences in the experimental protocol, all compounds described in the present invention showed similar antibacterial activity (at most a 4-fold difference was observed between MIC values) using the experimental procedure described in paragraph 9.1 and in the present paragraph).

Efflux pump inhibition assays were then performed against resistant *Staphylococcus aureus* strains SA 1199B and SA K2378 for bis-indolic derivatives. A serial dilution method was used to test the bis-indolic compounds (maximal concentration 128 mg/L) in the presence of a sub-inhibitory concentration of the ciprofloxacin (4 mg/L, MIC/4 and 2 mg/L, MIC/8) or less for SA 1199B and ciprofloxacin (0.5 mg/L, MIC/4 and 0.25 mg/L, MIC/8) for SA K2378. The minimal inhibitory concentration (MIC) of the bis-indolic compound allowing a complete inhibition of the bacterial growth in the presence of ciprofloxacin was determined. Results are presented in table II:

TABLE II

| | CMI, mg/L (Ciprofloxacin concentration, mg/L) | |
|---|---|---|
| Compounds | *Staphylococcus aureus* 1199B | *Staphylococcus aureus* K2378 |
| 2 | 0.5 (4) | — |
| | 2 (2) | |
| 6a | <0.125 (4) | 8 (0.25) |
| 6b | 0.5 (4) | 16 (0.25) |
| 6c | 0.25 (4) | 16 (0.25) |
| 6d | <0.125 (4) | 8 (0.25) |
| 6f | <0.25 (4) | 1 (0.25) |
| | | 1 (0.5) |

12.7 Cytotoxicity Determination of the Compound of the Invention

In vitro cytotoxicity was assayed on three cell lines—KB (human mouth carcinoma), MCR5 (human lung fibroblast) and HCT116 (human colon tumor). Results are presented in table III as % of cellular growth inhibition in presence of $10^{-5}$ M and $10^{-6}$ M of the tested bis-indolic derivatives.

$IC_{50}$ are presented in table IV.

TABLE III

| Compounds | KB $10^{-5}$ M ($10^{-6}$ M) | MRC5 $10^{-5}$ M (10–6 M) | HCT116 10–5 M ($10^{-6}$ M) |
|---|---|---|---|
| 2 | 97 ± 1 (33 ± 8) | 100 ± 2 (10 ± 5) | 96 ± 1 (53 ± 4) |
| 3 | 100 ± 1 (4 ± 3) | 98 ± 1 (0 ± 3) | 97 ± 1 (0 ± 13) |
| 4 | 76 ± 5 (0 ± 7) | 51 ± 9 (0 ± 3) | 58 ± 4 (0 ± 9) |
| 5 | 91 ± 3 (0 ± 11) | 85 ± 2 (6 ± 3) | 80 ± 3 (10 ± 6) |
| 6a | 20 ± 13 (0 ± 18) | 28 ± 9 (0 ± 15) | 37 ± 6 (0 ± 5) |
| 6b | 9 ± 4 (0 ± 8) | 15 ± 11 (0 ± 3) | 21 ± 10 (2 ± 13) |
| 6c | 66 ± 8 (0 ± 8) | 6 ± 16 (0 ± 17) | 53 ± 3 (8 ± 2) |
| 6d | 53 ± 5 (0 ± 19) | 0 ± 3 (0 ± 26) | 41 ± 4 (4 ± 13) |
| 6e | 29 ± 6 (0 ± 2) | 0 ± 10 (0 ± 12) | 24 ± 6 (3 ± 8) |
| 6f | 92 ± 3 (0 ± 13) | 39 ± 4 (0 ± 12) | 81 ± 2 (0 ± 4) |
| 7 | 4 ± 11 (0 ± 3) | 0 ± 12 (0 ± 14) | 22 ± 7 (0 ± 8) |

$IC_{50}$ from 100 M to 0.005 M on HCT116 in DMSO Duplicate

TABLE IV

| Compound | HCT116 $IC_{50}$ |
|---|---|
| 4 | 4.55/6.07 |
| 5 | 10.1/10.3 |

The invention claimed is:

1. A pharmaceutical composition comprising a compound of formula I, or a pharmaceutically acceptable salt thereof, in association with a pharmaceutically acceptable vehicle,

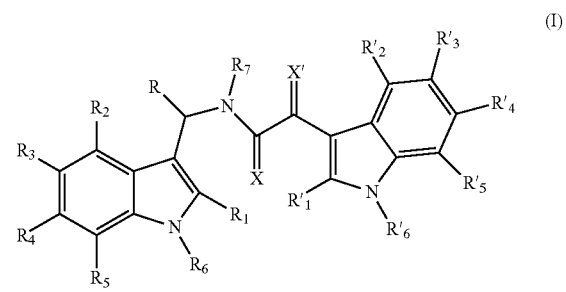

(I)

wherein:
X and X' represent independently from each other O or S, and (a) $R_1$, $R_2$, $R_3$, $R_4$, $R_5$, $R'_1$, $R'_2$, $R'_3$, $R'_4$ and $R'_5$ represent independently from each other:

H, a linear or branched ($C_1$-$C_7$)alkyl optionally substituted by: a halogen, a hydroxyl group, a $OR_a$ or $NR_aR_b$, wherein $R_a$ and $R_b$ represent: H, a linear or branched ($C_1$-$C_7$)-alkyl, ($C_3$-$C_7$)-cycloalkyl, an aryl substituted or not, $CH_2$-aryl, CO—($C_1$-$C_7$)-alkyl, CO-aryl, $CO_2$—($C_1$-$C_7$)-alkyl, $CO_2$-aryl, wherein aryl is a substituted or not aromatic group or a substituted or not heteroaromatic group, a ($C_3$-$C_7$)-cycloalkyl, an aryl substituted or not, $CH_2$-aryl, CO—($C_1$-$C_7$)-alkyl, CO-aryl, $CO_2$—($C_1$-$C_7$)-alkyl, $CO_2$-aryl, wherein aryl is a substituted or not aromatic group or a substituted or not heteroaromatic group, F, Cl, Br, I, $CF_3$, OH, $OR_a$, $OCF_3$, $COCF_3$, $NH_2$, $NHR_a$, $NR_aR_b$, wherein $R_a$ and $R_b$ represent: H, a linear or branched ($C_1$-$C_7$)-alkyl, a ($C_3$-$C_7$)-cycloalkyl, an aryl substituted or not, $CH_2$-aryl, CO—($C_1$-$C_7$)-alkyl, CO-aryl, $CO_2$—($C_1$-$C_7$)-alkyl, $CO_2$-aryl, wherein aryl is a substituted or not aromatic group or a substituted or not heteroaromatic group, CN and $NO_2$, provided that $R_1$, $R_2$, $R_3$, $R_4$, $R_5$, $R'_1$ are different from CN and $NO_2$, $(CH_2)_n$—Z, —$(CH_2)_n$—OH, —$(CH_2)_n$—$CO_2(C_1$-$C_7)$-alkyl, —$(CH_2)_n$—$CO_2$ wherein n=2 to 12, Z is a halogen, and alkyl being as defined above, R represents H, a ($C_1$-$C_7$)-alkyl, $CH_2NHCO_2$—($C_1$-$C_7$)-alkyl, $CH_2NHCO_2$—($C_3$-$C_7$)-cycloalkyl, $CO_2H$, $CO_2$—($C_1$-$C_7$)-alkyl, $CO_2$—($C_3$-$C_7$)-cycloalkyl, $(CH_2)_n$OH, $CH_2NH(CH_2)_n$—OH, $CH_2NH(CH_2)_n$—$NR_aR_b$, CONH—($C_1$-$C_7$)-alkyl, CONH—($C_3$-$C_7$)-cycloalkyl, CONH-aryl, CONH—$(CH_2)_n$OH, CONH—$(CH_2)_n$$NR_aR_b$, wherein n=2 to 12 and $R_a$, $R_b$, aryl and alkyl being as defined above, $R_6$ and $R'_6$ represent independently from each other H, ($C_1$-$C_7$)-alkyl, $SO_2$aryl, aryl being as defined above, OH, O—($C_1$-$C_7$)-alkyl, CO—($C_1$-$C_7$)-alkyl, CO-aryl, $CH_2NH_2$, $CH_2NHRa$, $CH_2N_aR_b$, $Si(R_c)_3$, the Rc groups being identical or different and representing independently of each other a linear or branched ($C_1$-$C_7$)-alkyl, a ($C_3$-$C_7$)-cycloalkyl, or an aryl, aryl and alkyl being as defined above, and $R_7$ represents H, OH, $OR_a$, $R_a$ being as defined above;

or b) R and $R_7$ are joined together to form a cycle of formula I-a:

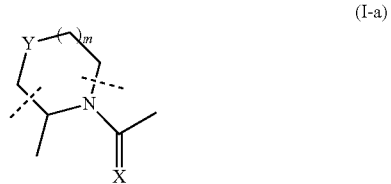

(I-a)

wherein Y represents:
N—$R_8$, wherein $R_8$ represents H, ($C_1C_7$)-alkyl, ($C_3$-$C_7$)-cycloalkyl, CO—($C_1$-$C_7$)-alkyl, CO—($C_3$-$C_7$)-cycloalkyl, $CO_2$—($C_1$-$C_7$)-alkyl, $CO_2$—($C_3$-$C_7$)-cycloalkyl,
O, S,
$CH_2$, $CHR_8$ wherein $R_8$ represents ($C_2$-$C_7$)-alkyl, ($C_3$-$C_7$)-cycloalkyl, CO—($C_1$-$C_7$)-alkyl, CO—($C_3$-$C_7$)-cycloalkyl, $CO_2$—($C_1$-$C_7$)-alkyl, $CO_2$—($C_3$-$C_7$)-cycloalkyl, and m=0, 1 said cycle being optionally substituted by OH, a linear or branched $O(C_1$-$C_7)$-alkyl, a $O(C_3$-$C_7)$-cycloalkyl, $NH_2$, or $NR_aR_b$, $R_a$ and $R_b$ being as defined above, and $R_1$, $R_2$, $R_3$, $R_4$, $R_5$, $R'_1R'_2$, $R'_3$, $R'_4$, $R'_5$, $R_6$ and $R'_6$ being as defined above, or c) R and $R_7$ are joined together to form a cycle of formula I-b:

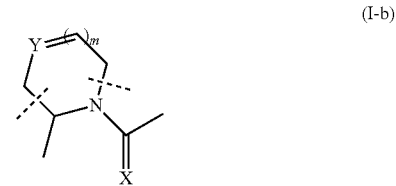

(I-b)

wherein Y represents:
C, $CR_8$, wherein $R_8$ represents ($C_1$-$C_7$)-alkyl, ($C_3$-$C_7$)-cycloalkyl, CO—($C_1$-$C_7$)-alkyl, CO—($C_3$-$C_7$)-cycloalkyl, $CO_2$—($C_1$-$C_7$)-alkyl, $CO_2$—($C_3$-$C_7$)-cycloalkyl, and m=1

$R_1$, $R_2$, $R_3$, $R_4$, $R_5$, $R'_1$, $R'_2$, $R'^3$, $R'^4$, $R'_5$, $R_6$ and $R'_6$ being as defined above, and their pharmaceutically acceptable salts.

2. The pharmaceutical composition according to claim 1, administrable by oral route at a dose of from 10 mg/kg to 200 mg/kg.

3. The pharmaceutical composition according to claim 1, administrable by intravenous route at a dose of from 5 μg/kg to 50 mg/kg.

4. The pharmaceutical composition according to claim 1, further comprising:
at least one antibiotic compound,
said pharmaceutical composition being used for simultaneous or separate use, or use spread over time, intended for the treatment of pathologies associated with bacterial infections for which a resistance to said at least one antibiotic exists.

5. The pharmaceutical composition according to claim 1, wherein:
X and X' are as previously defined,
$R_1$, $R_2$, $R_3$, $R_4$, $R_5$, $R_6$, $R'_1$, $R'_2$, $R'_3$, $R'_4$, $R'_5$ and $R'_6$ are as previously defined,
R represents H, a ($C_1$-$C_7$)-alkyl, $CH_2NHCO_2$—($C_1$-$C_7$)-alkyl, $CH_2NHCO_2$—($C_3$-$C_7$)-cycloalkyl, $CO_2H$, $CO_2$—($C_1$-$C_7$)-alkyl, $CO_2$—($C_3$-$C_7$)-cycloalkyl, $(CH_2)_n$OH, $CH_2NH(CH_2)_n$—OH, $CH_2NH(CH_2)_n$—$NR_aR_b$, CONH—($C_1$-$C_7$)-alkyl, CONH—($C_3$-$C_7$)-cycloalkyl, CONH-aryl, CONH—$(CH_2)_n$OH, CONH—$(CH_2)_n$$NR_aR_b$, wherein n=2 to 12, and $R_a$, $R_b$, aryl and alkyl being as previously defined, and $R_7$ represents H, OH, OR, $R_a$ being as previously defined.

6. The pharmaceutical composition according to claim 1, wherein:
X and X' are as previously defined,
$R_1$, $R_2$, $R_3$, $R_4$, $R_5$, $R_6$ $R'_1$, $R'_2$, $R'_3$, $R'_4$, $R'_5$ and $R'_6$ are as previously defined, and
R and $R_7$ are joined together to form a cycle of formulas (I-a) and (I-b) as previously defined.

7. The pharmaceutical composition according to claim 1, wherein said compound is of formula II:

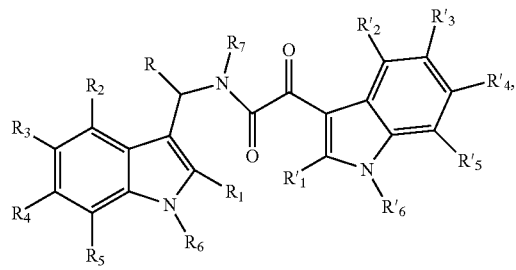

(II)

wherein $R_1, R_2, R_3, R_4, R_5, R_6 R'_1, R'_2, R'_3, R'_4, R'_5$ and $R'_6$ are as previously defined.

8. The pharmaceutical composition according to claim 1, wherein said compound is of formula III:

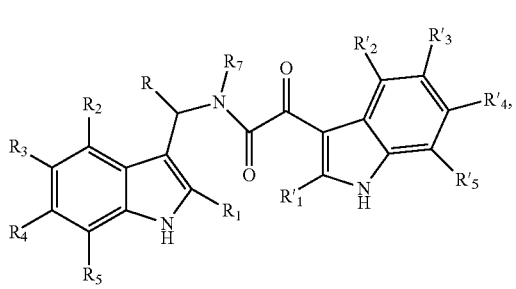

(III)

wherein $R_1, R_2, R_3, R_4, R_6, R_6 R'_1, R'_2, R'_3, R'_4, R'_5$ and R are as previously defined.

9. The pharmaceutical composition according to claim 1, wherein said compound is of formula IV:

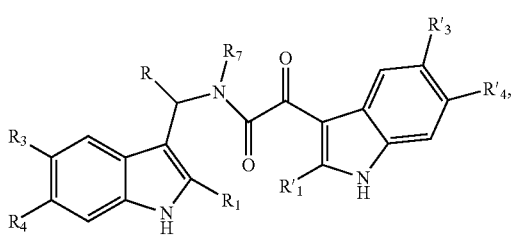

(IV)

wherein $R_1, R_2, R_3, R_4, R_5, R_6 R'_1, R'_2, R'_3, R'_4$ and R are as previously defined.

10. The pharmaceutical composition according to claim 1, wherein said compound is of formula V

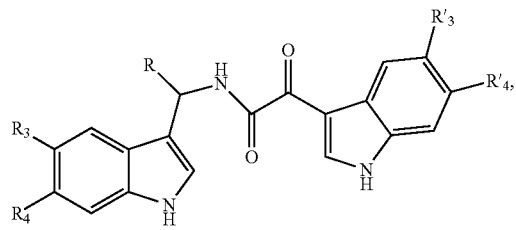

(V)

wherein:
$R_3, R_4, R'_3$ and $R'_4$ each independently represents H, F, Cl, Br, I, and
R represents a $(C_2-C_7)$-alkyl, $CH_2NHCO_2$—$(C_1-C_7)$-alkyl, $CO_2H$, $CO_2$—$(C_1-C_7)$-alkyl, $CONH$—$(CH_2)_n$OH, $(CH_2)_nOH$, $CH_2NH(CH_2)_n$—OH, $CH_2NH(CH_2)_n$—$NR_aR_b$, $CONH$—$(CH_2)_nNR_aR_b$.

11. The pharmaceutical composition according to claim 10, wherein at least one of $R_3, R_4, R'_3$ and $R'_4$ represents F, Cl, Br, I.

12. The pharmaceutical composition according to claim 1, wherein said compound is of general formula VI:

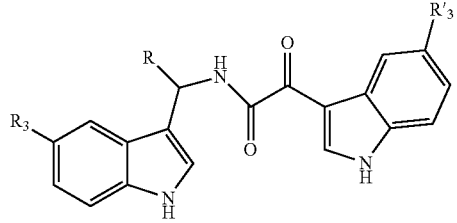

(VI)

wherein:
$R_3$ and $R'_3$ each independently represents H, F, Cl, Br, I, and at least one of $R_3$ and $R'_3$ represents F, Cl, Br, I, and R represents a $(C_1-C_7)$-alkyl, $CH_2NHCO_2$—$(C_1-C_7)$-alkyl, $CO_2H$, $CO_2$—$(C_1-C_7)$-alkyl, $CONH$—$(CH_2)_n$OH, $(CH_2)_nOH$, $CH_2NH(CH_2)_n$—OH, $CH_2NH(CH_2)_n$—$NR_aR_b$, $CONH$—$(CH_2)_nNR_aR_b$,
in particular compounds of formula VI selected from the group consisting of:

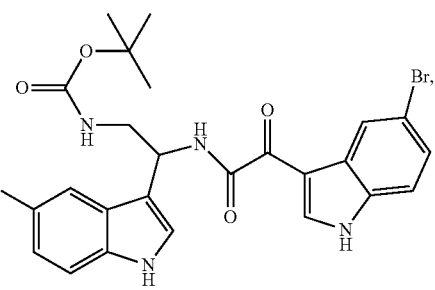

4

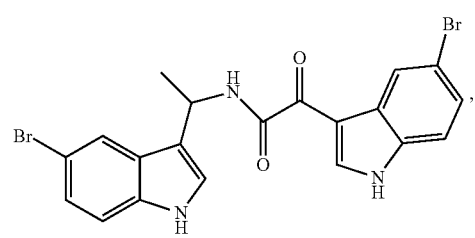

5 or compounds of the following general formula VII:

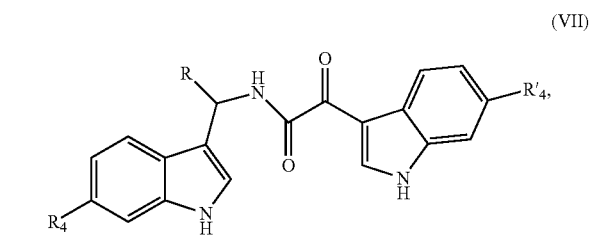

(VII)

wherein:
$R_4$ and $R'_4$ each independently represents H, F, Cl, Br, I, and at least one of $R_4$ and $R'_4$ represents F, Cl, Br, I, and
R represents a $(C_1-C_7)$-alkyl, $CH_2NHCO_2(C_1-C_7)$-alkyl, $CO_2H$, $CO_2$—$(C_1-C_7)$-alkyl, $CONH$—$(CH_2)_n$OH, (CH$_2$)$_n$OH, CH$_2$NH(CH$_2$)$_n$—OH, CH$_2$NH(CH$_2$)$_n$—NR$_a$R$_b$, CONH—(CH$_2$)$_n$—NR$_a$R$_b$, in particular compounds having the following structure:

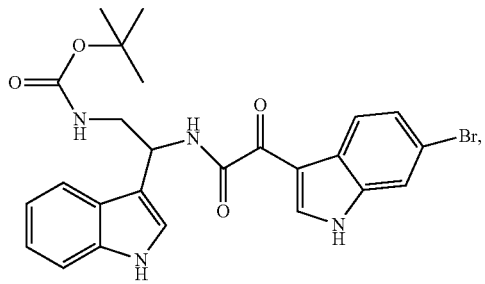

3 or compounds of the following formula V-1:

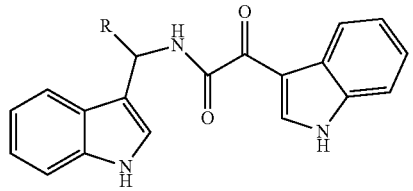

(V-1)

wherein:
R represents a (C$_1$-C$_7$)-alkyl, CH$_2$NHCO$_2$—(C$_1$-C$_7$)-alkyl, CO$_2$H, CO$_2$—(C$_1$-C$_7$)-alkyl, CONH—(CH$_2$)$_n$OH, (CH$_2$)$_n$OH, CH$_2$NH(CH$_2$)$_n$—OH, CH$_2$NH(CH$_2$)$_n$—NR$_a$R$_b$, CONH—(CH$_2$)$_n$NR$_a$R$_b$, in particular compounds having the following structure:

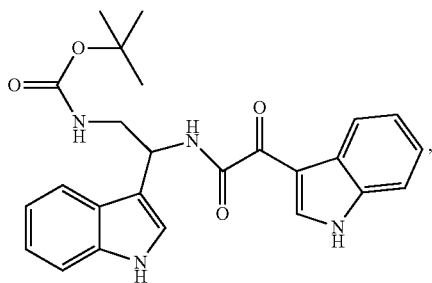

2 or compounds of the following general formula VIII:

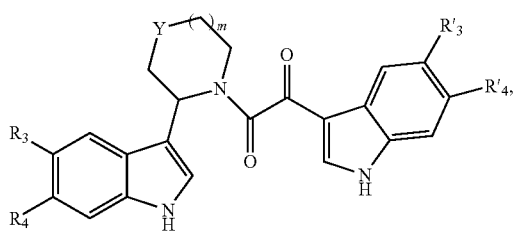

(VIII)

wherein:
Y=N—R$_8$=NBoc or NH, or
Y=CH$_2$, CH—R$_8$, R$_8$ being as previously defined,
R$_3$, R$_4$, R'$_3$ and R'$_4$ each independently represents H, F, Cl, Br, I, and
m=0 or 1, in particular compounds selected from the group consisting of:

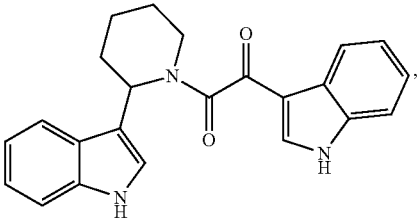

6a

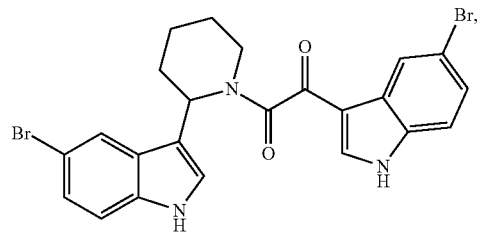

6d

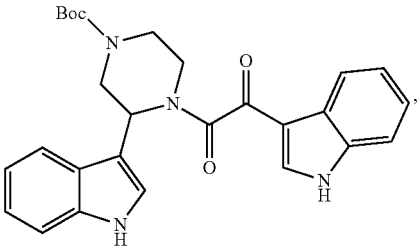

6c

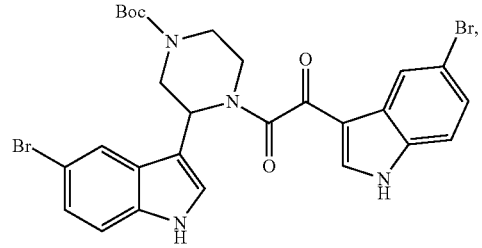

6f

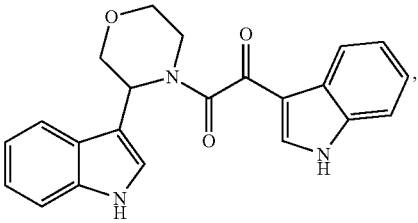

6b

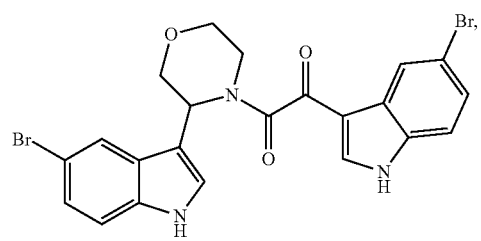

6e

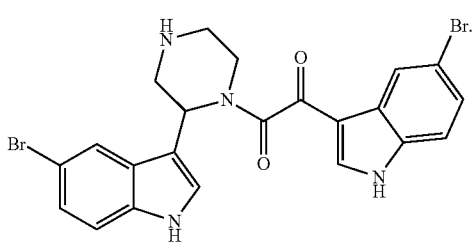

13. The pharmaceutical composition according to claim 1, wherein said compound is in an effective amount for having an antibacterial activity and/or being a NorA efflux pump inhibitor.

14. The pharmaceutical composition according to claim 13, wherein the antibacterial activity is against Gram-positive and Gram-negative bacteria.

15. The pharmaceutical composition according to claim 13, wherein said bacteria are resistant to conventional antibiotics.

16. The pharmaceutical composition according to claim 13, wherein the antibacterial activity is against *Staphylococcus* species, in particular *Staphylococcus aureus*, especially *Staphylococcus aureus* resistant to β-lactams, including methicillin-resistant strains (also referred as MRSA), *Staphylococcus aureus* resistant to glycopeptides, vancomycin-resistant or glycopeptide-resistant strains (also referred as VISA or GISA), and Staphylococcus aureus resistant to fluoroquinolones.

17. The pharmaceutical composition according to claim 13, having further an antifungal and/or antiviral activity.

18. The pharmaceutical composition according to claim 4, wherein said at least one antibiotic is selected from the group consisting of the fluoroquinolones family, ciprofloxacin, norfloxacin, pefloxacin, enofloxacin, ofloxacin, levofloxacin and moxifloxacin.

19. A method for an antibacterial treatment comprising administering to a patient in need thereof an effective amount of the pharmaceutical composition according to claim 1.

20. A method for an antibacterial treatment comprising administering to a patient in need thereof an effective amount of the pharmaceutical composition according to claim 4 and further at least one antibiotic compound.

* * * * *